United States Patent
Pardridge et al.

(10) Patent No.: US 10,906,981 B2
(45) Date of Patent: Feb. 2, 2021

(54) COMPOSITIONS AND METHODS RELATED TO STRUCTURES THAT CROSS THE BLOOD BRAIN BARRIER

(71) Applicants: The Regents of the University of California, Oakland, CA (US); ArmaGen Technologies, Inc., Calabasas, CA (US)

(72) Inventors: William M. Pardridge, Pacific Palisades, CA (US); Ruben J. Boado, Agoura Hills, CA (US)

(*) Notice: Subject to any disclaimer, the term of this patent is extended or adjusted under 35 U.S.C. 154(b) by 356 days.

(21) Appl. No.: 14/906,259

(22) PCT Filed: Jul. 17, 2014

(86) PCT No.: PCT/US2014/047082
§ 371 (c)(1),
(2) Date: Jan. 19, 2016

(87) PCT Pub. No.: WO2015/009961
PCT Pub. Date: Jan. 22, 2015

(65) Prior Publication Data
US 2016/0152719 A1 Jun. 2, 2016

Related U.S. Application Data

(60) Provisional application No. 61/856,499, filed on Jul. 19, 2013, provisional application No. 61/857,186, filed on Jul. 22, 2013.

(51) Int. Cl.
*G01N 33/66* (2006.01)
*C07K 16/28* (2006.01)
*C07K 14/475* (2006.01)

(52) U.S. Cl.
CPC ........ *C07K 16/2869* (2013.01); *C07K 14/475* (2013.01); *G01N 33/66* (2013.01); *C07K 2317/75* (2013.01); *C07K 2317/76* (2013.01); *C07K 2319/00* (2013.01); *G01N 2400/00* (2013.01); *G01N 2800/042* (2013.01); *G01N 2800/52* (2013.01)

(58) Field of Classification Search
None
See application file for complete search history.

(56) References Cited

U.S. PATENT DOCUMENTS

| 7,125,843 | B2 | 10/2006 | DeFrees et al. | |
|---|---|---|---|---|
| 8,142,781 | B2 | 3/2012 | Pardridge et al. | |
| 8,741,260 | B2 | 6/2014 | Pardridge et al. | |
| 8,859,515 | B2 | 10/2014 | Collard et al. | |
| 2007/0081992 | A1* | 4/2007 | Pardridge | A61P 27/02 424/143.1 |
| 2009/0053219 | A1* | 2/2009 | Pardridge | C07K 16/2869 424/133.1 |
| 2011/0021590 | A1* | 1/2011 | Duggan | C07D 403/12 514/397 |

FOREIGN PATENT DOCUMENTS

WO   WO 2000/051621 A1   9/2000

OTHER PUBLICATIONS

Gardner et al J Inherit Metab Dis 34: 489-897, 2011.*
Vahabzadeh et al (Eu J Neurosc 7: 175-179, 1995).*
Boado (Drug New Perspect 21: 489-503, 2008—abstract).*
Precose Official FDA information, side effects and uses (revised Jan. 2008), downloaded on Feb. 19, 2018, pp. 1-12, <https://web.archive.org/web/20081020032144/www.drugs.com/pro/precose.html>.*
de Herder et al (Clin Endo 75: 277-284, 2011).*
Boado (Drug New Perspect 21: 489-503, 2008).*
Boado et al (Biotechno Bioengin 108: 186-196, 2011).*
Boado et al. (Biconj Chem 24, 97-104, Dec. 18, 2012).*
Lu et al (Biotechnol Bioengineer 108 1954-1964, 2011).*
Bhaskar, et al. (2012) "A fully human, allosteric monoclonal antibody that activates the insulin receptor and improves glycemic control." *Diabetes*, 61(5): 1263-1271.
Boado, et al. (2008) "Genetic engineering of a lysosomal enzyme fusion protein for targeted delivery across the human blood-brain barrier." *Biotechnol Bioeng.*, 99(2):475-484.
Boado, et al. (2009) "AGT-181: expression in CHO cells and pharmacokinetics, safety, and plasma iduronidase enzyme activity in Rhesus monkeys." *J Biotechnol.*, 144(2): 135-141.
Boado, et al. (2011) "Reversal of lysosomal storage in brain of adult MPS-I mice with intravenous Trojan horse-iduronidase fusion protein." *Mol Pharm* 8: 1342-1350.
Boado, et al. (2012) "Glycemic control and chronic dosing of rhesus monkeys with a fusion protein of iduronidase and a monoclonal antibody against the human insulin receptor." *Drug Metab Dispos.*, 40(10): 2021-2025.
Brady and Schiffmann (2004) "Enzyme-replacement therapy for metabolic storage disorders." *Lancet Neurol* 3: 752-756.
Brunetti, et al. (1989) "Monoclonal antibodies to the human insulin receptor mimic a spectrum of biological effects in transfected 3T3/HIR fibroblasts without activating receptor kinase." Biochem Biophys Res Commun 165: 212-218.
Davis, et al. (1993) "Metabolic disturbances in Plasmodium coatneyi-infected rhesus monkeys." *Int J Parasitol* 23: 557-563.
GenBank Accession No. NM_000208.
GenBank Accession No. NP_000193.
GenBank Accession No. NP_000194.
Hasselbalch, et al. (1999) "No effect of insulin on glucose blood-brain barrier transport and cerebral metabolism in humans." *Diabetes* 48: 1915-1921.
Malek, et al. (2010) "Treatment of type B insulin resistance: a novel approach to reduce insulin receptor autoantibodies." *J Clin Endocrinol Metab.*, 95(8):3641-3647.

(Continued)

Primary Examiner — Daniel E Kolker
Assistant Examiner — Aditi Dutt
(74) Attorney, Agent, or Firm — Biopatent Services; Gary Baker

(57) ABSTRACT

Provided herein are compositions, kits, methods and systems related to administering a structure that crosses the blood brain barrier (BBB) along with a monosaccharide, either simultaneously or consecutively. The structure may be, for example an antibody or fusion antibody that binds to an insulin receptor.

15 Claims, 14 Drawing Sheets

Specification includes a Sequence Listing.

(56) References Cited

OTHER PUBLICATIONS

Miebach, E. (2005) "Enzyme replacement therapy in mucopolysaccharidosis type 1." *Acta Paediatr Suppl* 94: 58-60.

Pardridge and Boado (2009) "Pharmacokinetics and safety in rhesus monkeys of a monoclonal antibody-GDNF fusion protein for targeted blood-brain barrier delivery." *Pharm Res.*, 26(10): 2227-2236.

Pardridge and Yang (1985) "Human blood-brain barrier insulin receptor." *J Neurochem* 44: 1771-1778.

Powers, W.J. (1981) "Cerebrospinal fluid to serum glucose ratios in diabetes mellitus and bacterial meningitis." *Am J Med* 71: 217-220.

Whittaker and Whittaker (2005) "Characterization of the Functional Insulin Binding Epitopes of the Full-length Insulin Receptor." *J Biol Chem.*, 280(22): 20932-20936.

Wraith, J.E. (2001) "Enzyme replacement therapy in mucopolysaccharidosis type I: progress and emerging difficulties." *J Inherit Metab Dis* 24: 245-250.

Yip and Ottensmeyer (2003) "Three-dimensional Structural Interactions of Insulin and Its Receptor." J Biol Chem., 278(30): 27329-27332.

Zhou, et al. (2012) "Brain-penetrating IgG-iduronate 2-sulfatase fusion protein for the mouse." *Drug Metab Dispos.*, 40(2): 329-335.

International Search Report for PCT/US2014/047082, dated Dec. 15, 2014.

Hasselbalch, et al. (Oct. 1999) "No Effect of Insulin on Glucose Blood-Brain Barrier Transport and Cerebral Metabolism in Humans." *Diabetes*, 48: 1915-1921.

Auclair, et al. (1999) "Antiinsulin Receptor Autoantibodies Induce Insulin Receptors to Constitutively Associate with Insulin Receptor Substrate-1 and -2 and Cause Severe Cell Resistance to Both Insulin and Insulin-Like Growth Factor I*." *JCE&M*, 84(9):3197-3206.

Maiza, et al. (2013) "Anti-Insulin Receptor Antibodies Related to Hypoglycemia in a Previously Diabetic Patient." *Diabetes Care*, 36: e77.

Soos, et al. (1989) "Monoclonal antibodies to the insulin receptor mimic metabolic effects of insulin but do not stimulate receptor autophosphorylation in transfected NIH 3T3 fibroblasts." *Proc. Natl. Acad. Sci. USA*, 86: 5217-5221.

Sozmen, et al. (2001) "Catalase/Superoxide Dismutase (SOD) and Catalase/Paraoxonase (PON) Ratios May Implicate Poor Glycemic Control." *Arch. Med. Res.* 32:283-287.

* cited by examiner

FIGURE 7

HIR Ab HC (SEQ ID NO:1)

<u>MDWTWRVFCLLAVAPGAHS</u>QVQLQQSGPELVKPGALVKISCKASG<u>YTFTNYDIH</u>W

VKQRPGQGLEWIG<u>WIYPGDGSTKYNEKFKG</u>KATLTADKSSSTAYMHLSSLTSEKS

AVYFCAR<u>EWAY</u>WGQGTLVTVS*AASTKGPSVFPLAPSSKSTSGGTAALGCLVKDYF*

*PEPVTVSWNSGALTSGVHTFPAVLQSSGLYSLSSVVTVPSSSLGTQTYICNVNHK*

*PSNTKVDKKVEPKSCDKTHTCPPCPAPELLGGPSVFLFPPKPKDTLMISRTPEVT*

*CVVVDVSHEDPEVKFNWYVDGVEVHNAKTKPREEQYNSTYRVVSVLTVLHQDWLN*

*GKEYKCKVSNKALPAPIEKTISKAKGQPREPQVYTLPPSRDELTKNQVSLTCLVK*

*GFYPSDIAVEWESNGQPENNYKTTPPVLDSDGSFFLYSKLTVDKSRWQQGNVFSC*

*SVMHEALHNHYTQKSLSLSPGK*

FIGURE 8

HIR Ab LC (SEQ ID NO:2)

METPAQLLFLLLLWLPDTTGDIQMTQSPSSLSASLGERVSLTCRASQDIGGNLYW

LQQGPDGTIKRLIYATSSLDSGVPKRFSGSRSGSDYSLTISSLESEDFVDYYCLQ

YSSSPWTFGGGTKMEIKR*TVAAPSVFIFPPSDEQLKSGTASVVCLLNNFYPREAK*

*VQWKVDNALQSGNSQESVTEQDSKDSTYSLSSTLTLSKADYEKHKVYACEVTHQG*

*LSSPVTKSFNRGEC*

FIGURE 9

Amino Acid Sequence of IDUA (minus signal peptide)
(SEQ ID NO:3)

EAPHLVQVDAARALWPLRRFWRSTGFCPPLPHSQADQYVLSWDQQLNLAYVGAVP

HRGIKQVRTHWLLELVTTRGSTGRGLSYNFTHLDGYLDLLRENQLLPGFELMGSA

SGHFTDFEDKQQVFEWKDLVSSLARRYIGRYGLAHVSKWNFETWNEPDHHDFDNV

SMTMQGFLNYYDACSEGLRAASPALRLGGPGDSFHTPPRSPLSWGLLRHCHDGTN

FFTGEAGVRLDYISLHRKGARSSISILEQEKVVAQQIRQLFPKFADTPIYNDEAD

PLVGWSLPQPWRADVTYAAMVVKVIAQHQNLLLANTTSAFPYALLSNDNAFLSYH

PHPFAQRTLTARFQVNNTRPPHVQLLRKPVLTAMGLLALLDEEQLWAEVSQAGTV

LDSNHTVGVLASAHRPQGPADAWRAAVLIYASDDTRAHPNRSVAVTLRLRGVPPG

PGLVYVTRYLDNGLCSPDGEWRRLGRPVFPTAEQFRRMRAAEDPVAAAPRPLPAG

GRLTLRPALRLPSLLLVHVCARPEKPPGQVTRLRALPLTQGQLVLVWSDEHVGSK

CLWTYEIQFSQDGKAYTPVSRKPSTFNLFVFSPDTGAVSGSYRVRALDYWARPGP

FSDPVPYLEVPVPRGPPSPGNP

FIGURE 10

Amino Acid Sequence of HIRMAb-HC-IDUA (SEQ ID NO:4)

MDWTWRVFCLLAVAPGAHSQVQLQQSGPELVKPGALVKISCKASGYTFTNYDIHWVKQRPGQGL
EWIGWIYPGDGSTKYNEKFKGKATLTADKSSSTAYMHLSSLTSEKSAVYFCAREWAYWGQGTLV
TVSAASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLV
KGFYPSDIAVEWESNGQPENNYKTTPPVLDSDGSFFLYSKLTVDKSRWQQGNVFSCSVMHEALH
NHYTQKSLSLSPGKSSEAPHLVQVDAARALWPLRRFWRSTGFCPPLPHSQADQYVLSWDQQLNL
AYVGAVPHRGIKQVRTHWLLELVTTRGSTGRGLSYNFTHLDGYLDLLRENQLLPGFELMGSASG
HFTDFEDKQQVFEWKDLVSSLARRYIGRYGLAHVSKWNFETWNEPDHHDFDNVSMTMQGFLNYY
DACSEGLRAASPALRLGGPGDSFHTPPRSPLSWGLLRHCHDGTNFFTGEAGVRLDYISLHRKGA
RSSISILEQEKVVAQQIRQLFPKFADTPIYNDEADPLVGWSLPQPWRADVTYAAMVVKVIAQHQ
NLLLANTTSAFPYALLSNDNAFLSYHPHPFAQRTLTARFQVNNTRPPHVQLLRKPVLTAMGLLA
LLDEEQLWAEVSQAGTVLDSNHTVGVLASAHRPQGPADAWRAAVLIYASDDTRAHPNRSVAVTL
RLRGVPPGPGLVYVTRYLDNGLCSPDGEWRRLGRPVFPTAEQFRRMRAAEDPVAAAPRPLPAGG
RLTLRPALRLPSLLLVHVCARPEKPPGQVTRLRALPLTQGQLVLVWSDEHVGSKCLWTYEIQFS
QDGKAYTPVSRKPSTFNLFVFSPDTGAVSGSYRVRALDYWARPGPFSDPVPYLEVPVPRGPPSP
GNP

FIGURE 11

Amino Acid Sequence of IDS (minus signal peptide) (SEQ ID NO:5)

```
SETQANSTTDALNVLLIIVDDLRPSLGCYGDKLVRSPNIDQLASHSLLFQNAFAQQAVCAPSRVS
FLTGRRPDTTRLYDFNSYWRVHAGNFSTIPQYFKENGYVTMSVGKVFHPGISSNHTDDSPYSWSF
PPYHPSSEKYENTKTCRGPDGELHANLLCPVDVLDVPEGTLPDKQSTEQAIQLLEKMKTSASPFF
LAVGYHKPHIPFRYPKEFQKLYPLENITLAPDPEVPDGLPPVAYNPWMDIRQREDVQALNISVPY
GPIPVDFQRKIRQSYFASVSYLDTQVGRLLSALDDLQLANSTIIAFTSDHGWALGEHGEWAKYSN
FDVATHVPLIFYVPGRTASLPEAGEKLFPYLDPFDSASQLMEPGRQSMDLVELVSLFPTLAGLAG
LQVPPRCPVPSFHVELCREGKNLLKHFRFRDLEEDPYLPGNPRELIAYSQYPRPSDIPQWNSDKP
SLKDIKIMGYSIPFTIDYRYTVWVGFNPDEFLANFSDIHAGELYFVDSDPLQDHNMYNDSQGGDLF
QLLMP
```

FIGURE 12

Amino Acid Sequence of HIR Ab-IDS HC (SEQ ID NO:6)

MDWTWRVFCLLAVAPGAHSQVQLQQSGPELVKPGALVKTSCKASGYTFTNYDIHWVKQRPGQGLE
WIGWIYPGDGSTKYNEKFKGKATLTADKSSSTAYMHLSSLTSEKSAVYFCAREWAYDGQGTLVTV
SAASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKS
LSLSPGSSSSETQANSTTDALNVLLIIVDDLRPSLGCYGDKLVRSPNIDQLASHSLLFQNAFAQQ
AVCAPSRVSFLTGRRPDTTRLYDFNSYWRVHAGNFSTIPQYFKENGYVTMSVGKVFHPGISSNHT
DDSPYSWSFPPYHPSSEKYENTKTCRGPDGELHANLLCPVDVLDVPEGTLPDKQSTEQAIQLLEK
MKTSASPFFLAVGYHKPHIPFRYPKEFQKLYPLENITLAPDPEVPDGLPPVAYNPWMDIRQREDV
QALNISVPYGPIPVDFQRKIRQSYFASVSYLDTQVGRLLSALDDLQLANSTIIAFTSDHGWALGE
HGEWAKYSNFDVATHVPLIFYVPGRTASLPEAGEKLFPYLDPFDSASQLMEPGRQSMDLVELVSL
FPTLAGLAGLQVPPRCPVPSFHVELCREGKNLLKHFRFRDLEEDPYLPGNPRELIAYSQYPRPSD
IPQWNSDKPSLKDIKIMGYSIRTIDYRYTVWVGFNPDEFLANFSDIHAGELYFVDSDPLQDHNMY
NDSQGGDLFQLLMP

FIGURE 13

Nucleotide sequence of HIR Ab-IDS HC (SEQ ID NO:7)

GCCGCCACCATGGACTGGACCTGGAGGGTGTTCTGCCTGCTTGCAGTGGCCCCCGGAGCCCACAGCCAGG
TTCAGCTGCAGCAGTCTGGACCTGAGCTGGTGAAGCCTGGGGCTTTAGTGAAGATATCCTGCAAGGCTTC
TGGTTACACCTTCACAAACTACGATATACACTGGGTGAAGCAGAGGCCTGGACAGGGACTTGAGTGGATT
GGATGGATTTATCCTGGAGATGGTAGTACTAAGTACAATGAGAAATTCAAGGGCAAGGCCACACTGACTG
CAGACAAATCCTCCAGCACAGCCTACATGCACCTCAGCAGCCTGACTTCTGAGAAATCTGCAGTCTATTT
CTGTGCAAGAGAGTGGGCTTACTGGGGCCAAGGGACTCTGGTCACTGTCTCTGCAGCTAGCACCAAGGGC
CCATCGGTCTTCCCCCTGGCACCCTCCTCCAAGAGCACCTCTGGGGGCACAGCGGCCCTGGGCTGCCTGG
TCAAGGACTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCCAGCAGC
TTGGGCACCCAGACCTACATCTGCAACGTGAATCACAAGCCCAGCAACACCAAGGTGGACAAGAAAGTTG
AGCCCAAATCTTGTGACAAAACTCACACATGCCCACCGTGCCCAGCACCTGAACTCCTGGGGGGACCGTC
AGTCTTCCTCTTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACCGTCCT
GCACCAGGACTGGCTGAATGGCAAGGAGTACAAGTGCAAGGTCTCCAACAAAGCCCTCCCAGCCCCCATC
GAGAAAACCATCTCCAAAGCCAAAGGGCAGCCCCGAGAACCACAGGTGTACACCCTGCCCCCATCCCGGG
ATGAGCTGACCAAGAACCAGGTCAGCCTGACCTGCCTGGTCAAAGGCTTCTATCCCAGCGACATCGCCGT
GGAGTGGGAGAGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTCTTCTCATGCT
CCGTGATGCATGAGGCTCTGCACAACCACTACACGCAGAAGAGCCTCTCCCTGTCTCCGGGTAGTAGTTC
CTCCGAAACGCAGGCCAACTCGACCACAGATGCTCTGAACGTTCTTCTCATCATCGTGGATGACCTGCGC
CCCTCCCTGGGCTGTTATGGGGATAAGCTGGTGAGGTCCCCAAATATTGACCAACTGGCATCCACAGCC
TCCTCTTCCAGAATGCCTTTGCGCAGCAAGCAGTGTGCCGCCCCGAGCCGCGTTTCTTTCCTCACTGGCAG
GAGACCTGACACCACCGCCTGTACGACTTCAACTCCTACTGGAGGGTGCACGCTGGAAACTTCTCCACC
ATCCCCCAGTACTTCAAGGAGAATGGCTATGTGACCATGTCGGTGGGAAAAGTCTTTCACCCTGGGATAT
CTTCTAACCATACTGATGATTCTCCGTATAGCTGGTCTTTTCCACCTTATCATCCTTCCTCTGAGAAGTA
TGAAAACACTAAGACATGTCGAGGGCCAGATGGAGAACTCCATGCCAACCTGCTTTGCCCTGTGGATGTG
CTGGATGTTCCCGAGGGCACCTTGCCTGACAAACAGAGCACTGAGCAAGCCATACAGTTGTTGAAAAGA
TGAAAACGTCAGCCAGTCCTTTCTTCCTGCCCGTTGGGTATCATAAGCCACACATCCCCTTCAGATACCC
CAAGGAATTTCAGAAGTTGTATCCCTTGGAGAACATCACCCTGGCCCCCGATCCCGAGGTCCCTGATGGC
CTACCCCCTGTGGCCTACAACCCCTGGATGGACATCAGGCAACGGGAAGACGTCCAAGCCTTAAACATCA
GTGTGCCGTATGGTCCAATTCCTGTGGACTTTCAGCGGAAAATCCGCCAGAGCTACTTTGCCTCTGTGTC
ATATTTGGATACACAGGTCGGCCGCCTCTTGAGTGCTTTGGACGATCTTCAGCTGGCCAACAGCACCATC
ATTGCATTTACCTCGGATCATGGGTGGGCTCTAGGTGAACATGGAGAATGGGCCAAATACAGCAATTTTG
ATGTTGCTACCCATGTTCCCCTGATATTCTATGTTCCTGGAAGGACGGCTTCACTTCCGGAGGCAGGCCA
GAAGCTTTTCCCTTACCTCGACCCTTTTGATTCGCCCTCACAGTTGATGGAGCCAGGCAGGCAATCCATG
GACCTTGTGGAACTTGTGTCTCTTTTTCCCACGCTGGCTGGACTTGCAGGACTGCAGGTTCCACCTCGCT
GCCCCGTTCCTTCATTTCACGTTGAGCTGTGCAGAGAAGGCAAGAACCTTCTGAAGCATTTTCGATTCCG
TGACTTGGAAGAGGATCCGTACCTTCCCTGGTAATCCCGTGAACTGATTGCCTATAGCCAGTATCCCGG
CCTTCAGACATCCCTCAGTGGAATTCTGACAAGCCGAGTTTAAAAGATATAAAGATCATGGGCTATTCCA
TACGCACCATAGACTATAGGTATACTGTGTGGGTTGGCTTCAATCCTGATGAATTTCTAGCTAACTTTTC
TGACATCCATGCAGGGGAACTGTATTTTGTGGATTCTGACCCATGCAGGATCACAATATGTATAATGAT
TCCCAAGGTGGAGATCTTTTCCAGTTGTTGATGCCTTGA

FIGURE 14

Nucleotide sequence of HIR Ab-IDS LC (SEQ ID NO 8)

```
GCCGCCACCATGGAGACCCCCGCCCAGCTGCTGTTCCTGTTGCTGCTTTGGCTTCCAGATACTACCGGCG
ACATCCAGATGACCCAGTCTCCATCCTCCTTATCTGCCTCTCTGGGAGAAAGAGTCAGTCTCACTTGTCG
GGCAAGTCAGGACATTGGTGGTAACTTATACTGGCTTCAGCAGGGACCAGATGGAACTATTAAACGCCTG
ATCTACGCCACATCCAGTTTAGATTCTGGTGTCCCCAAAAGGTTCAGTGGCAGTAGGTCTGGGTCAGATT
ATTCTCTCACCATCAGCAGCCTTGAGTCTGAAGATTTTGTAGACTATTACTGTCTACAGTATTCTAGTTC
TCCGTGGACGTTCGGTGGAGGCACAAAGCTGGAAATAAAACGAACTGTGGCTGCACCATCTGTCTTCATC
TTCCCGCCATCTGATGAGCAGTTGAAATCTGGAACTGCCTCTGTTGTGTGCCTGCTGAATAACTTCTATC
CCAGAGAGGCCAAAGTACAGTGGAAGGTGGATAACGCCCTCCAATCGGGTAACTCCCAGGAGAGTGTCAC
AGAGCAGGACAGCAAGGACAGCACCTACAGCCTCAGCAGCACCCTGACGCTGAGCAAAGCAGACTACGAG
AAACACAAAGTCTACGCCTGCGAAGTCACCCATCAGGGCCTGAGCTCGCCCGTCACAAAGAGCTTCAACA
GGGGAGAGTGTTAG
```

COMPOSITIONS AND METHODS RELATED TO STRUCTURES THAT CROSS THE BLOOD BRAIN BARRIER

CROSS REFERENCE

This application is a national phase entry in the United States under 35 U.S.C. § 371 from International Application Number PCT/US2014/047082 which has an international filing date of Jul. 17, 2014 and which claims the benefit of U.S. Provisional Application No. 61/856,499, filed Jul. 19, 2013; and U.S. Provisional Application No. 61/857,186, filed Jul. 22, 2013, all of which are incorporated herein by reference in their entirety.

STATEMENT AS TO FEDERALLY SPONSORED RESEARCH

This invention was made with government support under Grant No. NS064692 awarded by the National Institutes of Health. The government has certain rights in this invention.

BACKGROUND

The Blood Brain Barrier (BBB) is a protective barrier separating the brain from the blood flow connected to the rest of the body. The BBB can regulate the passage of molecules in and out of the brain, thereby preventing unintended molecules from accessing this critical organ. For example, the BBB can be highly effective in preventing bacterial infections of the brain.

Brain and/or central nervous system disorders can be difficult to treat due to the decreased ability of molecules to effectively permeate the BBB and enter the brain. New methods and compositions are needed to improve fusion antibodies.

SUMMARY

This disclosure provides, among other things, kits comprising (a) a structure that binds to a receptor expressed on the blood brain barrier (BBB), and (b) a monosaccharide. In some embodiments, the receptor expressed on the BBB is an insulin receptor, a transferrin receptor, an insulin-like growth factor (IGF) receptor, a leptin receptor, or a lipoprotein receptor. In preferred embodiments, the receptor is an insulin receptor, and more preferably a human insulin receptor (HIR). In some embodiments, the structure is an antibody. In some embodiments, the structure is an antibody to the HIR. In some embodiments, the structure is a fusion antibody. In some embodiments, the fusion antibody comprises the amino acid sequence of a heavy chain immunoglobulin or a light chain immunoglobulin covalently linked to the amino acid sequence of a polypeptide. In some embodiments, the amino acid sequence of the polypeptide is covalently linked to the heavy chain immunoglobulin. In some embodiments, the amino acid sequence of the polypeptide is covalently linked to the light chain immunoglobulin. In some embodiments, the amino acid sequence of the polypeptide encodes for a receptor extracellular domain. In some embodiments, the amino acid sequence of a polypeptide encodes for a lysosomal enzyme. In some embodiments, the enzyme is selected from the group comprising: alpha-L-iduronidase, iduronate-2 sulfatase, and an arylsulfatase. In some embodiments, the amino acid sequence of the polypeptide encodes iduronate 2 sulfatase (IDS). In some embodiments, the amino acid sequence of the polypeptide encodes alpha-L-iduronidase (IDUA). In some embodiments, the polypeptide is a neurotrophin. In some embodiments, the amino acid sequence of the polypeptide is fused to the carboxy terminus of the heavy chain immunoglobulin or the light chain immunoglobulin. In some embodiments, the fusion antibody acts as an agonist of the receptor on the BBB. In some embodiments, the fusion antibody acts as an antagonist of the receptor of the BBB. In some embodiments, the monosaccharide is selected from the group consisting of: glucose, dextrose, fructose, galactose, xylose, ribose, and any combination thereof. In some embodiments, the monosaccharide is glucose. In some embodiments, the monosaccharide is dextrose. In some embodiments, the structure and the monosaccharide are contained in separate vessels. In some embodiments, the structure and the monosaccharide are contained in the same vessel. In some embodiments, the structure and the monosaccharide are in a solution. In some embodiments, the solution comprises saline. In some embodiments, the solution comprises at least 5% monosaccharide. In some embodiments, the monosaccharide is glucose or dextrose. In some embodiments, the solution comprises less than 10% monosaccharide, less than 15% monosaccharide, or less than 20% monosaccharide.

In some embodiments, a method for treating a subject with a central nervous system (CNS) disorder can comprise administering to the subject a structure that binds to a receptor expressed on the blood brain barrier (BBB), a monosaccharide, wherein the administering treats a subject with a CNS disorder. In some embodiments, the administering is through a route selected from the group consisting of: intravenous, intra-arterial, intramuscular, subcutaneous, intraperitoneal, intranasal, transbuccal, transdermal, rectal, transalveolar and oral. In some embodiments, the disorder is selected from the group comprising Hurler's Syndrome, Hunter's Syndrome, Type I mucopolysaccharidosis, Type II mucopolysaccharidosis, or a lysosomal storage disorder. In some embodiments, the disorder is Hurler's Syndrome. In some embodiments, the disorder is Hunter's Syndrome. In some embodiments, the structure is an antibody. In some embodiments, the structure is a fusion antibody. In some embodiments, the structure is a fusion antibody comprising: an amino acid sequence of a heavy chain immunoglobulin or a light chain immunoglobulin covalently linked to the amino acid sequence of a polypeptide. In some embodiments, the amino acid sequence of the polypeptide is covalently linked to the heavy chain immunoglobulin. In some embodiments, the fusion antibody binds to a receptor expressed on the BBB. In some embodiments, the receptor expressed on the BBB is an insulin receptor, a transferrin receptor, an insulin-like growth factor (IGF) receptor, a leptin receptor, or a lipoprotein receptor. In some embodiments, the receptor expressed on the BBB is an insulin receptor. In some embodiments, the insulin receptor is a human insulin receptor. In some embodiments, the amino acid sequence of the polypeptide encodes for an enzyme. In some embodiments, the amino acid sequence of the polypeptide encodes for a lysosomal enzyme. In some embodiments, the lysosomal enzyme is selected from the group consisting of alpha-iduronidase, iduronate-2 sulfatase, and an arylsulfatase. In some embodiments, the amino acid sequence of the polypeptide encodes for iduronate 2 sulfatase (IDS). In some embodiments, the amino acid sequence of a polypeptide encodes for iduronidase (IDUA), also known as alpha-L-iduronidase or L-iduronidase. In some embodiments, the fusion antibody acts as an agonist. In some embodiments, the fusion antibody acts as an antagonist. In some embodiments, the monosaccharide is selected from the group consisting of: glucose, dextrose, fructose, galactose, xylose, and ribose. In some embodiments, the monosaccharide is glucose. In some embodiments, the monosaccharide is dextrose. In some embodiments, the monosaccharide and structure are present in the same solution. In some embodiments, the solution comprises greater than 5% monosaccharide. In some embodiments, the monosaccharide is glucose or dextrose. In some embodiments, the monosaccharide is administered to the patient after the structure is administered to the patient. In some embodiments, the structure causes hypoglycemia. In some embodiments, the monosaccharide ameliorates the hypoglycemia.

In some embodiments, a method for treating a subject with a central nervous system disorder can comprise administering to the subject a fusion antibody, wherein the fusion antibody binds to a receptor expressed on the BBB, monitoring glucose levels in the subject, wherein the monitoring determines if the subject is hypoglycemic or hyperglycemic, and treating the hypoglycemic or hyperglycemic subject. In some embodiments, the administering is through a route selected from the group consisting of intravenous, intraarterial, intramuscular, subcutaneous, intraperitoneal, intranasal, transbuccal, transdermal, rectal, transalveolar and oral. In some embodiments, the disorder is selected from the group comprising Hurler's Syndrome, Hunter's Syndrome, Type I mucopolysaccharidosis, Type II mucopolysaccharidosis, or a lysosomal storage disorder. In some embodiments, the disorder is Hurler's Syndrome. In some embodiments, the disorder is Hunter's Syndrome. In some embodiments, the receptor expressed on the BBB is an insulin receptor, a transferrin receptor, an insulin-like growth factor (IGF) receptor, a leptin receptor, or a lipoprotein receptor. In some embodiments, the receptor expressed on the BBB is an insulin receptor. In some embodiments, the insulin receptor is a human insulin receptor. In some embodiments, the fusion antibody comprises a polypeptide that encodes for an enzyme. In some embodiments, the enzyme is selected from the group comprising: iduronidase, iduronate-2 sulfatase, and aryl sulfatase. In some embodiments, the treating comprises administering a therapeutic that reduces hyperglycemia or hypoglycemia. In some embodiments, the monitoring determines whether the subject is hypoglycemic. In some embodiments, the treating comprises administering a monosaccharide to the subject. In some embodiments, the method further comprises monitoring the subject following administration of the monosaccharide in order to determine whether the patient is hypoglycemic or hyperglycemic. In some embodiments, the method further comprises administering to the subject a therapeutic for hypoglycemia if, following administration of the monosaccharide, the patient continues to be hypoglycemic. In some embodiments, the method further comprises administering to the subject a therapeutic for hyperglycemia if, following administration of the monosaccharide, the patient is hyperglycemic. In some embodiments, the monitoring comprises monitoring glucose levels in blood of the subject. In some embodiments, the monitoring comprises monitoring glucose levels in cerebrospinal fluid of the subject.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, as follow:

FIG. 7 provides the amino acid sequence of the human insulin receptor (HIR) antibody (Ab) heavy chain.
FIG. 8 provides the amino acid sequence of the human insulin receptor (HIR) Ab light chain.
FIG. 9 provides the amino acid sequence of a-L-iduronidase (IDUA).
FIG. 10 provides the amino acid sequence of the HIR Ab heavy chain-a-L-iduronidase (IDUA) fusion polypeptide.
FIG. 11 provides the amino acid sequence of 2-sulfatase (IDS).
FIG. 12 provides the amino acid sequence of the HIR Ab heavy chain-IDS fusion.
FIG. 13 provides the nucleotide sequence of the HIR Ab heavy chain-IDS fusion.
FIG. 14 provides the nucleotide sequence of the HIR Ab light chain-IDS fusion.

DETAILED DESCRIPTION OF THE INVENTION

General Overview

Figure 1:
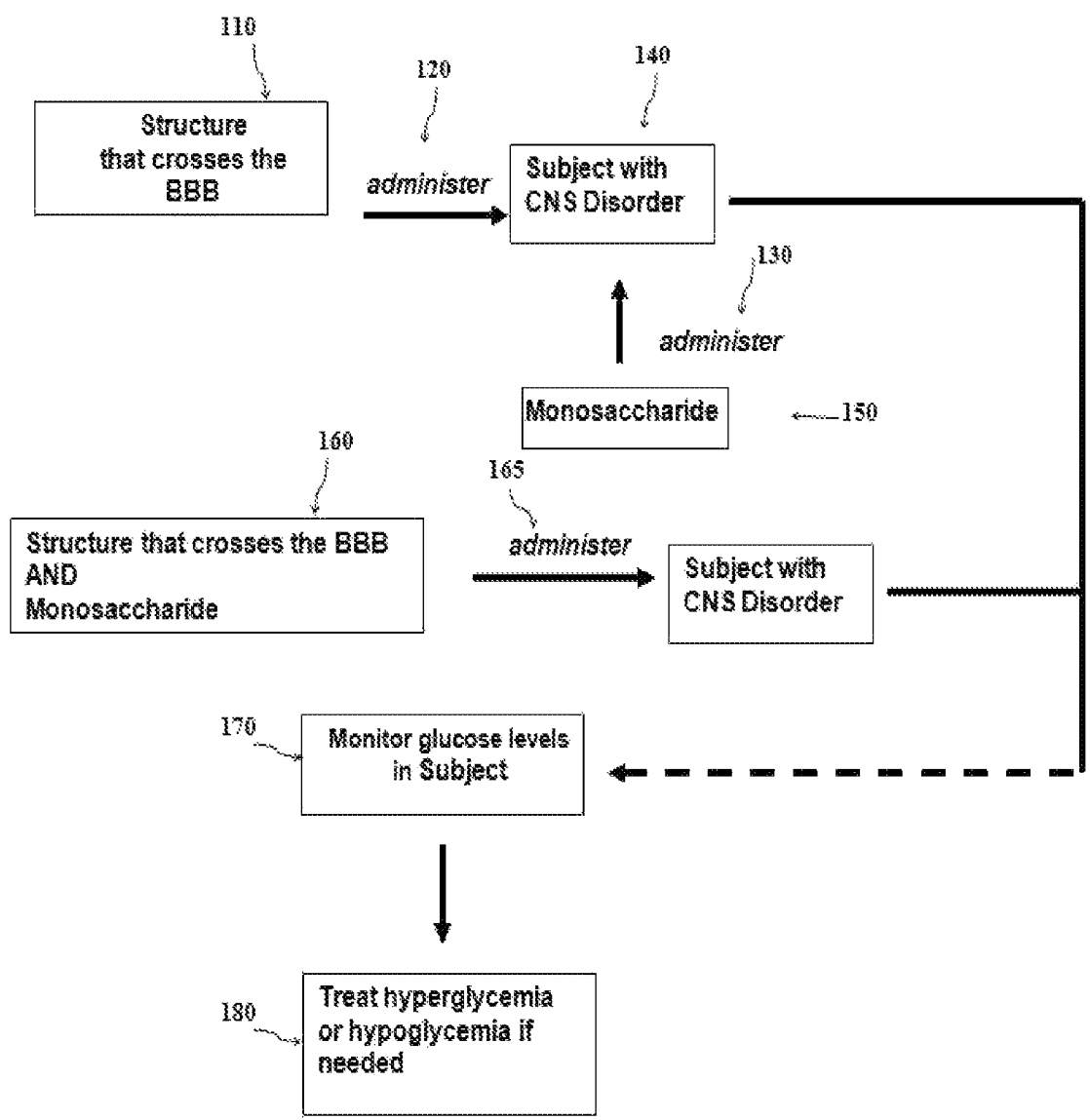
FIG. 1 depicts an exemplary method of the disclosure.

This disclosure provides improved methods, kits, compositions, and systems for delivering structures to a subject, particularly structures that may interact with a receptor that is expressed on the blood brain barrier (BBB) such as an insulin receptor (e.g., human insulin receptor (HIR)). In some cases, a kit is provided that comprises both the structure and a substance such as a monosaccharide (e.g., dextrose, glucose). In other cases, a method is provided that comprises administering to a subject the structure and the substance.

The structure may comprise a macromolecule such as a polypeptide. In some cases, the polypeptide is an antibody or immunoglobulin. The structure may comprise a fragment of an antibody or immunoglobulin. In other cases, the structure is not an antibody or immunoglobulin; for example, it may be a polypeptide capable of binding a receptor expressed on the BBB. The structure (e.g., antibody, fusion antibody, polpeptide, etc.) may bind to a receptor expressed on the BBB, for example, an insulin receptor (e.g., HIR). In other cases, the structure comprises a molecule or chemical that is not a polypeptide molecule.

The structure may comprise a fusion protein (or antibody), such as a bifunctional polypeptide or bifunctional antibody. For example, the structure may be an antibody or polypeptide fused or linked to an agent, such as a polypeptide agent or enzyme. In some cases, the enzyme is a lysosomal enzyme. Exemplary lysosomal enzymes include, but are not limited to, iduronate 2 sulfatase (IDS) and iduronidase (IDUA), which is also known as alpha-L-iduronidase or L-iduronidase. In some embodiments, the lysosomal enzyme is part of a system of glycosaminoglycan alpha-L-iduronohydrolases. In some cases, the fusion antibodies include an antibody to HIR (HIR Ab) fused to a lysosomal enzyme such as IDUA IDS. In some cases, the HIR Ab is fused to the N terminal of the IDUA or IDS (e.g., HIR Ab-IDS, HIR Ab-IDUA); or in other cases the HIR Ab is fused to the C terminal of the IDUA or IDS (e.g., IDS-HIR Ab, IDUA-HIR Ab). In some cases, the HIR Ab is fused to a neurotrophin such as a neurotrophin described herein. In other cases, the HIR Ab can be conjugated to a different polypeptide or small molecule including siRNA, miRNA or to a toxin. In still other cases, the HIR Ab is fused to a ScFv antibody.

This disclosure provides methods, kits, compositions and systems for administering a first structure (e.g., a fusion polypeptide comprising an antibody to an insulin receptor) either along with, before, or after administering a second agent that ameliorates an adverse effect of the first agent. In other cases, the second agent prevents an adverse effect caused by the first agent. Often, the second agent is a therapeutic, such as a drug. In some cases, the second agent is a monosaccharide (e.g., glucose, dextrose, etc.).

In some instances, the structure comprises an antibody that acts as an agonist when it interacts with the BBB receptor (e.g., human insulin receptor). An agonist can activate the receptor to which it is bound. For example, if the fusion antibody acts as an agonist on the HIR, this can increase the activity of the receptor. The increased activity of the HIR human can lead to an increase in the amount of glucose that is removed from blood or cerebrospinal fluid, and therefore can cause hypoglycemia.

In some instances, the structure comprises an antibody that can act as an antagonist when it interacts with the BBB receptor. An antagonist can inactivate the receptor to which it is bound. For example, the fusion antibody may act as an antagonist of the HIR and decrease the activity of the receptor. An underactive human insulin receptor (e.g., one bound by an antagonist), can result in excessive glucose levels in blood and therefore may lead to hyperglycemia.

Accordingly, the disclosure provides for compositions and methods for delivering a structure to the central nervous system of a subject by administering to a subject a therapeutically effective dose of the structure that binds a receptor expressed on the BBB (e.g., human insulin receptor), with a substance that may alleviate hypoglycemia and/or hyperglycemia.

FIG. 1 depicts some exemplary methods and compositions of the disclosure. The method may comprise administering a structure and an agent (e.g., monosaccharide (e.g., glucose)), either at the same time or sequentially. A structure 110 can be administered 120 to a subject with a CNS disorder 140. When an agent (e.g., monosaccharide 150) is administered separately from the structure 110, it may be administered before or after the structure 110 is administered. In some embodiments, the monosaccharide 150 can be administered after monitoring glucose levels in a subject. In some embodiments, the monosaccharide 150 can be administered before monitoring glucose levels in a subject. In some embodiments, the monosaccharide 150 can be used to treat hypoglycemia.

In some embodiments, the structure and the monosaccharide 160 can be administered simultaneously to a subject with a CNS disorder 140. The subject that has been administered the structure and/or monosaccharide can be monitored 170 for changes in glucose levels. If glucose levels have been altered (e.g., lowered, thereby indicating possible hypoglycemia), or raised, thereby indicating possible hyperglycemia)) the subject may be treated with agents that can treat hyperglycemia or hypoglycemia 180.

Figure 2:
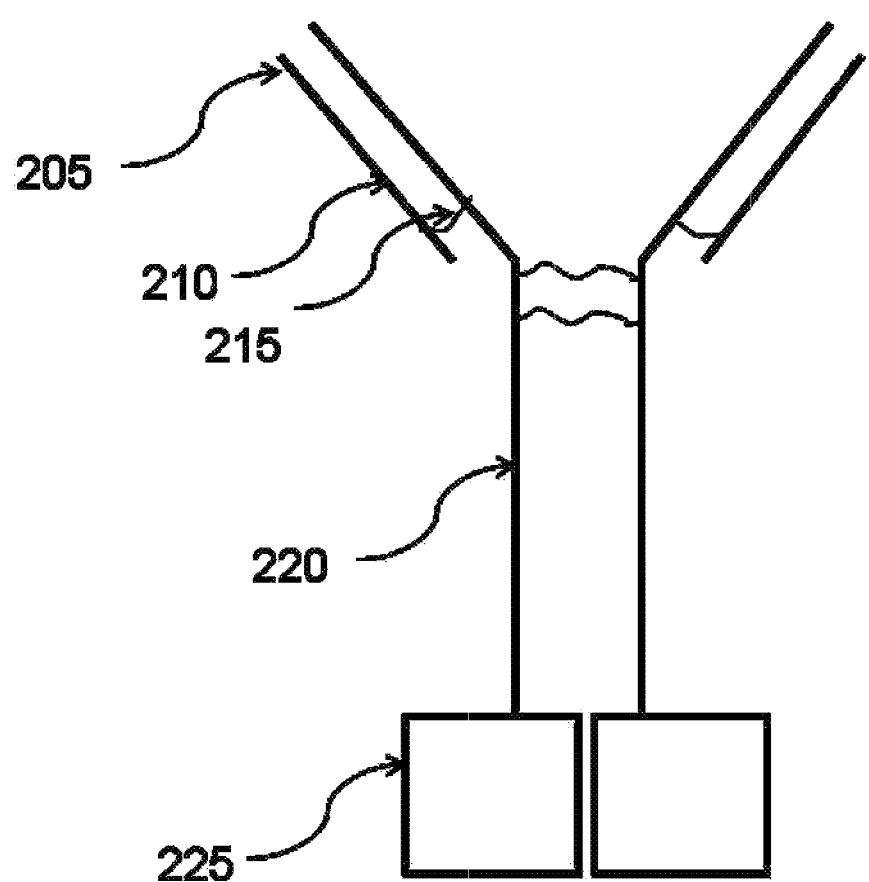
FIG. 2 depicts an exemplary structure.

FIG. 2 depicts an exemplary fusion antibody of the disclosure. A fusion antibody can comprise a heavy chain 220 and a light chain 210. The heavy chain 220 and the light chain 210 can be linked together by disulfide bonds 215. The fusion antibody can comprise an antigen binding region 205 that can comprise the variable domain. In some instances, the antigen binding region 205 can bind to a receptor expressed on the BBB (e.g., human insulin receptor). A polypeptide sequence 225 can be fused to the heavy chain 220 and/or light chain 210. The polypeptide sequence 225 can comprise a sequence that has a neuroprotective function after it crosses the BBB. In some instances, the polypeptide sequence can be a lysosomal enzyme (e.g., IDUA, IDS, etc.), a receptor extracellular domain (ECD), an enzyme, a ScFv, or a protein suitable for introduction into the CNS (e.g., a protein with neuroprotective function such as a neurotrophin).

The Blood Brain Barrier

The Blood Brain Barrier (BBB) can be formed by tight junctions that can cement together the endothelial cells that form the capillaries of the brain and spinal cord. There are 400 miles of brain capillaries in the human brain. The electrical resistance across the brain capillary endothelial plasma membrane, which forms the BBB in vivo, can be as high as in any biological membrane. The usual para-cellular and trans-cellular pathways for free solute exchange between the blood and an organ may be absent in the CNS. Consequently, a drug in blood can generally access the brain only via one of two mechanisms: (i) free diffusion owing to high lipid solubility of small molecules, and (ii) transport via an endogenous BBB transporter. One approach to solving the BBB drug delivery problem for fusion antibodies can be to re-engineer the fusion antibody so that it can access certain endogenous transport systems within the BBB. The methods described herein can permit a structure to cross the BBB from the peripheral blood into the CNS following systemic administration of a structure (e.g., antibody, fusion antibody, etc.) and/or a substance (e.g., monosaccharide, glucose, dextrose). The methods described herein can exploit the expression receptors expressed on the surface of the BBB (e.g., human insulin receptors) to shuttle the structure from peripheral blood into the CNS.

Structures

A structure can comprise an antibody. In some cases, the structure is the antibody itself. In other cases, the structure is a fusion antibody, or a fragment of an antibody. The structure may also comprise non-antibody constituents, such as peptides or nucleic acid (E.g., DNA, RNA, siRNA, etc.). An antibody can generally refer to an immunoglobulin whether naturally produced, or partially- or wholly-synthetically produced. An antibody can include any polypeptide or protein comprising a binding domain which is identical, or is homologous to, an antigen-binding domain. Complementary determining region (CDR) grafted antibodies can be contemplated by this term. An antibody can be understood to mean one or more fragments of an antibody that retain the ability to specifically bind to an antigen. Non-limiting examples of such antibodies can include (i) a Fab fragment, a monovalent fragment comprising the variable region of the light chain (VL), variable region of the heavy chain (VH), constant region of the light chain (CL) and first constant region of the heavy chain (CH1) domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment, which comprises a VH domain; and (vi) an isolated complementarity determining region (CDR). Furthermore, although the two domains of the Fv fragment, VL and VH, can be coded for by separate genes, they can be joined, by a synthetic linker that can enable them to be made as a single protein chain in which the VL and VH regions pair to form monovalent molecules (known as single chain Fv (scFv)). Such single chain antibodies can be intended to be encompassed within the term antibody. Any VH and VL sequences of specific scFv can be linked to human immunoglobulin constant region cDNA or genomic sequences. VH and VL can also be used in the generation of Fab, Fv or other fragments of immunoglobulins using either protein chemistry or recombinant DNA technology. Single chain antibodies can also include diabodies.

An antibody can resemble a native antibody. A native antibody or native immunoglobulins can generally be heterotetrameric glycoproteins of about 150,000 Daltons, comprising two identical light (L) chains and two identical heavy (H) chains. Each light chain can be linked to a heavy chain by one covalent disulfide bond, while the number of disulfide linkages can vary among the heavy chains of different immunoglobulin isotypes. Each heavy and light chain can have regularly spaced intrachain disulfide bridges. Each heavy chain can have at one end a variable domain ("VH") followed by a number of constant domains ("CH"). Each light chain can have a variable domain at one end ("VL") and a constant domain ("CL") at its other end; the constant domain of the light chain can be aligned with the first constant domain of the heavy chain, and the light-chain variable domain can be aligned with the variable domain of the heavy chain. Particular amino acid (AA) residues can form an interface between the light- and heavy-chain variable domains.

Antibodies can comprise a variable domain, which can generally refer to protein domains that differ extensively in sequence among family members (e.g. among different isoforms, or in different species). A variable domain can refer to the variable domains of antibodies that can be used in the binding and specificity of each particular antibody for its particular antigen. However, the variability may not be evenly distributed throughout the variable domains of antibodies. It can be concentrated in three segments called hypervariable regions both in the light chain and the heavy chain variable domains. The more highly conserved portions of variable domains can be called the framework region (i.e., FR). The variable domains of unmodified heavy and light chains can each comprise four FRs (FR1, FR2, FR3 and FR4, respectively), largely adopting a β-sheet configuration, connected by three hypervariable regions, which can form loops connecting, and in some cases forming part of, the β-sheet structure. The hypervariable regions in each chain can be held together in close proximity by the FRs and, with the hypervariable regions from the other chain, contribute to the formation of the antigen-binding site of antibodies. The constant domains may not be involved directly in binding an antibody to an antigen, but can exhibit various effector functions, such as participation of the antibody in antibody-dependent cellular toxicity. A variable domain can comprise about 50%, 60%, 70%, 80%, 90%, or 100% homology to a wild-type variable domain.

An antibody can comprise a variable framework region (i.e., VFR) which can refer to framework residues that form a part of the antigen binding pocket or groove and/or that may contact antigen. In some embodiments, the framework residues can form a loop that is a part of the antigen binding pocket or groove. The amino acids residues in the loop may or may not contact the antigen. The loop amino acids of a VFR can be determined by inspection of the three-dimensional structure of an antibody, antibody heavy chain, or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g. structural positions) can be less diversified. The three dimensional structure of the antibody variable domain can be derived from a crystal structure or protein modeling. In some embodiments, the VFR can comprise amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3. The VFR can form a loop that is well positioned to make contact with a target antigen or form a part of the antigen binding pocket.

An antibody can comprise an immunoglobulin chain. Immunoglobulins can be assigned to different classes, depending on the amino acid sequence of the constant domain of their heavy chains. There are five major classes of immunoglobulins: IgA, IgD, IgE, IgG, and IgM, and several of these can be further divided into subclasses (isotypes), e.g., IgG1, IgG2, IgG3, IgG4, IgA, and IgA2. The heavy-chain constant domains (Fc) that correspond to the different classes of immunoglobulins can be called α, δ, ε, γ, and μ, respectively. The subunit structures and three-dimensional configurations of different classes of immunoglobulins are well known. The light chains of antibodies (immunoglobulins) from any vertebrate species can be assigned to one of two clearly distinct types, called kappa or ("κ") and lambda or ("λ"), based on the amino acid sequences of their constant domains. Polypeptide, peptide, and protein can be used interchangeably to refer to a polymer of amino acid residues. The terms can apply to naturally occurring amino acid polymers as well as amino acid polymers in which one or more amino acid residues is a non-naturally occurring amino acid (e.g., an amino acid analog). As used herein, the terms can encompass amino acid chains of any length, including full length proteins (i.e., antigens), wherein the amino acid residues are linked by covalent peptide bonds.

In some instances, two or more antibody fragments can be present in a single polypeptide chain. In some instances, the antibody fragments can comprise a VH, a VL, or both a VH and VL domain of an antibody. When both domains are being present in a single polypeptide chain, the antibody can be referred to as a single-chain Fv (i.e., scFv) antibody. The antibody can comprise a polypeptide linker between the VH and VL domains which can enable the scFv to form the desired structure for antigen binding.

A structure can selectively bind an antigen (e.g., a receptor extracellular domain). A structure can selectively bind, or specifically bind a target antigen with a dissociation constant (Kd) that is about $10^{-6}$ Molar (M), $10^{-7}$ M, $10^{-8}$ M, $10^{-9}$ M, $10^{-10}$ M, $10^{-11}$ M, $10^{-12}$ M or lower. In some instances, A structure can selectively bind, or specifically bind a target antigen with a dissociation constant (Kd) that is about $10^{-12}$M, $10^{-11}$ M, $10^{-10}$ M, $10^{-9}$ M, $10^{-8}$ M, $10^{-7}$ M, $10^{-6}$ M or higher. A structure can bind an antigen allosterically, reversibly, or irreversibly.

An antibody can comprise a F(ab')2 and/or Fab' moiety. These moieties of the antibody can be produced by treating immunoglobulin with a protease such as pepsin and/or papain, and can include an antibody fragment generated by digesting immunoglobulin near the disulfide bonds existing between the hinge regions in each of the two H chains. For example, papain can cleave IgG upstream of the disulfide bonds existing between the hinge regions in each of the two H chains to generate two homologous antibody fragments in which an L chain comprised of VL (L chain variable region) and CL (L chain constant region), and an H chain fragment comprised of VH (H chain variable region) and CHγ1 (γ1 region in the constant region of H chain) can be connected at their C terminal regions through a disulfide bond. Each of these two homologous antibody fragments can be called Fab'. Pepsin can cleave IgG downstream of the disulfide bonds existing between the hinge regions in each of the two H chains to generate an antibody fragment slightly larger than the fragment in which the two Fab' are connected at the hinge region. This antibody fragment can be called F(ab')2.

An antibody can comprise a Fab fragment that can comprise the constant domain of the light chain and the first constant domain (CH1) of the heavy chain. Fab' fragments can differ from Fab fragments by the addition of a few residues at the carboxyl terminus of the heavy chain CH1 domain including one or more cysteine(s) from the antibody hinge region. Fab'-SH can be the designation herein for Fab' in which the cysteine residue(s) of the constant domains bear a free thiol group. F(ab')2 antibody fragments can be produced as pairs of Fab' fragments which have hinge cysteines between them. Other chemical couplings of antibody fragments can be performed (e.g., crosslinking).

The Fv portion of an antibody can generally refer to the minimum antibody fragment which comprises a complete antigen-recognition and antigen-binding site. This region can comprise a dimer of one heavy chain and one light chain variable domain in tight, non-covalent association. It is in this configuration that the three hypervariable regions of each variable domain can interact to define an antigen-binding site on the surface of the VH-VL dimer. Collectively, the six hypervariable regions can confer antigen-binding specificity to the antibody. However, even a single variable domain (or half of an Fv comprising only three hypervariable regions specific for an antigen) can recognize and bind antigen, although at a lower affinity than the entire binding site.

An antibody can comprise a hypervariable region. A hypervariable region can refer to the amino acid residues of an antibody which can be responsible for antigen-binding. The hypervariable region can comprise amino acid residues from three "complementarity determining regions" or "CDRs", which can directly bind, in a complementary manner, to an antigen and can be known as CDR1, CDR2, and CDR3 respectively. In the light chain variable domain, the CDRs can typically correspond to approximately residues 24-34 (CDRL1), 50-56 (CDRL2) and 89-97 (CDRL3), and in the heavy chain variable domain the CDRs can typically correspond to approximately residues 31-35 (CDRH1), 50-65 (CDRH2) and 95-102 (CDRH3); and/or those residues from a hypervariable loop (i.e. residues 26-32 (L1), 50-52 (L2) and 91-96 (L3) in the light chain variable domain and 26-32 (H1), 53-55 (H2) and 96-101 (H3) in the heavy chain variable domain.

An antibody may be chimeric. A chimeric antibody can be an antibody derived from a combination of different mammalian sources. The mammal may be, for example, a rabbit, a mouse, a rat, a goat, or a human. The combination of different mammals can include combinations of fragments from human and mouse sources. A chimeric antibody (e.g. HIR monoclonal antibody (HIRMAb), HIRAb, etc.) can comprise enough human sequence that it is not significantly immunogenic when administered to humans. For example, a chimeric HIRMAb can comprise about 80% human sequence and about 20% mouse sequence, or about 85% human sequence and about 15% mouse sequence, or about 90% human sequence and about 10% mouse sequence, or about 95% human sequence and 5% mouse sequence, or greater than about 95% human sequence and less than about 5% mouse sequence. A more highly humanized form of the HIRAb can also be engineered, and the humanized HIRMAb can have activity comparable to the murine HIRMAb.

An antibody can be a monoclonal antibody (MAb). An antibody can be a chimeric human-mouse antibody derived by humanization of a mouse monoclonal antibody. Such antibodies can be obtained from e.g., transgenic mice that have been "engineered" to produce specific human antibodies in response to antigenic challenge. In this technique, elements of the human heavy and light chain locus can be introduced into strains of mice derived from embryonic stem cell lines that comprise targeted disruptions of the endogenous heavy chain and light chain loci. The transgenic mice can synthesize human antibodies specific for human antigens, and the mice can be used to produce human antibody-secreting hybridomas.

Agent Component of the Structure

A structure (e.g., fusion antibody) can comprise two components. One component can comprise a polypeptide, immunoglobulin or antibody (e.g., monoclonal antibody (mAB)), or fragment thereof. One component can comprise an agent, such as a polypeptide, see, e.g., U.S. application Ser. No. 11/245,546, first inventor: Pardridge, "Fusion Proteins for Blood-Brain Barrier Delivery."

The agent component of the structure can comprise a polypeptide sequence that encodes for a protein. The polypeptide sequence can be more than 1, more than 5, more than 10, more than 20, more than 30, more than 40, more than 50, more than 100, more than 150, more than 200, more than 250, more than 300, more than 350, more than 400, more than 450, more than 500, more than 550, more than 600, more than 650, more than 700, more than 750, more than 800, more than 850, more than 900, more than 1000, more than 1100, more than 1200, more than 1300, more than 1400, more than 1500, more than 1600, more than 1700 amino acids in length. The polypeptide sequence can be less than 5, less than 10, less than 20, less than 30, less than 40, less than 50, less than 100, less than 150, less than 200, less than 250, less than 300, less than 350, less than 400, less than 450, less than 500, less than 550, less than 600, less than 650, less than 700, less than 750, less than 800, less than 850, less than 900, less than 1000, less than 1100, less than 1200, less than 1300, less than 1400, less than 1500, less than 1600, less than 1700 amino acids in length.

The polypeptide sequence component of the structure can comprise a polypeptide sequence encoding a receptor extracellular domain. For example, the receptor extracellular domain can be a cytokine. Examples of receptor extracellular domains can include, but are not limited to, a cytokine receptor (e.g., IL-2 receptor), chemokine receptor (e.g., CXCR4, CCR5), tumor necrosis factor (TNF)-α receptor (e.g., CD120a, CD120b, CD134, CD40, FAS, CD27, RANK, TNFRSF13C, TNRSF14, TNRSF17, TNRSF18, TNRSF19, etc.), TNF-related apoptosis inducing ligand (TRAIL) receptor, TNF-like weak inducer of apoptosis (TWEAK) receptor, IL-6 receptor, vascular endothelial growth factor receptor, ephrin receptor. Receptor ECDs can bind their cognate ligand. GenBank accession numbers for some of the amino acid sequences of the above-mentioned receptors are provided in table 1 below.

TABLE 1

GenBank Accession Numbers for Receptors from Various Species

| Receptor | Human | Mouse | Rat | Pig |
|---|---|---|---|---|
| TNF-α | NP_001056 | AY541589.1 | AAK53563 | NP_999134 |
| TRAIL | NP_003835 | NP_064671 | ACL51000.1 | XP_001926758.1 |
| TWEAK | NP_057723.1 | NP_038777.1 | NP_851600.1 | NP_001136311.1 |
| IL-6 | NP_000556.1 | NP_034689.2 | NP_058716.2 | NP_999568.1 |
| VEGF | NP_002010.2 | NP_034358.2 | NP_062179.1 | XP_001925775.1 |
| Ephrin | NP_005223.4 | NP_076069.2 | NP_001101328.1 | NP_001128439.1 |

In some instances, the polypeptide sequence component of the structure can comprise a protein suitable for introduction into the CNS such as a neurotrophin. Examples of proteins suitable for introduction into the CNS can include, but are not limited to, glial-cell derived neurotrophic factor (GDNF), brain derived neurotrophic factor (BDNF), nerve growth factor (NGF), neurotrophin-4/5, neutrophin-3, epidermal growth factor (EGF), transforming growth factor-α (TGF-α), neuturin, platelet-derived growth factor (PDGF), artemin, bone morphogenic protein (BMP), hepatocyte growth factor (HGF), erythropoietin (EPO), hereguin, neuregulin, granulocyte-colony stimulating factor (CSF), saposin, leukemia inhibitory factor (LIF), midkine, pleiotrophin, netrins, semaphorins, stem cell factor (SCF), and the like.

In some instances, the polypeptide sequence component of the structure can comprise an enzyme such as a lysosomal enzyme (e.g., acid hyrolase enzyme). Examples of enzymes can include, but are not limited to, alpha-L-iduronidase (IDUA), iduronate2 sulfatase (IDS), aryl sulfatase (ASA) (e.g., ASA A, ASA B).

In some instances, the polypeptide sequence component can comprise a polypeptide involved in a lysosomal storage disorder (LSD). A LSD can be an inherited metabolic disorder that can result from the deficiency of enzymes required to break down mucopolysaccharides (e.g., lipids and glycoproteins). Examples of LSDs can include, but are not limited to, alpha-mannosidosis, aspartylglucosoaminuria, cystinosis, Danon disease, Fabry disease, fucosidosis, Gaucher disease, Krabbe disease, lysosomal acid lipase deficiency, Hurler syndrome, Hunter syndrom, Sanfilippo syndrome, Niemann-Pick disease, neuronal ceroid lipofuscinoses, pyncodysostosis, Schindler disease, and Tay-Sachs.

An agent can be a toxin. Examples of toxins can include hemotoxin, phototoxin, exotoxins, endotoxins, toxoids, venoms, botulism toxin, necrotoxins, neurotoxins, and cytotoxins.

An agent can be a small molecule binding domain. Examples of small molecule binding domains can include avidin or streptavidin, which bind biotin, biotinylated molecules, biotinylated dyes (e.g., Cy3, Cy5) or other fluorescent molecules, biotinylated radiopharmaceuticals, or albumin, which binds drugs and free fatty acids, nanoparticles (e.g., fluorescent nanoparticles), and quantum dots.

An agent can be a tag. Examples of tags can include maltose binding protein (MBP), chitin binding protein (CBP), glutathione-S-transferase (GST), poly-hisitidine tag, V5, c-myc, fluorescent protein (e.g., green fluorescent protein), quantum dot, HA, FLAG, calmodulin tag, and SBP-tag.

In some instances the polypeptide sequence can be fused to the N-terminus of the immunoglobulin heavy chain and/or light chain. In some instances the polypeptide sequence can be fused to the C-terminus of the immunoglobulin heavy chain and/or light chain.

The polypeptide sequence component can comprise an amino acid sequence at least 60%, 70%, 80%, 85%, 90%, 95%, 97%, 99%, identical to a human, mouse, rat, or pig homologue of the polypeptide sequence. The polypeptide sequence component can comprise an amino acid sequence at most 60%, 70%, 80%, 85%, 90%, 95%, 97%, 99%, identical to a human, mouse, rat, or pig homologue of the polypeptide sequence.

The polypeptide sequence component of the structure can retain an average of at least about 5%, 10%, 15%, 18%, 20%, 25%, 30%, 35%, 40%, 40%, 45%, 50%, 60%, 70%, 80%, 90%, or 100% of its activity compared to their activity as a non-fused polypeptide. The polypeptide sequence component of the structure can retain an average of at most about 5%, 10%, 15%, 18%, 20%, 25%, 30%, 35%, 40%, 40%, 45%, 50%, 60%, 70%, 80%, 90%, or 100% of its activity compared to their activity as a non-fused polypeptide.

IDS Polypeptide Sequence Component of the Structure

A structure provided herein can comprise an agent such as iduronate-2 sulfatase (IDS). IDS (e.g., the human IDS sequence listed under GenBank Accession No. NP 000193) is a member of a family of sulfatases that may catalyze the hydrolysis or removal of 2-sulfate groups of the L-iduronate 2-sulfate units of dermatan sulfate, heparan sulfate, and heparin. IDS can be post-translationally modified resulting in IDS enzyme activity. The activity of the IDS enzyme can be activated following the conversion of Cys-59 to a formylglycine residue by a sulfatase modifying factor type 1 (SUMF1), which can also be called the formylglycine generating enzyme (FGE). Dermatan sulfate, heparan sulfate and heparin are variably sulfated glycosaminoglycans, which are long, unbranched polysaccharides made up of a repeating disaccharide unit. L-iduronate (or L-iduronic acid) is a major component of dermatan sulfate and heparin. It may also be present in heparan sulfate. An IDS deficiency can include one or more conditions known as Hunter's syndrome, Hunter's disease, or mucopolysaccharidosis type II. The IDS deficiency can be characterized by the buildup of heparan sulfate and dermatan sulfate that occurs in the body (the heart, liver, brain etc.). An IDS fusion antibody can treat IDS deficiency.

In some embodiments, the agent sequence component of the fusion antibody can be a polypeptide sequence comprising at least about 50%, 60%, 70%, 80%, 90%, or 100% sequence homology to an IDS polypeptide sequence (e.g., the human IDS sequence listed under GenBank Accession No. NP 000193, or SEQ ID NO: 5). In some embodiments, the polypeptide sequence component of the fusion antibody can be a polypeptide sequence comprising at most about 50%, 60%, 70%, 80%, 90%, or 100% sequence homology to an IDS polypeptide sequence (e.g., the human IDS sequence listed under GenBank Accession No. NP 000193, or SEQ ID NO: 5).

An IDS-fusion antibody can comprise a sequence with at least about 50%, 60%, 70%, 80%, 90%, or 100% sequence homology to an IDS-fusion antibody (e.g. SEQ ID 6, which is comprised of a 19 amino acid IgG signal peptide, the 443 amino acid HIRAb heavy chain (HC), a 2 amino acid linker (Ser-Ser), and the 525 amino acid human IDS minus the enzyme signal peptide). The predicted molecular weight of the heavy chain fusion protein, minus glycosylation, is 108,029 Da, with a predicted isoelectric point (pi) of 6.03). An IDS-fusion antibody can comprise a sequence at most about 50%, 60%, 70%, 80%, 90%, or 100% sequence homology to an IDS-fusion antibody (e.g. SEQ ID 6, which is comprised of a 19 amino acid IgG signal peptide, the 443 amino acid HIRMAb heavy chain (HC), a 2 amino acid linker (Ser-Ser), and the 525 amino acid human IDS minus the enzyme signal peptide. The predicted molecular weight of the heavy chain fusion protein, minus glycosylation, is 108,029 Da, with a predicted isoelectric point (pi) of 6.03).

Sequence variants of a canonical IDS sequence can be generated (e.g., by random mutagenesis of the entire sequence or specific subsequences corresponding to particular domains). Alternatively, site directed mutagenesis can be performed reiteratively while avoiding mutations to residues known to be critical to IDS function (e.g., Residues that may be critical to the function of IDS can include Arg 48, Ala 85, Pro 86, Ser 333, Trp 337, Ser 349, Arg 468, and Gln 531). Further, in generating multiple variants of an IDS sequence, mutation tolerance prediction programs can be used to greatly reduce the number of non-functional sequence variants that may be generated by strictly random mutagenesis. Various programs for predicting the effects of amino acid substitutions in a protein sequence on protein function can include SIFT, PolyPhen, PANTHER PSEC, PMUT, and TopoSNP).

IDS sequence variants can be screened for of IDS activity/retention of IDS activity by (e.g., 4-methylumbelliferyIa-L-iduronide-2-sulphate (4-MUS) fluorometric IDS assays). A very large number of operable IDS sequence variants can be obtained by generating and screening extremely diverse "libraries" of IDS sequence variants.

In some embodiments, an agent comprises a variant IDS polypeptide sequence. A variant IDS polypeptide sequence can retain at least about 10%, 20%, 30%, 40%, 50%, 60%, 70%, 80%, 90%, 95%, 99%, or 100% of its activity, compared to wild type. A variant IDS polypeptide sequence can retain at most about 10%, 20%, 30%, 40%, 50%, 60%, 70%, 80%, 90%, 95%, 99%, or 100% of its activity, compared to wild-type.

A polypeptide sequence component can be post-translationally modified. In some instances, modification of IDS can occur by a sulfatase modifying factor type 1 (SUMF1). The post-translational modification can comprise a cysteine to formylglycine conversion. In some instances, the post-translational modification can comprise a formylglycine residue.

IDUA Polypeptide Sequence Component of the Structure

In some cases, a structure can comprise an agent such as alpha-L-iduronidase (IDUA). IDUA can be involved in type I mucopolysaccharidosis (MPS). Type I MPS, which can also be known as Hurler's syndrome, is an inherited metabolic disease caused by a defect in the enzyme a-L-iduronidase (IDUA). IDUA can function to degrade mucopolysaccharides. IDUA can catalyze the hydrolysis of unsulfated alpha-L-iduronosidic linkages in dermatan sulfate. An insufficient level of IDUA causes a pathological buildup of heparan sulfate and dermatan sulfate in organs (e.g., heart, liver) and central nervous system. Symptoms can include neurodegeneration and mental retardation and may appear during childhood. Early death can occur due to organ damage. Recombinant IDUA does not cross the blood brain barrier (BBB), and therefore has little impact on the effects of the disease in the central nervous system (CNS). An IDUA fusion antibody may be able to treat Hurler's syndrome.

In some embodiments, the agent component of the structure can comprise a polypeptide sequence comprising at least about 50%, 60%, 70%, 80%, 90%, or 100% sequence homology to an IDUA polypeptide sequence (e.g., e.g., the human IDUA sequence listed under GenBank Accession No. NP 000194. Or SEQ ID NO:3). In some embodiments, the agent component of the structure can comprise a polypeptide sequence comprising at most about 50%, 60%, 70%, 80%, 90%, or 100% sequence homology to an IDUA polypeptide sequence (e.g., e.g., the human IDUA sequence listed under GenBank Accession No. NP 000194. Or SEQ ID NO:3).

In some instances, an IDUA-fusion antibody can comprise a sequence at least about 50%, 60%, 70%, 80%, 90%, or 100% sequence homology to an IDUA-fusion antibody (e.g. SEQ ID 4 which is comprised of a 19 amino acid IgG signal peptide, the 443 amino acid HIR Ab HC, a 2 amino acid linker (Ser-Ser), and the 627 amino acid human IDUA minus the enzyme signal peptide. The predicted molecular weight of the heavy chain fusion protein, minus glycosylation, is 118,836 Da, with a predicted isoelectric point (pI) of 8.89.) In some instances, an IDUA-fusion antibody can comprise a sequence at most about 50%, 60%, 70%, 80%, 90%, or 100% sequence homology to an IDUA-fusion antibody (e.g. SEQ ID 4 which is comprised of a 19 amino acid IgG signal peptide, the 443 amino acid HIR Ab HC, a 2 amino acid linker (Ser-Ser), and the 627 amino acid human IDUA minus the enzyme signal peptide. The predicted molecular weight of the heavy chain fusion protein, minus glycosylation, is 118,836 Da, with a predicted isoelectric point (pI) of 8.89.)

Sequence variants of a canonical IDUA sequence can be generated (e.g., by random mutagenesis of the entire sequence or specific subsequences corresponding to particular domains). Alternatively, site directed mutagenesis can be performed reiteratively while avoiding mutations to residues known to be critical to IDUA function (e.g., Gly 51, Ala 75, Ala 160, Glu 182, Gly 208, Leu 218, Asp 315, Ala 327, Asp 349, Thr 366, Thr 388, Arg 489, Arg 628, Ala 79, His 82, Glu 178, Ser 260, Leu 346, Asn 350, Thr 364, Leu 490, Pro 496, Pro 533, Arg 619, Arg 89, Cys 205, His 240, Ala 319, Gln 380, Arg 383, and Arg 492). Further, in generating multiple variants of an IDUA sequence, mutation tolerance prediction programs can be used to greatly reduce the number of non-functional sequence variants that may be generated by strictly random mutagenesis. Various programs for predicting the effects of amino acid substitutions in a protein sequence on protein function can include SIFT, PolyPhen, PANTHER PSEC, PMUT, and TopoSNP).

IDUA sequence variants can be screened for of IDUA activity/retention of IDUA activity (e.g., by 4-methylumbelliferyl a-L-iduronide (MUBI) fluorometric IDUA assays). A very large number of operable IDUA sequence variants can be obtained by generating and screening extremely diverse "libraries" of IDUA sequence variants.

In some embodiments, the IDUA polypeptide sequence can retain at least about 10%, 20%, 30%, 40%, 50%, 60%, 70%, 80%, 90%, 95%, 99%, or 100% of its activity, compared to wild-type. In some embodiments, the IDUA polypeptide sequence can retain at least about 10%, 20%, 30%, 40%, 50%, 60%, 70%, 80%, 90%, 95%, 99%, or 100% of its activity, compared to wild-type.

Antibody Component of the Structure

The structure can comprise an antibody component. The antibody component can be a polypeptide sequence. The antibody component can be an antibody that binds a BBB receptor. The antibody can be a monoclonal antibody. The antibody can be a monovalent antibody. The antibody can be a divalent antibody. The antibody can comprise a polypeptide sequence encoding an immunoglobulin. The antibody can comprise both a HC and a LC of an immunoglobulin.

When the antibody component comprises a heavy chain, the heavy chain of can be at least about 50, 60, 70, 80, 90, or 100% identical to a heavy chain immunoglobulin (e.g., SEQ ID NO: 1) When the antibody component comprises a heavy chain, the heavy chain of can be at most about 50, 60, 70, 80, 90, or 100% identical to a heavy chain immunoglobulin (e.g., SEQ ID NO: 1) When the antibody component comprises a light chain, the light chain can be at least about 50, 60, 70, 80, 90, or 100% identical to a light chain immunoglobulin (e.g., SEQ ID NO: 2) When the antibody component comprises a light chain, the light chain can be at most about 50, 60, 70, 80, 90, or 100% identical to a light chain immunoglobulin (e.g., SEQ ID NO: 2)

In some instances, an antibody component can comprise an immunoglobulin. Immunoglobulins can be divided into isotypes such as IgA, IgD, IgE, IgG, and IgM. IgA isotypes can be found in muscosal areas, saliva, tears, and breast milk. IgD isotypes can be receptors on B cells, and can activate basophils and mast cells for production of antimicrobial molecules. IgE isotypes can bind allergans and be involved in histamine release. IgG isotypes can provide immunity against invasive pathogens. IgM isotypes can be expressed on B cells.

The antibody component can bind to a receptor expressed on the surface of the BBB. Examples of BBB receptors can include, but are not limited to insulin receptors, transferrin receptors, and a lipoprotein receptors. In some embodiments the fusion antibody component is an antibody that binds the human insulin receptor (HIR). The antibody component can bind the ECD of the BBB receptors.

BBB receptors can allow the transport of structures from the blood to the brain. BBB receptors that allow transport of structures can be called transporters. Endogenous BBB receptor-mediated transport systems can include, but are not limited to, those that transport insulin, transferrin, insulin-like growth factors 1 and 2 (IGF1 and IGF2), leptin, and lipoproteins. In some embodiments, an antibody can be capable of crossing the BBB via the endogenous insulin BBB receptor-mediated transport system. Certain insulin receptor ECD-specific antibodies may mimic the endogenous ligand and thereby traverse a plasma membrane barrier via transport on the specific receptor system. In certain embodiments, a fusion antibody can bind an exofacial epitope on the human BBB HIR and this binding can enable the fusion antibody to traverse the BBB via a transport reaction that is mediated by the human BBB insulin receptor.

Insulin receptors and their extracellular, insulin binding domain (ECD) have been characterized structurally and functionally. See, e.g., Yip et al (2003), "*J Biol. Chem,* 278(30):27329-27332; and Whittaker et al. (2005), *J Biol Chem,* 280(22):20932-20936. The amino acid and nucleotide sequences of the human insulin receptor can be found under GenBank accession No. NM_000208.

The antibody component of the structure can be glycosylated or non-glycosylated. If the antibody is glycosylated, any pattern of glycosylation that does not significantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody can be glycosylated in the pattern produced by a transfected Chinese hamster ovary (CHO) cell.

The antibody component of structure can comprise an antibody component capable of crossing the BBB, wherein the antibody component can be capable of crossing the blood brain barrier with about 5%, 10%, 15%, 18%, 20%, 25%, 30%, 35%, 40%, 40%, 45%, 50%, 60%, 70%, 80%, 90%, or 100% of the same kinetics and/or thermodynamics compared to as if the antibody component was not fused to the structure. The antibody component of structure can comprise an antibody component capable of crossing the BBB, wherein the antibody component can be capable of crossing the blood brain barrier with more than about 5%, 10%, 15%, 18%, 20%, 25%, 30%, 35%, 40%, 40%, 45%, 50%, 60%, 70%, 80%, 90%, or 100% of the same kinetics and/or thermodynamics compared to as if the antibody component was not fused to the structure. The antibody component of structure can comprise an antibody component capable of crossing the BBB, wherein the antibody component can be capable of crossing the blood brain barrier with less than about 5%, 10%, 15%, 18%, 20%, 25%, 30%, 35%, 40%, 40%, 45%, 50%, 60%, 70%, 80%, 90%, or 100% of the same kinetics and/or thermodynamics compared to as if the antibody component was not fused to the structure.

The antibody component can selectively bind an antigen (e.g., a receptor extracellular domain). The antibody component can selectively bind, or specifically bind a target antigen with a dissociation constant (Kd) that is about $10^{-6}$ Molar (M), $10^{-7}$ M, $10^{-8}$ M, $10^{-9}$ M, $10^{-10}$ M, $10^{-11}$ M, $10^{-12}$ M or lower. In some instances, the antibody component can selectively bind, or specifically bind a target antigen with a dissociation constant (Kd) that is about $10^{-12}$ M, $10^{-11}$ M, $10^{-10}$ M, $10^{-9}$ M, $10^{-8}$ M, $10^{-7}$ M, $10^{-6}$ M or higher. A structure can bind an antigen allosterically, reversibly, or irreversibly.

Linkages Between the Agent and Antibody of the Structure

In the structures of the disclosure, the covalent linkage between the antibody component and the agent may be to the carboxy or amino terminal of the BBB receptor antibody heavy chain immunoglobulin or light chain immunoglobulin as long as the linkage allows the structure to bind to the ECD of the BBB receptor and cross the blood brain barrier, and allows the fused agent to retain a therapeutically useful portion of its activity. In certain embodiments, the covalent link can be between a HC of the antibody and the agent. In other embodiments, the covalent link can be between a LC of the antibody and the agent. Any suitable linkage may be used (e.g., carboxy terminus of light chain to amino terminus of the agent, carboxy terminus of heavy chain to amino terminus of agent, amino terminus of light chain to carboxy terminus of agent, or amino terminus of heavy chain to carboxy terminus of agent). The linkage can be from the carboxy terminus of the HC to the amino terminus of the agent.

The linkage between terminal amino acids can be accomplished by an intervening peptide linker sequence. The peptide linker sequence may be 1, 2, 3, 4, 5, 6, 7, 8, 9, 10, or more amino acids in length. In some embodiments, a two amino acid linker is used. In some embodiments, the linker can comprise the sequence serine-serine (S-S), serine-serine-serine (S-S-S), or serine-serine-methionine (S-S-M). The peptide linker sequence may include a protease cleavage site (e.g. TEV).

Fusion Antibodies Variations

A structure can be a fusion antibody comprising an antibody component and an agent (e.g., polypeptide sequence). Fusion antibodies can comprise proteins having a conservative amino acid change, in the antibody component and/or the polypeptide sequence component of the fusion antibody, compared with an amino acid sequence disclosed herein. Among the common amino acids, for example, a "conservative amino acid substitution" can be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins. Accordingly, the BLOSUM62 substitution frequencies can be used to define conservative amino acid substitutions that may be introduced into the amino acid sequences of the fusion antibody. Although it is possible to design amino acid substitutions based solely upon chemical properties, the language "conservative amino acid substitution" can refer to a substitution represented by a BLOSUM62 value of greater than −1. For example, an amino acid substitution can be conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the disclosure.

A vast number of sequence variants of antibodies or agents to be readily generated (e.g., in vitro) and screened for binding to a target antigen such as the ECD of the human insulin receptor or for binding to a ligand of the polypeptide sequence. Screening may be performed by ultra high throughput screening of antibody sequence variants. In order to isolate sequence variants, random mutagenesis of the entire sequence or specific subsequences corresponding to particular domains may be performed. Alternatively, site directed mutagenesis can be performed reiteratively while avoiding mutations to residues known to be critical to BBB receptor or polypeptide sequence ligand binding. In generating multiple variants of an agent, mutation tolerance prediction programs can be used to greatly reduce the number of non-functional sequence variants that would be generated by strictly random mutagenesis. Various programs for predicting the effects of amino acid substitutions in a protein sequence on protein function (e.g., SIFT, PolyPhen, PANTHER PSEC, PMUT, and TopoSNP) can be used. A very large number of operable decoy receptor ECD sequence variants can be obtained by generating and screening extremely diverse "libraries" of polypeptide sequence (e.g., human TNF-α receptor ECD sequences) sequence variants.

Agonist and Antagonist Activity of Fusion Antibodies

In some instances, a fusion antibody can act as an agonist. Agonists can bind to antigens and activate them. A fusion antibody agonist can increase the activity of the antigen to which it binds (e.g., human insulin receptor) more than 2-fold, 3-fold, 4-fold, 5-fold, 6-fold, 7-fold, 8-fold, 9-fold, 10-fold, 15-fold, 20 or more fold. A fusion antibody agonist can increase the activity of the antigen to which it binds (e.g., human insulin receptor) less than 2-fold, 3-fold, 4-fold, 5-fold, 6-fold, 7-fold, 8-fold, 9-fold, 10-fold, 15-fold, 20 or more fold.

In some instances, a fusion antibody can act as an antagonist. Antagonists can bind to antigens and inactivate them. A fusion antibody antagonist can inhibit the activity of the antigen to which it binds (e.g., human insulin receptor) more than 2-fold, 3-fold, 4-fold, 5-fold, 6-fold, 7-fold, 8-fold, 9-fold, 10-fold, 15-fold, 20 or more fold. A fusion antibody antagonist can inhibit the activity of the antigen to which it binds (e.g., human insulin receptor) less than 2-fold, 3-fold, 4-fold, 5-fold, 6-fold, 7-fold, 8-fold, 9-fold, 10-fold, 15-fold, 20 or more fold.

Compositions of Structures and Substances

The disclosure provides for compositions comprising structures and substances. A substance can be a monosaccharide. A monosaccharide can be glucose. Monosaccharides can include fructose, galactose, xylose, and ribose. Monosaccharides are simple sugars that can form a basic building block for complex carbohydrates (e.g., disaccharides such as sucrose, and polysaccharides such as cellulose). Monosaccharides can be categorized by the number of carbons they comprise. For example, a diose comprises 2 carbons, a triose comprises 3 carbons, a tetrose comprise 4 carbons, etc. Glucose can comprise 6 carbons can be referred to as a hexose. Monosaccharides can be linear. Monosaccharides can be cyclic (i.e., can be referred to as furanoses, pyranoses). A monosaccharide can be linear in one form, and cyclic in another form. Glucose may cyclize from its linear structure to form glucofuranose (if the cyclization forms a 5 membered ring), or glucopyranose (if the cyclization forms a 6 membered ring).

Monosaccharides can be stereoisomers. Stereoisomers can comprise the same molecular formula and order of atoms in the molecule, but can differ in the three dimensional orientation of the atoms in space. Depending on the length of a monosaccharide and the number of chiral centers, a monosaccharide may comprise more than two stereoisomers. Stereoisomers can be referred to as dextrorotatory (D) or levorotatory (L). Glucose has two stereoisomers: a D and L isomer. D-glucose can be metabolized by cells. L-glucose may not be metabolized by cells.

D-Glucose can also be known as dextrose. Glucose and/or dextrose can interact with amino acids of proteins (i.e., glycation, glycosylation). Glycation can inhibit the activity of proteins. Glycosylation can be a regulated process and can be important in proper protein function.

Glucose and/or dextrose can be absorbed into the bloodstream during digestion. It can be a primary source of energy. The breakdown of glucose and/or dextrose can be referred to as glycolysis. Glycolysis can occur through enzymatic pathways in the citric acid cycle. Glycolysis can result in adenosine triphosphate (ATP) which can provide energy to cells.

Glucose and/or dextrose can be easily dissolved in polar solutions such as water and acetic acid. Solutions of glucose can be colorless. Solutions of glucose and/or dextrose can comprise isomers of glucose and/or dextrose. For example, linear glucose in solution can spontaneously isomerize to a cyclized form. Glucose and/or dextrose can exist in a solid form. In solid form, glucose and/or dextrose can be crystallized into, for example, $\alpha$-glucopyranose, $\beta$-glucopyranose, and $\beta$-glucopyranose hydrate.

A substance can be a substance that can treat hypoglycemia, or prevent hypoglycemia. Such agents can include, for example, dextrose, glucose (e.g., insta-Glucose, BD Glucose), glucacon, diazoxide (e.g., Proglycem, Hyperstat).

A substance can be a substance that treats hyperglycemia. Such agents can include, for example, insulin, Regular insulin (e.g., Humulin R, Novolin R), Insulin lispro (e.g., Humalog), Insulin aspart (e.g., Novolog), Insulin glulisine (e.g., Apidra), Prompt insulin zinc (e.g., Semilente), Isophane insulin, neutral protamine Hagedorn (e.g., Humulin N, Novolin N), Insulin zinc (e.g., Lente), extended insulin zinc insulin (e.g., Ultralente), Insulin glargine (e.g., Lantus), Insulin detemir (e.g., Levemir), Sulfonylurea (e.g., glyburide, glimepiride, glipizide, tolbutamide, aceothexamide, tolazamide, chlorpropamide, glimepiride, gliclazide, glycopyramide, gliquidone), biganides, Metformin (e.g., Glucophage), Phenformin, Buformin, Alpha-glucosidase inhibitor (e.g., acarbose, miglitol, voglibose), Thiazolidinediones (e.g., Pioglitazone, Rosiglitazone, troglizazone), meglitinides (e.g., repaglinide, nateglinide), glucacon-like peptides (e.g., exenatide, liraglutide, taspoglutide), dipeptidyl peptidase-4 inhibitors (e.g., vildagliptin, sitagliptin, saxagliptin, linagliptin, allogrliptin, septagliptin), and amylin agonist analogues A substance can be treat a CNS inflammatory condition and can include immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-$\alpha$ binding proteins (e.g., infliximab, etanercept, or adalimumab), abatacept, anakinra, interferon-$\beta$, interferon-$\alpha$, interleukin-2, allergy vaccines, antihistamines, antileukotrienes, beta-agonists, theophylline, anticholinergics, or any combination thereof.

A substance can be treat Multiple Sclerosis and can include Interferon $\beta$-1a, Interferon $\beta$-1b, glatiramer acetate (Copaxone®), mitoxantrone (Novantrone®), low dose naltrexone, Natalizumab (Tysabri®), Sativex®, Aimspro (Goats Serum), Trimesta (Oral Estriol), Laquinimod, FTY720 (Fingolimod), MBP8298, NeuroVax™, Tovaxin™, Revimmune, CHR-1103, BHT-3009, BG-12, Cladribine, daclizumab (Zenapax) Rituximab (Rituxan), cyclophosphamide, Campath, Fampridine-SR, MN-166, Temsirolimus, RPI-78M, or any combination thereof.

A substance can be treat Alzheimer's Disease or AIDS-related Dementia and can include Flurizan™ (MPC-7869, r flurbiprofen), memantine, galantamine, rivastigmine, donezipil, tacrine, A$\beta_{1-42}$ immunotherapy, resveratrol, (–)-epigallocatechin-3-gallate, statins, vitamin C, vitamin E, or any combination thereof.

A substance can be treat Thromboembolic Disorders and can include thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, BIBR 1048, or any combination thereof.

Compositions, or kits, of the disclosure can comprise the structure of the disclosure and a substance. The substance can be glucose. The composition can comprise a substance (e.g., glucose and/or dextrose) at a concentration of about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the composition (w/v or v/v). The composition can comprise glucose and/or dextrose at a concentration of at least about 5% (w/v or v/v), or at most about 5% (w/v or v/v). The composition can comprise a substance (e.g., glucose and/or dextrose) at a concentration of at least about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the composition (w/v or v/v). The composition can comprise a substance (e.g., glucose and/or dextrose) at a concentration of at most about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the composition (w/v or v/v).

The composition, or kit, can comprise between about 0.1 mg/kg and 0.5 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition, or kit, can comprise between about 0.5 mg/kg and 1 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 1 mg/kg and 2 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 2 mg/kg and 3 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of The substance. The composition can comprise glucose and/or dextrose at a concentration of about 5% (w/v or v/v).

The composition can comprise between about 3 mg/kg and 4 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 4 mg/kg and 5 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 5 mg/kg and 7 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 7 mg/kg and 10 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 10 mg/kg and 13 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 13 mg/kg and 16 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 16 mg/kg and 20 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 20 mg/kg and 25 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 25 mg/kg and 30 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 30 mg/kg and 35 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

The composition or kit can comprise between about 35 mg/kg and 40 mg/kg of the structure and about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more of the substance. The composition can comprise glucose and/or dextrose at a concentration of about 5% (w/v or v/v).

In some cases, a subject is treated with a substance (e.g., monosaccharide, glucose, dextrose, therapeutic) because the structure (e.g., fusion antibody, antibody, IDUA fusion antibody, IDS fusion antibody, anti-insulin antibody, etc.) causes a reduction in blood sugar or hypoglycemia at a particular dosage. For example, a dosage of greater than about 5 mg/kg, 10 mg/kg, 20 mg/kg, 30 mg/kg, 40 mg/kg, 50 mg/kg, etc., of structure may cause hypoglycemia or a reduction in blood sugar in a subject. In particular, a dosage of greater than about 30 mg/kg may cause hypoglycemia. See, e.g., Boado et al. (2012) Drug Metabolism and Disposition, vol. 40 (10):2021-2025. In some cases, a subject is monitored during or after administration of the structure in order to determine whether the particular dosage that is administered to the subject causes reduced blood sugar (or causes hypoglycemia). In such cases, the dosage of the structure may be adjusted to lessen the probability that the subject experiences a reduction in blood sugar or hypoglycemia. The adjusted dosage may avoid, or reduce, the possibility of administering a substance to treat hypoglycemia.

In some cases, a subject is treated with a substance (e.g., therapeutic) because the structure (e.g., fusion antibody, antibody, IDUA fusion antibody, IDS fusion antibody, anti-insulin antibody, etc.) causes an increase in blood sugar or hyperglycemia at a particular dosage. For example, a dosage of greater than, or less than, about 5 mg/kg, 10 mg/kg, 20 mg/kg, 30 mg/kg, 40 mg/kg, 50 mg/kg, etc., of structure may cause hyperglycemia or an increase in blood sugar in a subject. In some cases, a subject is monitored during or after administration of the structure in order to determine whether the particular dosage that is administered to the subject causes increased blood sugar (or causes hyperglycemia). In such cases, the dosage of the structure may be adjusted to lessen the probability that the subject experiences a reduction in blood sugar or hyperglycemia.

Formulations

Pharmaceutical compositions can comprise one or more fusion antibodies and a pharmaceutically acceptable excipient. A pharmaceutical composition of the disclosure (e.g., a structure and/or a substance) can comprise a combination of any pharmaceutical compounds described herein with other chemical components, such as carriers, stabilizers, diluents, dispersing agents, suspending agents, thickening agents, and/or excipients. The pharmaceutical compositions can include at least one pharmaceutically acceptable carrier, diluent, or excipient and compounds described herein as free-base or pharmaceutically-acceptable salt form. The methods and pharmaceutical compositions described herein include the use crystalline forms (also known as polymorphs), and active metabolites of these compounds having the same type of activity. The compositions may comprise a binder, such as gum tragacanth, acacia, cornstarch, or gelatin; excipients, such as dicalcium phosphate. The compositions may comprise a disintegrating agent, such as corn starch, potato starch, alginic acid and the like. The compositions may comprise a lubricant, such as magnesium stearate, talc, silica, fats, and the like. The compositions may comprise a sweetening agent, such as sucrose, lactose or saccharin. The compositions may comprise a flavoring agent, such as peppermint, oil of wintergreen, or cherry flavoring.

The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration. Pharmaceutical compositions of the disclosure can include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration. The pharamaceutical composition can be modified depending on the route of administration.

The phrases pharmaceutically or pharmacologically acceptable can refer to molecular entities and compositions that do not produce an adverse, allergic or other untoward reaction when administered to an animal (e.g., a human), as appropriate. Pharmaceutically acceptable carrier can include any and all solvents, dispersion media, coatings, antibacterial and antifungal agents, isotonic and absorption delaying agents and the like. A pharmaceutically acceptable carrier or pharmaceutically acceptable excipient can refer to any carrier that does not itself induce the production of antibodies harmful to the individual receiving the composition. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions may be provided in liquid form, and formulated in saline based aqueous solution of varying pH (5-8), with or without detergents such as polysorbate-80 at 0.0001-1%, or carbohydrate additives, such mannitol, sorbitol, trehalose or monosaccharide. Commonly used buffers can include histidine, acetate, phosphate, or citrate.

In some cases, the composition comprises saline, e.g., NaCl, at a concentration such as at least about 0.05 M, 0.06M, 0.07 M, 0.08 M, 0.09 M, 0.10 M, 0.11 M, 0.12 M, 0.13 M, 0.14 M, 0.15 M, 0.16 M, 0.17 M, 0.18 M, 0.19 M, 0.20 M, 0.21 M, 0.22 M, 0.23 M, 0.24 M, 0.25 M, 0.26 M, 0.27 M, 0.28 M, 0.29 M, 0.30 M, 0.31 M, 0.32 M, 0.33 M, 0.34 M, 0.35 M, 0.36 M, 0.37 M, 0.38 M, 0.39 M, 0.40 M, 0.41 M, 0.42 M, 0.43 M, 0.44 M, 0.45 M, 0.46 M, 0.47 M, 0.48 M, 0.49 M, 0.5 M. In some cases, the composition comprises saline, e.g., NaCl, at a concentration of at most about 0.05 M, 0.06M, 0.07 M, 0.08 M, 0.09 M, 0.10 M, 0.11 M, 0.12 M, 0.13 M, 0.14 M, 0.15 M, 0.16 M, 0.17 M, 0.18 M, 0.19 M, 0.20 M, 0.21 M, 0.22 M, 0.23 M, 0.24 M, 0.25 M, 0.26 M, 0.27 M, 0.28 M, 0.29 M, 0.30 M, 0.31 M, 0.32 M, 0.33 M, 0.34 M, 0.35 M, 0.36 M, 0.37 M, 0.38 M, 0.39 M, 0.40 M, 0.41 M, 0.42 M, 0.43 M, 0.44 M, 0.45 M, 0.46 M, 0.47 M, 0.48 M, 0.49 M, 0.5 M. In some cases, the NaCl is present at a concentration of 0.05 to 0.2 M, or 0.10 to 0.25 M, or 0.12 to 0.3 M.

In some cases, the pH of the composition is a pH of 4, 4.1, 4.2, 4.3, 4.4, 4.5, 4.6, 4.7, 4.8, 4.85, 4.95, 5.0, 5.05, 5.15, 5.2, 5.25, 5.3, 5.35, 5.4, 5.45, 5.5, 5.6, 5.65, 5.7, 5.75, 5.8, 5.85, 5.9, 5.95, 6.0, 6.05, 6.15, 6.2, 6.25, 6.3, 6.35, 6.4, 6.45, 6.5, 6.6, 6.65, 6.7, 6.75, 6.8, 6.85, 6.9, 6.95, 7.0, 7.05, 7.15, 7.2, 7.25, 7.3, 7.35, 7.4, 7.45, 7.5, 7.6, 7.65, 7.7, 7.75, 7.8, 7.85, 7.9, 7.95, 8.0, 8.05, 8.15, 8.2, 8.25, 8.3, 8.35, 8.4, 8.45, 8.5, 8.6, 8.65, 8.7, 8.75, 8.8, 8.85, 8.9, 8.95, or 9.0. In some cases, the pH of the composition is a pH of less than about 4, 4.1, 4.2, 4.3, 4.4, 4.5, 4.6, 4.7, 4.8, 4.85, 4.95, 5.0, 5.05, 5.15, 5.2, 5.25, 5.3, 5.35, 5.4, 5.45, 5.5, 5.6, 5.65, 5.7, 5.75, 5.8, 5.85, 5.9, 5.95, 6.0, 6.05, 6.15, 6.2, 6.25, 6.3, 6.35, 6.4, 6.45, 6.5, 6.6, 6.65, 6.7, 6.75, 6.8, 6.85, 6.9, 6.95, 7.0, 7.05, 7.15, 7.2, 7.25, 7.3, 7.35, 7.4, 7.45, 7.5, 7.6, 7.65, 7.7, 7.75, 7.8, 7.85, 7.9, 7.95, 8.0, 8.05, 8.15, 8.2, 8.25, 8.3, 8.35, 8.4, 8.45, 8.5, 8.6, 8.65, 8.7, 8.75, 8.8, 8.85, 8.9, 8.95, or 9.0. In some cases, the pH of the composition is a pH of at least about 4, 4.1, 4.2, 4.3, 4.4, 4.5, 4.6, 4.7, 4.8, 4.85, 4.95, 5.0, 5.05, 5.15, 5.2, 5.25, 5.3, 5.35, 5.4, 5.45, 5.5, 5.6, 5.65, 5.7, 5.75, 5.8, 5.85, 5.9, 5.95, 6.0, 6.05, 6.15, 6.2, 6.25, 6.3, 6.35, 6.4, 6.45, 6.5, 6.6, 6.65, 6.7, 6.75, 6.8, 6.85, 6.9, 6.95, 7.0, 7.05, 7.15, 7.2, 7.25, 7.3, 7.35, 7.4, 7.45, 7.5, 7.6, 7.65, 7.7, 7.75, 7.8, 7.85, 7.9, 7.95, 8.0, 8.05, 8.15, 8.2, 8.25, 8.3, 8.35, 8.4, 8.45, 8.5, 8.6, 8.65, 8.7, 8.75, 8.8, 8.85, 8.9, 8.95, or 9.0.

In some cases, the composition comprises sodium acetate (or sodium ethanoate), e.g., at least about 1 mM, 2, mM, 3 mM, 4 mM, 5 mM, 6 mM, 7 mM, 8 mM, 9 mM 9.1 mM, 9.2 mM, 9.3 mM, 9.4 mM, 9.5, mM, 9.6 mM, 9.7 mM, 9.8 mM, 9.9 mM, 10.0 mM, 10.1 mM, 10.2 mM, 10.3 mM, 10.4 mM, 10.5 mM, 10.6 mM, 10.7 mM, 10.8 mM, 10.9 mM, 11 mM, 11.1 mM, 11.2 mM, 11.3 mM, 11.4 mM, 11.5 mM, 11.6 mM, 11.7 mM, 11.8 mM, 11.9 mM, 12 mM, 12.5 mM, 13 mM, 14 mM, 15 mM, 20 mM, 25 mM, or 30 mM sodium acetate. Preferably the composition comprises sodium acetate at a concentration of 5 to 20 mM, 6 to 15 mM, and, more preferably, 8 to 12 mM (e.g., 8 mM, 9 mM, 10 mM, 11 mM, or 12 mM). In some cases, the composition comprises sodium acetate (or sodium ethanoate) at a concentration of at most 1 mM, 2, mM, 3 mM, 4 mM, 5 mM, 6 mM, 7 mM, 8 mM, 9 mM 9.1 mM, 9.2 mM, 9.3 mM, 9.4 mM, 9.5, mM, 9.6 mM, 9.7 mM, 9.8 mM, 9.9 mM, 10.0 mM, 10.1 mM, 10.2 mM, 10.3 mM, 10.4 mM, 10.5 mM, 10.6 mM, 10.7 mM, 10.8 mM, 10.9 mM, 11 mM, 11.1 mM, 11.2 mM, 11.3 mM, 11.4 mM, 11.5 mM, 11.6 mM, 11.7 mM, 11.8 mM, 11.9 mM, 12 mM, 12.5 mM, 13 mM, 14 mM, 15 mM, 20 mM, 25 mM, or 30 mM.

In some cases, the composition comprises sodium phosphate, e.g., at least about 1 mM, 2, mM, 3 mM, 4 mM, 5 mM, 6 mM, 7 mM, 8 mM, 9 mM 9.1 mM, 9.2 mM, 9.3 mM, 9.4 mM, 9.5, mM, 9.6 mM, 9.7 mM, 9.8 mM, 9.9 mM, 10.0 mM, 10.1 mM, 10.2 mM, 10.3 mM, 10.4 mM, 10.5 mM, 10.6 mM, 10.7 mM, 10.8 mM, 10.9 mM, 11 mM, 11.1 mM, 11.2 mM, 11.3 mM, 11.4 mM, 11.5 mM, 11.6 mM, 11.7 mM, 11.8 mM, 11.9 mM, 12 mM, 12.5 mM, 13 mM, 14 mM, 15 mM, 20 mM, 25 mM, or 30 mM sodium phosphate. Preferably, the composition comprises sodium phosphate at a concentration of 5 to 20 mM, 6 to 15 mM, and, more preferably, 8 to 12 mM (e.g., 8 mM, 9 mM, 10 mM, 11 mM, or 12 mM). In some cases, the composition comprises sodium phosphate at a concentration of at most about 1 mM, 2, mM, 3 mM, 4 mM, 5 mM, 6 mM, 7 mM, 8 mM, 9 mM 9.1 mM, 9.2 mM, 9.3 mM, 9.4 mM, 9.5, mM, 9.6 mM, 9.7 mM, 9.8 mM, 9.9 mM, 10.0 mM, 10.1 mM, 10.2 mM, 10.3 mM, 10.4 mM, 10.5 mM, 10.6 mM, 10.7 mM, 10.8 mM, 10.9 mM, 11 mM, 11.1 mM, 11.2 mM, 11.3 mM, 11.4 mM, 11.5 mM, 11.6 mM, 11.7 mM, 11.8 mM, 11.9 mM, 12 mM, 12.5 mM, 13 mM, 14 mM, 15 mM, 20 mM, 25 mM, or 30 mM.

Non-limiting examples of pharmaceutically-acceptable excipients suitable for use in the invention can include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material and spheronization agents, and any combination thereof.

The formulated composition can include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). In some cases, the composition comprises awater miscible non-aqueous solvent selected from the group consisting of ethanol, glycerin, propylene glycol, polyethylene glycol, and combinations thereof.

Compositions can be injectable. Injectable compositions can be aqueous. Aqueous compositions can comprise an effective amount of a fusion antibody, which may be dissolved or dispersed in a pharmaceutically acceptable carrier or aqueous medium. Unless a pharmaceutical composition is incompatible with the active ingredient, it can be used in a therapeutic compositions. Supplementary active ingredients can also be incorporated into the compositions.

Exemplary pharmaceutically acceptable carriers for liquid or injectable compositions can include calcium salts, for example, such as calcium chlorides, calcium bromides, calcium sulfates, and the like; and the salts of organic acids such as acetates, propionates, malonates, benzoates, and the like.

In some cases, the composition comprises detergent at a low concentration. For example, the composition may comprise detergent (e.g., polysorbate-80, Tween-80, etc.) at a concentration of less than 10%, 5%, 4%, 3%, 2%, 1.9%, 1.5%, 1.0%, 0.5%, 0.1%, 0.05%, 0.001%, 0.0005%, or 0.0001%, preferably less than 0.0015%, or less than 0.001%.

In some cases, the aqueous composition is formulated with saline, detergent, carbohydrate, sodium acetate and/or sodium phosphate in any combination and at a particular pH. For example, aqueous compositions may be formulated in saline (e.g., NaCl 0.01M-0.5M) based on a solution of varying pH (5-8), with or without detergents such as polysorbate-80 (or Tween-80) at 0.0001%-1%, or carbohydrate additives, such as mannitol, sorbitol, trehalose, or monosaccharide as described herein (e.g., dextrose or glucose at a concentration of between 2% and 20%, preferably between 5% and 15%, more preferably between 5% and 10%.). In another example, the composition may comprise: 0.08-0.3 M NaCl, 5 mM-30 mM sodium acetate (or sodium phosphate), and a low concentration of detergent (e.g., less than 0.01% polysorbate-80 or less than 0.001% polysorbate-80, or as described further herein). In yet another example, the composition may comprise between 0.10 and 0.16 M NaCl, 5 mM-15 mM sodium acetate (or sodium phosphate), low detergent (as described further herein), and/or monosaccharide (at a concentration as described further herein).

Commonly used buffers in aqueous compositions can include histidine, acetate, phosphate, or citrate. Under ordinary conditions of storage and use, these preparations can comprise a preservative to prevent the growth of microorganisms. The prevention of the growth of microorganisms can be brought about by various antibacterial and antifungal agents, for example, parabens, chlorobutanol; phenol, sorbic acid, thimerosal, and the like. In many cases, the aqueous pharmaceutically acceptable carrier can comprise isotonic agents, for example, sugars or sodium chloride. Prolonged absorption of the injectable compositions can be brought about by the use in the compositions of agents delaying absorption, for example, aluminum monostearate, and gelatin.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release. Injectable compositions can also be suspensions, dispersions, solubilized lyophilizations, or emusions.

Sterile injectable compositions can be prepared by incorporating the active compounds in the required amount in the appropriate solvent with various of the other ingredients, as required, followed by filtered sterilization. Generally, dispersions can be prepared by incorporating the various sterilized active ingredients into a sterile vehicle which comprises the basic dispersion medium and the required other ingredients. Methods of preparation can include vacuum-drying and freeze-drying techniques which can yield a powder of the active ingredient plus any additional desired ingredient from a previously sterile-filtered solution thereof.

Parental injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration can include aqueous solutions of the active compounds in water-soluble form.

Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

In addition to the compounds formulated for parenteral administration, such as intravenous or intramuscular injection, other alternative methods of administration of the present invention may also be used, including but not limited to intradermal administration, pulmonary administration, buccal administration, transdermal administration, transmucosal administration, and intranasal administration. Intranasal administration can be performed with nasal solutions or sprays, aerosols or inhalants. Nasal compositions can be aqueous solutions designed to be administered to the nasal passages in drops or sprays. Nasal solutions can be prepared so that they are similar in many respects to nasal secretions (e.g., viscosity, pH, salt composition). Aqueous nasal solutions can be isotonic and slightly buffered to maintain a pH of 5.5 to 6.5. Antimicrobial preservatives, similar to those used in ophthalmic preparations and appropriate drug stabilizers may be included in the nasal solution. For administration by inhalation, the active compounds can be in a form as an aerosol, a mist, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

Formulations suitable for transdermal administration of the active compounds can employ transdermal delivery devices and transdermal delivery patches, and can be lipophilic emulsions or buffered aqueous solutions, dissolved and/or dispersed in a polymer or an adhesive. Such patches can be constructed for continuous, pulsatile, or on demand delivery of pharmaceutical compounds. Transdermal delivery can be accomplished by means of iontophoretic patches and the like. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin.

The composition can be administered topically. The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Suppository and pessary compositions can be used. Suppositories can be solid dosage forms of various weights and shapes, usually medicated. After insertion, suppositories can soften, melt or dissolve in the cavity fluids. Traditional suppository binders and carriers can include, for example, polyalkylene glycols or triglycerides; such suppositories may be formed from mixtures comprising the active ingredient in any suitable range, e.g., in the range of about 0.5% to about 10%, preferably 1%-2%. The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

Oral compositions can include excipients such as, for example, pharmaceutical grades of mannitol, lactose, starch, magnesium stearate, sodium saccharine, cellulose, magnesium carbonate and the like. These compositions can take the form of solutions, suspensions, tablets, pills, capsules, sustained release formulations, or powders. In certain defined embodiments, oral pharmaceutical compositions can comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can comprise at least 0.1% of active compound. The percentage of the compositions and preparations may be varied, and may be about 2%, 5%, 10%, 15%, 20%, 25%, 30%, 35%, 40%, 45%, 50%, 55%, 60%, 65%, 70%, 75% or more of the weight of the unit. The amount of active compounds in such compositions can be such that a suitable dosage can be obtained. For oral administration, pharmaceutical compositions can be formulated readily by combining the active compounds with pharmaceutically-acceptable carriers or excipients. Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, and/or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

When the composition is a capsule, it may comprise a liquid carrier. Various other materials may be present as coatings or to otherwise modify the physical form of the dosage unit. For instance, tablets, pills, or capsules may be coated with shellac, sugar or both. A syrup of elixir may comprise the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach.

Methods for the preparation of compositions comprising the structures and/or substances described herein include formulating the structures and/or substances with one or more inert, pharmaceutically-acceptable excipients or carriers to form a solid, semi-solid, or liquid composition. Solid compositions can include, for example, powders, tablets, dispersible granules, capsules, cachets, and suppositories. In some instances, the composition may be lyophilized. Liquid compositions can include, for example, solutions in which a compound is dissolved, emulsions comprising a compound, or a solution containing liposomes, micelles, or nanoparticles comprising a compound as disclosed herein. Semi-solid compositions can include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

The active ingredients may also be entrapped in microcapsules prepared, for example, by coacervation techniques or by interfacial polymerization, for example, hydromethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Non-limiting examples of dosage forms suitable for use can include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

A composition of the disclosure (e.g., structure and/or substance) can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, granular masses, and the like.

In some instances, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Salts of Compositions

In some instances, the composition can comprise a pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Combination Therapy Compositions

The compositions of the invention may be administered as part of a combination therapy. Combination therapy can involve the administration of a composition of the invention in combination with another therapy for treatment or relief of symptoms typically found in a patient suffering from any of the above-mentioned CNS conditions. If the composition is used in combination with another CNS disorder method or composition, any combination of the composition and the additional method or composition may be used. Thus, for example, if use of a composition is in combination with another CNS disorder treatment agent, the two may be administered simultaneously, consecutively, in overlapping durations, in similar, the same, or different frequencies, etc. In some cases a composition can be used that comprises a composition in combination with one or more other CNS disorder treatment agents.

In some embodiments, the composition, can be co-administered to the patient with another medication, either within the same formulation or as a separate composition. For example, the fusion antibody can be formulated with another fusion antibody. Further, the fusion antibody may be formulated in combination with other large or small molecules.

For example, exemplary agents for co-administration to treat a CNS inflammatory condition can include immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-α, interleukin-2, allergy vaccines, antihistamines, antileukotrienes, beta-agonists, theophylline, anticholinergics, or any combination thereof.

Exemplary agents that be can co-administered with for Treating Multiple Sclerosis can include Interferon β-1a, Interferon β-1b, glatiramer acetate (Copaxone®), mitoxantrone (Novantrone®), low dose naltrexone, Natalizumab (Tysabri®), Sativex®, Aimspro (Goats Serum), Trimesta (Oral Estriol), Laquinimod, FTY720 (Fingolimod), MBP8298, NeuroVax™, Tovaxin™, Revimmune, CHR-1103, BHT-3009, BG-12, Cladribine, daclizumab (Zenapax) Rituximab (Rituxan), cyclophosphamide, Campath, Fampridine-SR, MN-166, Temsirolimus, RPI-78M, or any combination thereof.

Exemplary agents that can be co-administered for treatment of Alzheimer's Disease or AIDS-related Dementia can include Flurizan™ (MPC-7869, r flurbiprofen), memantine, galantamine, rivastigmine, donezipil, tacrine, $Aβ_{1-42}$ immunotherapy, resveratrol, (−)-epigallocatechin-3-gallate, statins, vitamin C, vitamin E, or any combination thereof.

Exemplary agents for Treating Thromboembolic Disorders can include thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, BIBR 1048, or any combination thereof.

In practicing the methods of treatment or use provided herein, therapeutically-effective amounts of the compounds described herein can be administered in pharmaceutical compositions to a subject having a disease or condition to be treated (e.g., a CNS disorder). In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures (e.g., a structure and a substance).

Methods of Administration

A pharmacological composition comprising a structure and/or a substance (e.g., glucose) can be administered to a subject. A subject or an patient, can refer to an animal, for example, a mammal (e.g., dog, cow, mouse, rat, primate). In some embodiments a subject or an individual can be a human. In some instances, the subject can suffer from Hurler's Syndrome. In some instances, the subject can suffer from Hunter's Syndrome.

A pharmacological composition comprising a fusion antibody can be administered peripherally or peripherally administered. As used herein, these terms can refer to any form of administration of an agent, (e.g., a therapeutic agent), to an individual that is not direct administration to the CNS, (e.g., that brings the agent in contact with the non-brain side of the blood-brain barrier). Peripheral administration can include intravenous, intra-arterial, subcutaneous, intramuscular, intraperitoneal, transdermal, by inhalation, transbuccal, intranasal, rectal, oral, parenteral, sublingual, or trans-nasal.

The appropriate quantity of the composition of the disclosure to be administered, the number of treatments, and unit dose can vary according to the CNS uptake characteristics of a fusion antibody according to the subject to be treated and the disease state of the subject. The person responsible for administration can determine the appropriate dose for the individual subject.

Dosages comprising the structure can be at least about 0.1 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 12 mg/kg, 14 mg/kg, 16 mg/kg, 18 mg/kg, 20 mg/kg, 22 mg/kg, 24 mg/kg, 26 mg/kg, 28 mg/kg, 30 mg/kg, 32 mg/kg, 34 mg/kg, 36 mg/kg, 38 mg/kg, 40 mg/kg, or more.

Dosages comprising the structure can be no more than 0.1 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 12 mg/kg, 14 mg/kg, 16 mg/kg, 18 mg/kg, 20 mg/kg, 22 mg/kg, 24 mg/kg, 26 mg/kg, 28 mg/kg, 30 mg/kg, 32 mg/kg, 34 mg/kg, 36 mg/kg, 38 mg/kg, 40 mg/kg, or more.

Dosages comprising the structure can be administered at least about once per second, twice per second, three times per second, four times per second, five times per second, six times per second, seven times per second, eight times per second, nine times per second, once per minute, twice per minute, three times per minute, four times per minute, five times per minute, six times per minute, seven times per minute, eight times per minute, nine times per minute, once per hour, twice per hour, three times per hour, four times per hour, five times per hour, six times per hour, seven times per hour, eight times per hour, nine times per hour, once per day, twice per hour, three times per hour, four times per hour, five times per hour, six times per hour, seven times per hour, eight times per hour, nine times per hour, once per week, twice per week, three times per week, four times per week, five times per week, six times per week, seven times per week, eight times per week, nine times per week, once per month, twice per month, three times per month, four times per month, five times per month, six times per month, seven times per month, eight times per month, nine times per month, once per year, twice per year, three times per year, four times per year, five times per year, six times per year, seven times per year, eight times per year, nine times per year.

Dosages comprising the structure can be administered continuously. Dosages can be administered continuously for more than one second, for more than one minute, for more than 10 minutes, for more than 30 minutes, for more than one hour, for more than 2 hours, for more than 3 hours, for more than 5 hours, for more than 6 hours, for more than one day, for more than 2 days, for more than 3 days, for more than 4 days, for more than one week, for more than 2 weeks, for more than 3 weeks, for more than 1 month, for more than 3 months, for more than 6 months, for more than 1 year.

Dosages comprising the structure cause return glucose and/or dextrose levels in a hyperglycemic subject to become 50%, 60%, 70%, 80%, 90%, or 100% of normal body glucose levels. Dosages can cause glucose levels in a hypoglycemic subject to become 50%, 60%, 70%, 80%, 90%, or 100% of normal body glucose levels. Dosages comprising the structure can be administered intravenously, intra-arterially, subcutaneously, intramuscularly, intraperitoneally, transdermally, by inhalation, transbuccally, intranasally, rectally, orally, parenterally, sublingually, transalveolarly, or trans-nasal.

Dosages comprising the structure can vary depending on the polypeptide sequence fused to the fusion antibody. Different polypeptide sequences can have different uptake characteristics and affinity for the BBB receptor.

Compositions can be systemically administered in an effective amount. An effective amount is an amount which when administered systemically, is sufficient to effect beneficial or desired results (e.g., in treatment of a CNS disorder). An effective amount can be an amount that produces a prophylactic effect (e.g., an amount that delays, reduces, or eliminates the appearance of an acute pathological or undesired condition). An effective amount can be administered in one or more administrations. An effective amount can be an amount that is sufficient to palliate, ameliorate, stabilize, reverse or slow the progression of a disorder (e.g., a neurological disorder). An effective amount may be used alone or in conjunction with one or more agents used to treat a disease or disorder. An "effective amount" of a therapeutic agent can be determined by a patient's attending physician or veterinarian.

Therapeutically effective can refer to a dosage that results in a measurable effect on the CNS condition. A therapeutically effective amount may refer to an amount of the fusion antibody that can cross the BBB in order to have an effect on the CNS condition.

IDS Fusion Antibodies

An IDS structure (e.g., IDS fusion antibody, IDS-mAb HIR) can be systemically administered. An IDS fusion antibody can comprise at least about 0.3% (i.e., about 0.32%), 0.4%, 0.48%, 0.6%, 0.74%, 0.8%, 0.9%, 1.05, 1.1, 1.2, 1.3%, 1.5%, 2%, 2.5%, 5%, or any percentage from about 0.3% to about 12% of the systemically administered IDS fusion antibody can be delivered to the brain as a result of its uptake from peripheral blood across the BBB. An IDS fusion antibody can comprise at most about 0.3% (i.e., about 0.32%), 0.4%, 0.48%, 0.6%, 0.74%, 0.8%, 0.9%, 1.05, 1.1, 1.2, 1.3%, 1.5%, 2%, 2.5%, 5%, or any percentage from about 0.3% to about 12% of the systemically administered IDS fusion antibody can be delivered to the brain as a result of its uptake from peripheral blood across the BBB. In some embodiments, at least about 0.5%, (i.e., about 0.32%, 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered dose of the IDS fusion antibody can be delivered to the brain within two hours or less (e.g., 1.8, 1.7, 1.5, 1.4, 1.3, 1.2, 1.1, 0.9, 0.8, 0.6, 0.5) or any other period from about 0.5 to about two hours after systemic administration. In some embodiments, at most about 0.5%, (i.e., about 0.32%, 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered dose of the IDS fusion antibody can be delivered to the brain within two hours or less (e.g., 1.8, 1.7, 1.5, 1.4, 1.3, 1.2, 1.1, 0.9, 0.8, 0.6, 0.5) or any other period from about 0.5 to about two hours after systemic administration.

IDS fusion antibodies can cross the BBB, and may provide at least about 0.125, 0.14, 0.15, 0.16, 0.17, 0.18, 0.19, 0.2, 0.21, 0.22, 0.23, 0.24, 0.25, 0.3, 0.4, 0.5, 0.75, 1.0, 1.5, 2, 2.1, 2.2, 2.3, 2.4, 2.5 or more units of IDS activity/mg protein in the subject's brain. IDS fusion antibodies can cross the BBB, and may provide at most about 0.125, 0.14, 0.15, 0.16, 0.17, 0.18, 0.19, 0.2, 0.21, 0.22, 0.23, 0.24, 0.25, 0.3, 0.4, 0.5, 0.75, 1.0, 1.5, 2, 2.1, 2.2, 2.3, 2.4, 2.5 or more units of IDS activity/mg protein in the subject's brain.

In some embodiments, the total number of units of IDS activity delivered to a subject's brain can be at least about 5000, 10000, 12000, 12500, 15,000, 20000, 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, 250,000, 300000, 500000, 1000000 or more units of IDS activity. In some embodiments, the total number of units of IDS activity delivered to a subject's brain can be at most about 5000, 10000, 12000, 12500, 15,000, 20000, 25,000, 30,000, 35,000, 40,000, 45,000, 50,000, 60,000, 70,000, 80,000, 90,000, 110,000, 120,000, 130,000, 140, 000, 150,000, 160,000, 170,000, 180,000, 190,000, 200,000, 210,000, 220,000, 230,000, 250,000, 300000, 500000, 1000000 or more units of IDS activity. In some embodiments, at least about 25,000 units of iduronate-2-sulfatase activity can be delivered to the brain, normalized per 50 kg body weight.

In some embodiments, a therapeutically effective systemic dose can comprise at least about $5\times10^5$, $1\times10^6$, $2\times10^6$, $3\times10^6$, 4, $10^6$, $5\times10^6$, $6\times10^6$, $7\times10^6$, $8\times10^6$, $9\times10^6$, $1\times10^7$, $1.1\times10^7$, $1.2\times10^7$, $1.5\times10^7$, $1.6\times10^7$, $1.7\times10^7$, $1.8\times10^7$, $1.9\times10^7$, $2\times10^7$, $2.1\times10^7$, $3\times10^7$ or more units of IDS activity. In some embodiments, a therapeutically effective systemic dose can comprise at most about $5\times10^5$, $1\times10^6$, $2\times10^6$, $3\times10^6$, 4, $10^6$, $5\times10^6$, $6\times10^6$, $7\times10^6$, $8\times10^6$, $9\times10^6$, $1\times10^7$, $1.1\times10^7$, $1.2\times10^7$, $1.5\times10^7$, $1.6\times10^7$, $1.7\times10^7$, $1.8\times10^7$, $1.9\times10^7$, $2\times10^7$, $2.1\times10^7$, $3\times10^7$ or more units of IDS activity. The therapeutically effective systemic dose can comprise at least $5\times10^5$ units of IDS activity. A therapeutically effective systemic dose can be at least about 10,000, 15,000, 20,000, 22,000, 24,000, 25,000, 30,000, 40,000, 50,000, 60,000, 70,000, 80,000, 90,000, 100,000, 125,000, 150,000, 200,000, 500,000 or more units/kg body weight. A therapeutically effective systemic dose can be at most about 10,000, 15,000, 20,000, 22,000, 24,000, 25,000, 30,000, 40,000, 50,000, 60,000, 70,000, 80,000, 90,000, 100,000, 125,000, 150,000, 200,000, 500,000 or more units/kg body weight. A therapeutically effective systemic dose at least about 20,000 units of IDS activity/kg body weight.

The mass amount of a therapeutically effective systemic dose of an IDS fusion antibody may depend, in part, on its IDS specific activity. In some embodiments, the IDS specific activity of the IDS fusion antibody can be at least about 10,000 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, 50,000, or more units/mg of protein. In some embodiments, the IDS specific activity of the IDS fusion antibody can be at most about 10,000 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, 50,000, or more units/mg of protein.

The IDS fusion antibody may be administered to the subject in a large variety of different formulations including those known in the art, and those provided herein for the greater structure. In certain non-limiting examples, the IDS fusion protein is provided in a solution that has a total pH of about 4.0, 4.5, 5.0, 5.1, 5.2, 5.3, 5.3, 5.5, 5.7, 5.8, 6.0, 6.2, 6.3, 6.4, 6.5, or 7.0. In certain preferred embodiments, the pH of the solution comprising the IDS fusion protein is between about 5.0 to about 6.5. In certain preferred embodiments, the pH is about 5.5. In certain embodiments, the pH is about 6.0. And, in other embodiments, the pH is 6.5, or less than 6.5. In some cases, the IDS fusion protein is present in a solution with pH of about 5.5 to about 6.2 and the solution also comprises one or more of the following: low detergent (e.g., less than 0.01% polysorbate or other value provided herein), sodium acetate, and monosaccharide (e.g., dextrose at a concentration of between about 5% to about 10%). In some cases, the IDS fusion protein is present in a solution with pH of about 5.5 to about 6.2 and the solution also comprises one or more of the following: low detergent (e.g., less than 0.01% polysorbate or other value provided herein), sodium phosphate, and monosaccharide (e.g., dextrose at a concentration of between about 5% to about 10%).

IDUA Fusion Antibodies

An IDUA fusion antibody can be systemically administered. An IDUA fusion antibody can comprise at least about 0.3% (e.g., about 0.32%), 0.4%, 0.48%, 0.6%, 0.74%, 0.8%, 0.9%, 1.05, 1.1, 1.2, 1.3%, 1.5%, 2%, 2.5%, 5%, or any percentage from about 0.3% to about 12% of the systemically administered IDUA fusion antibody can be delivered to the brain as a result of its uptake from peripheral blood across the BBB. An IDUA fusion antibody can comprise at most about 0.3% (e.g., about 0.32%), 0.4%, 0.48%, 0.6%, 0.74%, 0.8%, 0.9%, 1.05, 1.1, 1.2, 1.3%, 1.5%, 2%, 2.5%, 5%, or any percentage from about 0.3% to about 12% of the systemically administered IDUA fusion antibody can be delivered to the brain as a result of its uptake from peripheral blood across the BBB. In some embodiments, at least 0.5%, (i.e., about 0.32%, 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered dose of the IDUA fusion antibody can be delivered to the brain within two hours or less (e.g., 1.8, 1.7, 1.5, 1.4, 1.3, 1.2, 1.1, 0.9, 0.8, 0.6, 0.5) or any other period from about 0.5 to about two hours after systemic administration. In some embodiments, at most about 0.5%, (i.e., about 0.32%, 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered dose of the IDUA fusion antibody can be delivered to the brain within two hours or less (e.g., 1.8, 1.7, 1.5, 1.4, 1.3, 1.2, 1.1, 0.9, 0.8, 0.6, 0.5) or any other period from about 0.5 to about two hours after systemic administration.

IDUA fusion antibodies can cross the BBB, and may provide at least about 0.125, 0.14, 0.15, 0.16, 0.17, 0.18, 0.19, 0.2, 0.21, 0.22, 0.23, 0.24, 0.25, 0.3, 0.4, 0.5, 0.75, 1.0, 1.5, 2, 2.1, 2.2, 2.3, 2.4, 2.5 or more units of IDUA activity/mg protein in the subject's brain. IDUA fusion antibodies can cross the BBB, and may provide at most about 0.125, 0.14, 0.15, 0.16, 0.17, 0.18, 0.19, 0.2, 0.21, 0.22, 0.23, 0.24, 0.25, 0.3, 0.4, 0.5, 0.75, 1.0, 1.5, 2, 2.1, 2.2, 2.3, 2.4, 2.5 or more units of IDUA activity/mg protein in the subject's brain.

With due consideration of the specific activity of a HIR Ab-IDUA fusion antibody and the body weight of a subject to be treated, a systemic dose of the HIR Ab-IDUA fusion antibody can be at least 2, 5, 10, 15, 20, 25, 30, 35, 40, 45, 50, 55, 60, 65, 70, 75, 100 or more mg of IDUA fusion antibody. The HIR Ab-IDUA fusion antibody can be at most 2, 5, 10, 15, 20, 25, 30, 35, 40, 45, 50, 55, 60, 65, 70, 75, 100 or more mg of IDUA fusion antibody.

In some embodiments, the total number of units of IDUA activity delivered to a subject's brain can be at least, 5000, 10000, 12000, 12500, 15,000, 20000, 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, 250,000, 300000, 500000, 1000000 or more units of IDUA activity. In some embodiments, the total number of units of IDUA activity delivered to a subject's brain can be at most about 5000, 10000, 12000, 12500, 15,000, 20000, 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, 250,000, 300000, 500000, 1000000 or more units of IDUA activity. In some embodiments, at least about 25,000 units of IDUA activity can be delivered to the brain, normalized per 50 kg body weight.

In some embodiments, a therapeutically effective systemic dose can comprise at least $5\times10^5$, $1\times10^6$, $2\times10^6$, $3 \times 10^6$, 4, $10^6$, $5 \times 10^6$, $6 \times 10^6$, $7 \times 10^6$, $8 \times 10^6$, $9 \times 10^6$, $1 \times 10^7$, $1.1 \times 10^7$, $1.2 \times 10^7$, $1.5 \times 10^7$, $1.6 \times 10^7$, $1.7 \times 10^7$, $1.8 \times 10^7$, $1.9 \times 10^7$, $2 \times 10^7$, $2.1 \times 10^7$, $3 \times 10^7$ or more units of IDUA activity. In some embodiments, a therapeutically effective systemic dose can comprise at most about $5 \times 10^5$, $1 \times 10^6$, $2 \times 10^6$, $3 \times 10^6$, 4, $10^6$, $5 \times 10^6$, $6 \times 10^6$, $7 \times 10^6$, $8 \times 10^6$, $9 \times 10^6$, $1 \times 10^7$, $1.1 \times 10^7$, $1.2 \times 10^7$, $1.5 \times 10^7$, $1.6 \times 10^7$, $1.7 \times 10^7$, $1.8 \times 10^7$, $1.9 \times 10^7$, $2 \times 10^7$, $2.1 \times 10^7$, $3 \times 10^7$ or more units of IDUA activity. therapeutically effective systemic dose can comprise at least $5 \times 10^5$ units of IDUA activity. A therapeutically effective systemic dose can be at least about 10,000, 15,000, 20,000, 22,000, 24,000, 25,000, 30,000, 40,000, 50,000, 60,000, 70,000, 80,000, 90,000, 100,000, 125,000, 150,000, 200,000, 500,000 or more units/kg body weight. A therapeutically effective systemic dose can be at most about 10,000, 15,000, 20,000, 22,000, 24,000, 25,000, 30,000, 40,000, 50,000, 60,000, 70,000, 80,000, 90,000, 100,000, 125,000, 150,000, 200,000, 500,000 or more units/kg body weight. A therapeutically effective systemic dose at least about 20,000 units of IDUA activity/kg body weight.

The mass amount of a therapeutically effective systemic dose of an IDUA fusion antibody may depend, in part, on its IDUA specific activity. In some embodiments, the IDUA specific activity of the IDUA fusion antibody can be at least about 10,000 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, 50,000, or more units/mg of protein. In some embodiments, the IDUA specific activity of the IDUA fusion antibody can be at most about 10,000 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, 50,000, or more units/mg of protein.

The IDUA fusion antibody may be administered to the subject in a large variety of different formulations including those known in the art, and those provided herein for the greater structure. In certain non-limiting examples, the IDUA fusion protein is provided in a solution that has a total pH of about 4.0, 4.5, 5.0, 5.1, 5.2, 5.3, 5.3, 5.5, 5.7, 5.8, 6.0, 6.2, 6.3, 6.4, 6.5, or 7.0. In certain preferred embodiments, the pH of the solution comprising the IDUA fusion protein is between about 5.0 to about 6.5. In certain preferred embodiments, the pH is about 5.5. In certain embodiments, the pH is about 6.0. And, in other embodiments, the pH is 6.5, or less than 6.5. In some cases, the IDUA fusion protein is present in a solution with pH of about 5.5 to about 6.2 and the solution also comprises one or more of the following: low detergent (e.g., less than 0.01% polysorbate or other value provided herein), sodium acetate, and monosaccharide (e.g., dextrose at a concentration of between about 5% to about 10%). In some cases, the IDUA fusion protein is present in a solution with pH of about 5.5 to about 6.2 and the solution also comprises one or more of the following: low detergent (e.g., less than 0.01% polysorbate or other value provided herein), sodium phosphate, and monosaccharide (e.g., dextrose at a concentration of between about 5% to about 10%).

CNS Conditions

Compositions of the disclosure can be administered to a subject with a CNS condition. In some cases, the CNS condition to be treated can be an acute CNS condition (e.g., focal ischemia, global ischemia, traumatic brain injury, or spinal cord injury). In some cases, the CNS condition to be treated can be a chronic CNS condition (e.g. a neurodegenerative condition, such as Alzheimer's disease, Parkinson's disease, amyotrophic lateral sclerosis, Huntington's disease, multiple sclerosis, transverse myelitis, motor neuron disease, Pick's disease, tuberous sclerosis, Canavan's disease, Rett's syndrome, spinocerebellar ataxias, Friedreich's ataxia, optic atrophy, or retinal degeneration).

In some embodiments, a fusion antibody can be systemically administered to treat a subject suffering from a stroke, head injury, spinal cord injury, a neurodegenerative condition, to block angiogenesis in a brain tumor, to treat dementia from acquired immune deficiency syndrome (AIDS), to treat multiple sclerosis (MS), to treat stroke, or to accelerate neural repair following stroke or brain injury.

Other CNS conditions can include, but are not limited to, encephalitis, meningitis, tropical spastic paraparesis, Arachnoid cysts, attention deficit/hyperactivity disorder (ADHD), locked-in syndrome, Tourette's, brain tumors, and brain strokes.

Methods of Detection

The disclosure provides for methods of detection of glucose in the body before, during or after administration of a structure (e.g., a fusion antibody) and a substance. In some cases, a monitoring system is useful for obtaining frequent measurements of a substance present in a biological system. The substance may be a monosaccharide. The substance may be glucose and/or dextrose. A monitoring system may comprise a sampling mechanism, a sensing mechanism, and a microprocessor mechanism in operative communication with the sampling mechanism and the sensing mechanism. A monitoring system can provide frequent measurement or determination of the analyte amount or concentration in the subject and can provide an alert or alerts when levels of the analyte being monitored fall outside of a predetermined range.

A monitoring system used to monitor the level of a selected substance in a target system can comprise a sampling device, which can provide a sample comprising the substance, and a sensing device, which can detect the amount or concentration of the substance or a signal associated with the substance amount or concentration in the sample. A monitoring system for monitoring glucose levels can be commercially available (e.g., from Olympus America, Inc. (Center Valley, Pa.); BioVision (Mountain View, Calif.)) Samples that can be used for monitoring glucose can originate from blood, CSF, urine, arterial plasma, venous plasma, serum, and the like.

In some instances, blood glucose and/or dextrose levels can be detected with a monitoring system that can draw blood from a subject and test the sample for glucose content. The samples can be collected by piercing the skin of the finger (the pinprick test). Continuous blood glucose monitoring (CGM) may be used to determine blood glucose levels at more frequent intervals, typically, every few minutes or so. Invasive techniques can involve the placement of a sensor under the skin which can communicate with a receiver configured to display or monitor the readings. CGM systems can monitor glucose levels of interstitial fluid rather than blood glucose levels directly. Interstitial fluid glucose levels can lag behind the blood glucose level. Because of this time lag, blood sugar levels may read in the normal range on a CGM system while in reality the patient is already experiencing symptoms of an out-of-range blood glucose value. In some instances, a monitoring system can comprise the use of infrared spectroscopy.

CSF glucose and/or dextrose levels can be measured on a CSF sample. CSF can refer to fluid that surrounds the brain and spinal cord. CSF can protect the brain from injury by preventing the brain from contacting the skull. CSF can be involved in biological functions such as cerebral blood flow and immunological protection. A CSF sample can be obtained, for example, from a lumbar puncture (e.g., spinal tap), cisternal puncture, ventricular puncture and/or ventricular drain. CSF levels can be tested using commercially available glucose monitoring systems. For example, CSF glucose levels can be tested using a spectrophotometric method (e.g., with an absorbance at 570 nanometers).

Low glucose and/or dextrose levels (e.g., lower than what is considered normal) can be referred to as hypoglycemia. Hypoglycemia can be symptomatic or asymptomatic. For example, subjects suffering from postprandial hypoglycemia generally have symptoms of adrenergic stimulation including diaphoresis, anxiety, irritability, palpitations, tremor, and hunger. Such symptoms can occur from about 2 to 4 hours postprandially with symptoms generally subsiding in about 15 to 20 minutes. Hypoglycemia can be caused by release of adrenergic and cholinergic hormones. Postprandial hypoglycemia can be idiopathic and can be caused by early diabetes, alcohol intake, renal failure, and drug treatments. In addition, a category of hypoglycemia exists which is designated as fasting hypoglycemia. Clinically, this form of hypoglycemia may have symptoms of neuroglycopenia including headache, fatigue, and mental dullness. In more severe cases, hypoglycemia can progress to confusion, blurring of vision, seizure, and ultimately loss of consciousness or seizure. Fasting hypoglycemia can occur with a fast of greater than 4 hours, and can be caused by insulinoma (resulting from self-administered insulin or intake of other hypoglycemic agents, alcohol abuse, liver disease (e.g., decreased gluconeogenesis), pituitary insufficiency, or adrenal insufficiency). Additional symptoms of hypoglycemia can include, but are not limited to, shakiness, anxiety, nervousness, palpitations, tachycardia, sweating, pallor, dilated pupils, hunger, nausea, vomiting, headache, fatigue, amnesia, and dizziness.

High glucose and/or dextrose levels (e.g., higher than what is considered normal) can be referred to as hyperglycemia. There can be many forms of hyperglycemia, the primary form being diabetes mellitus (DM) which can be defined as hyperglycemia secondary to decreased insulin production or an increase in peripheral tissue resistance to the action of insulin. Further, in the case of severe insulin deficiency, a starvation-like state can develop resulting in acidosis (typically referred to as diabetic ketoacidosis). Symptoms of ketoacidosis can include rapid respiration, acetone breath, vomiting, dehydration, nausea, abdominal pain and changes in mental stability.

Changes in glucose and/or dextrose levels can be associated with a variety of diseases. The maintenance of glucose and/or dextrose levels within normal range can be a matter of bringing the level down in hyperglycemia, or of bringing it up in various kinds of hypoglycemia. Some of hypoglycemias and/or hyperglycemias can be transient, others can be chronic. In some instances, hypoglycemia and/or hyperglycemia can be permanent.

Monitoring glucose and/or dextrose levels can determine if the subject is hypoglycemic, hyperglycemic, or has about normal blood and/or CSF glucose and/or dextrose levels. Glucose and/or dextrose levels between 100 and 126 mg/dl (milligrams/deciliter) can signify hyperglycemia. Glucose and/or dextrose levels above 126 mg/dl can signify the occurrence of diabetes. Glucose and/or dextrose levels between about 45 and 75 mg/dl can signify hypoglycemia. However, often, a diagnosis of hypoglycemia can require additional symptoms of hypoglycemia including shakiness, dysphoria, and mental inefficiency.

In some embodiments, the structure can be detected. Methods for detecting the structure can include, but are not limited to, western blot, ELISA, microscopy, immunostaining, electrophoresis, immunoblotting, and spectroscopy (e.g., mass spectroscopy).

The disclosure provides for methods comprising a) administering a composition to a subject comprising the structure and glucose and/or dextrose, and b) monitoring glucose and/or dextrose levels. The monitoring may occur 0 minutes, 1 minute, 2 minutes, 3 minutes, 4 minutes, 5 minutes, 10 minutes, 15 minutes, 20 minutes, 25 minutes, 30 minutes, 35 minutes, 40 minutes, 50 minutes, 60 minutes, 70 minutes, 80 minutes, 90 minutes, 100 minutes, 120 minutes, 140 minutes, 160 minutes, 180 minutes, 200 minutes, 240 minutes, 280 minutes, 300 minutes, 320 minutes, 340 minutes, 360 minutes or more after the first dosage (e.g., infusion). Monitoring may occur at a plurality of time points after administration.

If the monitoring indicates that blood and/or CSF levels have fallen (e.g. hypoglycemia), the subject can be treated with substances to increase blood and/or CSF sugar levels (i.e., agents described above). If the monitoring indicates that blood and/or CSF levels have risen (e.g. hyperglycemia), the subject can be treated with substances to decrease blood and/or CSF sugar levels (i.e., agents described above).

Nucleic Acids, Vectors, and Cells

The disclosure provides for nucleic acids that encode for a structure. A nucleic acid can comprise: (i) a first sequence encoding a heavy chain immunoglobulin and a polynucleotide sequence in frame with the heavy chain immunoglobulin; (ii) a second nucleic acid sequence encoding a light chain immunoglobulin and a polypeptide sequence in frame with the light chain immunoglobulin; (iii) the complementary sequence of (i) or (ii), or any combination thereof. In some instances, the nucleic acid can comprise both (i) a first sequence (or its complement) encoding a heavy chain immunoglobulin from an antibody against a BBB receptor and a polypeptide sequence in frame with the heavy chain immunoglobulin, and (ii) a second sequence (or its complement) encoding a light chain immunoglobulin from an antibody against the BBB receptor and a polypeptide sequence in frame with the light chain immunoglobulin all incorporated into a single piece of nucleic acid, e.g., a single piece of DNA. In some instances, a vector can comprise a polynucleotide sequence encoding a structure (e.g., SEQ ID NOs: 7 and 8). In some instances, a vector can comprise a polynucleotide sequence encoding any of the polypeptide sequences in FIGS. 7-14).

A vector can comprise a nucleic acid encoding a structure. A vector can comprise a plurality of nucleic acid sequences encoding for a structure. A vector can comprise a nucleic acid encoding for a light chain immunoglobulin of the structure and/or a heavy chain immunoglobulin of the structure. A vector can comprise a polynucleotide sequence encoding for one or more selection and/or amplification genes (e.g., dihydrofolate reductase (DHFR), neomycin phosphotransferase, hygromycin phosphotransferase, puromycin N-acetyl transferase). In some embodiments, the encoded selectable marker can be DHFR. In some embodiments, the vector can encode DHFR and a second selection/amplification marker (e.g., neomycin phosphotransferase).

A vector can comprise a promoter sequence. A promoter sequence can be operably linked to a nucleic acid encoding the fusion antibody of the disclosure. Examples of promoters can include constitutive promoters (cytomegalovirus (CMV) promoter, SV40 promoter, ubiquitin C promoter (UBC), etc), inducible promoters (doxycycline inducible promoters, tetracycline inducible promoters), and bidirectional promoters. A vector can comprise a plurality of promoter sequences. Each element of the vector (e.g., the amplification gene, the selection gene, the fusion antibody sequence) can be operably linked to its own promoter.

A vector can comprise a transcription termination sequence. Examples of transcription termination sequences can include hairpins and rho-dependent transcription terminators. A vector can comprise a plurality of transcription termination sequences. Each element of the vector (e.g., the amplification gene, the selection gene, the structure sequence) can be operably linked to its own transcription termination sequence.

A nucleic acid and/or a vector can further comprise a nucleic acid sequence that encodes for a peptide linker between the heavy chain of the antibody component and the polypeptide sequence component. The linker can comprise serine-serine-methionine (S-S-M). The linker can comprise serine-serine (S-S). The linker can comprise serine-serine-serine (S-S-S). The nucleic acid can comprise a nucleic acid sequence encoding for a signal peptide. The signal peptide can be fused to the heavy chain. The signal peptide can be fused to the light chain. Suitable signal peptides can include, nuclear localization signal, endoplasmic reticulum localization signal, secretion signal, mitochondrial localization signal, and the like. The nucleic acid can comprise a nucleic acid sequence encoding for a plurality of signal peptides.

Vectors can be introduced into cells. A cell or host cell can generally refer to a cell used in the methods of the disclosure. A cell can be a cell from a mammal (e.g., rat, mouse, primate, human). A cell can be a eukaryotic cell. A cell can be from a vertebrate (e.g., dog, chicken, cow). A cell can be a mouse myeloma hybridoma cell. The cell can be a Chinese hamster ovary (CHO) cell. A cell can be a genetically modified cell. A cell can be a genetically modified cell when it comprises an exogenous polypeptide and/or nucleic acid sequence. An exogenous polypeptide and/or nucleic acid sequence can be inserted into the cell. Methods for insertion can include direct uptake, transduction, transfection, electroporation, and f-mating. The exogenous polynucleotide may be maintained as a nonintegrated vector, for example, a plasmid, or alternatively, may be integrated into the host genome.

A vector may be introduced into a cell by transfection, and/or electroporation. The nucleic acid sequence of the vector may integrate into chromosomal nucleic acid of the cell. The cell can be capable of expressing an immunoglobulin fusion protein.

Owing to the degeneracy of the genetic code, any combination of suitable codons may be used to code for the desired fusion protein. In addition, all nucleic acid sequences described and claimed herein can include the complement of the sequence.

Methods of Manufacture

A method for the manufacture of a fusion antibody can comprise stably integrating into a cell a single tandem expression vector encoding: (i) both an immunoglobulin heavy chain fused to a polypeptide sequence, and an immunoglobulin light chain; or (ii), both an immunoglobulin light chain fused to a polypeptide sequence, and an immunoglobulin heavy chain, where the encoded immunoglobulin heavy chain and immunoglobulin light chain are from an antibody against a receptor expressed on the BBB.

A cell line can be permanently transfected with a single plasmid DNA that comprises all the required genes to produce the fusion antibody on a single strand of DNA.

The fusion antibody can be expressed, and/or purified from the cell. Purification can be performed by methods such as, affinity purification, ammonium sulfate precipitation, ion exchange, size exclusion chromatography, and the like.

A fusion antibody can be synthesized with methods in protein synthesis, such as manual or automated solid phase synthesis, chemical synthesis, which can join the amino acids in the predetermined sequence starting at the C-terminus. Basic solid phase methods can require coupling the C-terminal protected α-amino acid to a suitable insoluble resin support. Amino acids for synthesis can require protection on the α-amino group to ensure proper peptide bond formation with the preceding residue (or resin support). Following completion of the condensation reaction at the carboxyl end, the α-amino protecting group can be removed to allow the addition of the next residue. α-protecting groups can include acid labile, urethane-based tertiary-butyloxycarbonyl (Boc), and 9-fluorenylmethyloxycarbonyl (FMOC) α-protecting groups. The reactive amino acid side chain functional groups can require blocking until the synthesis is completed.

Solid phase synthesis can be initiated by the coupling of the described C-terminal α-protected amino acid residue. Coupling can require activating agents, such as dicyclohexycarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the α-amino protected group can be removed by trifluoroacetic acid (25% or greater) in dichloromethane in the case of acid labile tertiary-butyloxycarbonyl (Boc) groups. A neutralizing step with triethylamine (10%) in dichloro-methane recovers the free amine (versus the salt). After the C-terminal residue is added to the resin, the cycle of deprotection, neutralization and coupling, with intermediate wash steps, can be repeated in order to extend the protected peptide chain. Each protected amino acid can be introduced in excess (three to five fold) with equimolar amounts of coupling reagent in suitable solvent. Finally, after the completely blocked peptide is assembled on the resin support, reagents can be applied to cleave the peptide form the resin and to remove the side chain blocking groups. Anhydrous hydrogen fluoride (HF) can cleave the acid labile tertiary-butyloxycarbonyl (Boc) chemistry groups. Several nucleophilic scavengers, such as dimethylsulfide and anisole, can be included to avoid side reactions especially on side chain functional groups.

Kits

In some cases, this disclosure provides a variety of kits. Kits can comprise a structure (e.g., fusion antibody) and a substance (e.g., monosaccharide). In some instances, the substance is dextrose. In some instances, the substance is glucose. In some instances, the kit comprises an IDUA-fusion structure. In some instances, the kit comprises a IDS-fusion structure.

A kit can comprise a suitable buffer. A buffer can be used for reconstituting, diluting, or stabilizing the structure and/or substance. In some cases, the buffer is a saline solution or other buffer known in the art or described herein. The buffer may comprise a structure (e.g., fusion antibody) and/or a substance (e.g., monosaccharide). Exemplary concentrations of structures and substances are provided elsewhere herein.

A kit can comprise instructions for use. Instructions can be electronic (e.g., CD-ROM, cloud). In some cases, the instructions are provided in written form, e.g., on a sheet of paper, or on a box holding the kit ingredients.

A kit can comprise a vector comprising a polynucleotide sequence encoding a structure (e.g., antibody, fusion antibody, polypeptide). In some instances, the kit can comprise a vector comprising a sequence encoding an IDS-fusion structure. In some instances, the kit can comprise a vector comprising a polynucleotide sequence encoding an IDUA-fusion structure.

A kit can comprise a composition of the disclosure. In some instances, the composition can be an IDS-fusion structure and a substance. In some instances, a composition can be an IDUA-fusion structure and a substance.

As used throughout this Specification, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Change in Plasma Glucose Levels without Glucose Supplement

An experiment was performed to determine plasma glucose levels after HIRMAb-IDUA treatment without a glucose supplement.0

Juvenile Rhesus monkeys (*Macaca mulatta*) of mixed sex (20 males, 20 females) were used for all examples, and were housed at MPI Research, Inc. (Mattawan, Mich.) in stainless steel cages in a controlled environment (18 to 28° C. and 30-70% relative humidity) on a 12-h light/dark cycle. Lab Diet Certified Primate Diet (PMI Nutrition International) was provided twice daily. Animals were fasting prior to all drug infusions, as food was withheld the morning prior to drug infusion. Tap water was provided ab libitum. All aspects of the primate study performed at MPI Research was conducted in strict compliance with the United States Food and Drug Administration Good Laboratory Practice (GLP) Regulations, 21 CFR Part 58. All procedures were in compliance with the Animal Welfare Act Regulations, and were approved by the Institutional Animal Care and Use Committee.

The primates were treated with 0 mg/kg (6 males, 6 females), 3 mg/kg (4 males, 4 females), 9 mg/kg (4 males, 4 females), or 30 mg/kg (6 males, 6 females) of the HIRMAb-IDUA fusion protein administered as an intravenous infusion over a 30-min period in 50 mL of either normal saline or 10% dextrose in normal saline. In the 26-week toxicity study, the doses were administered every 7 days for 26 consecutive weeks. The HIRMAb-IDUA fusion protein was administered on a weekly basis. For drug infusion at week 1 and week 25, blood was removed from the femoral vein and collected in tubes with K2-EDTA at 0, 2, 5, 30, 35, 90 min, 3, 6, 23 hrs after the start of the 30 min IV infusion of the HIRMAb-IDUA fusion protein. The blood was separated into plasma which was then stored at −70 C until analysis. Fasting plasma glucose was measured monthly during the study. During the first week, CSF was removed via the cisterna magna at 0, 3, and 23 hrs after the IV infusion of the HIRMAb-IDUA fusion protein. Fasting plasma glucose was measured on blood removed at weeks 0, 4, 8, 13, 16, 20, and 24.

Plasma glucose levels were determined at MPI Research, Inc. (Mattawan, Mich.) with an Olympus AU2700 Chemistry Analyzer (Olympus America, Inc., Melville, N.Y.). CSF glucose was determined with the Glucose Assay Kit from BioVision, Inc. (San Francisco, Calif.) using a spectrophotometric method and absorbance at 570 nm. The assay is run in 96-well plates with a standard curve of D-glucose of 0 to 10 nmol/well, and 50 uL samples per well of a 1:50 dilution of primate CSF.

Figure 3:
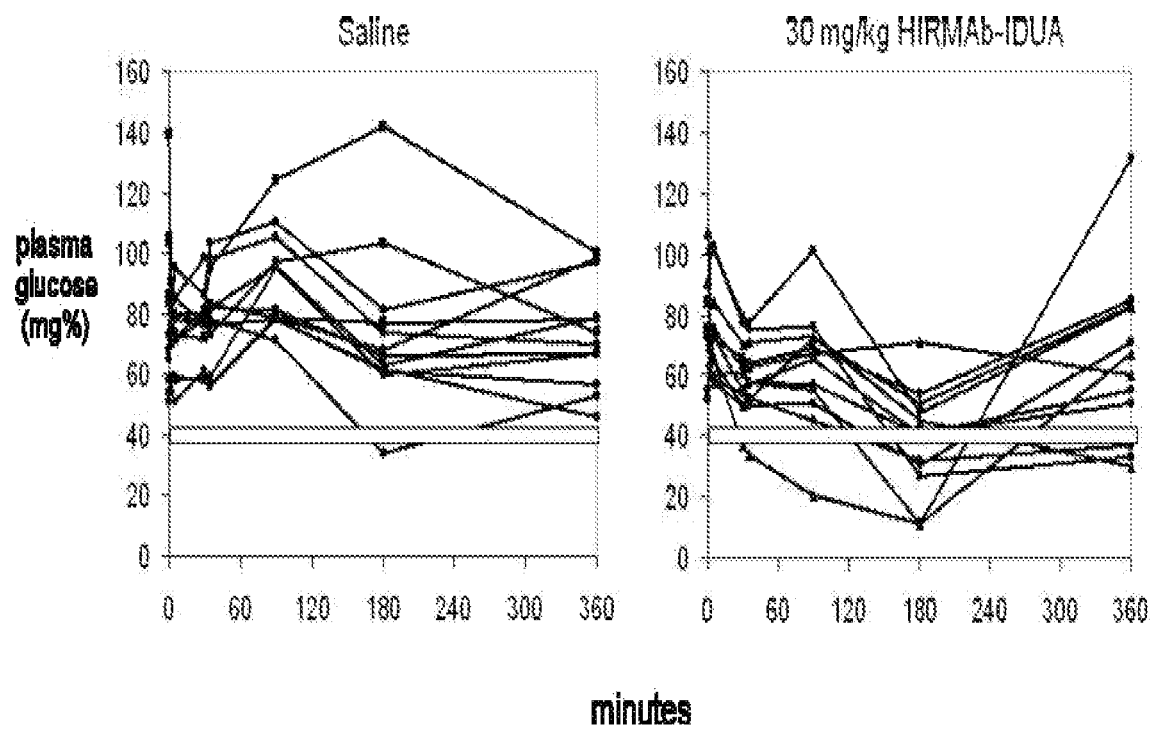
FIG. 3 depicts changes in plasma glucose levels over time without supplemental glucose.

The HIRMAb-IDUA fusion protein was IV infused over 30 min in 50 mL normal saline in Rhesus monkeys at 4 doses (0, 3, 9, 30 mg/kg). Plasma glucose was measured at 0, 2, 5, 30, 35, 90, 180, 360, and 1380 min after the start of the 30 min infusion, and the values are reported in Table 1 either by sex or combined sexes. There were no significant differences between sexes at any time point. The glucose in the fusion protein treated animals (combined sexes) was 20-29% lower than the saline controls at 30 and 35 minutes after start of the 30 min drug infusion at all 3 doses of fusion protein with no dose relationships. The plasma glucose was decreased 31% and 47% at 90 and 180 minutes only in the high dose group, 30 mg/kg. FIG. 3 shows the plasma glucose for individual monkeys in the saline group and in the high dose group (30 mg/kg). Plasma glucose levels were plotted vs. time after the start of a 30 min infusion of the HIRMAb-IDUA fusion antibody at a dose of either 0 mg/kg (left panel) or 30 mg/kg (right panel). Data are shown for individual monkeys (6 males and 6 females in each treatment group). The horizontal bar defines a plasma glucose of 40 mg %, which was a minimum value for all but one of the saline-infused monkeys.

One monkey in the saline and 4 monkeys in the 30 mg/kg group had plasma glucose values <40 mg % and the nadir is at 180 minutes after the start of the 30 min infusion. The level of hypoglycemia in 2 monkeys at 180 minutes was severe with plasma glucose values of 11 mg % following the IV infusion of the HIRMAb-IDUA fusion protein in normal saline at a dose of 30 mg/kg.

TABLE 1

Plasma glucose at start of study

| | | HIRMAb-IDUA injection dose | | | |
|---|---|---|---|---|---|
| minutes | sex | 0 mg/kg | 3 mg/kg | 9 mg/kg | 30 mg/kg |
| 0 | combined | 83 ± 7 | 74 ± 4 | 70 ± 5 | 78 ± 4 |
| 2 | | 73 ± 3 | 67 ± 7 | 67 ± 3 | 75 ± 4 |
| 5 | | 74 ± 4 | 64 ± 7 | 64 ± 3 | 74 ± 4 |
| 30 | | 75 ± 3 | 55 ± 6$^b$ | 57 ± 4$^a$ | 60 ± 3$^a$ |
| 35 | | 79 ± 5 | 56 ± 5$^b$ | 59 ± 4$^a$ | 59 ± 3$^b$ |

TABLE 1-continued

Plasma glucose at start of study

| | | HIRMAb-IDUA injection dose | | | |
|---|---|---|---|---|---|
| minutes | sex | 0 mg/kg | 3 mg/kg | 9 mg/kg | 30 mg/kg |
| 90 | | 91 ± 5 | 75 ± 5 | 72 ± 4 | 63 ± 6[b] |
| 180 | | 74 ± 8 | 58 ± 5 | 61 ± 3 | 39 ± 5[b] |
| 360 | | 74 ± 5 | 72 ± 12 | 79 ± 11 | 65 ± 8 |
| 1380 | | 76 ± 5 | 79 ± 8 | 69 ± 5 | 70 ± 8 |
| 0 | male | 75 ± 7 | 81 ± 6 | 72 ± 6 | 79 ± 7 |
| 2 | | 75 ± 4 | 78 ± 5 | 65 ± 7 | 70 ± 4 |
| 5 | | 76 ± 4 | 74 ± 6 | 62 ± 5 | 69 ± 4 |
| 30 | | 74 ± 3 | 58 ± 2 | 56 ± 6[a] | 57 ± 3[a] |
| 35 | | 75 ± 4 | 60 ± 3 | 59 ± 7 | 58 ± 3[a] |
| 90 | | 86 ± 5 | 81 ± 6 | 75 ± 4 | 62 ± 4[b] |
| 180 | | 65 ± 9 | 69 ± 4 | 59 ± 6 | 37 ± 6[b] |
| 360 | | 66 ± 4 | 58 ± 5 | 89 ± 10 | 70 ± 14 |
| 1380 | | 75 ± 10 | 89 ± 8 | 64 ± 5 | 70 ± 12 |
| 0 | female | 90 ± 13 | 68 ± 5 | 69 ± 9 | 77 ± 6 |
| 2 | | 70 ± 5 | 55 ± 9 | 69 ± 3 | 80 ± 7 |
| 5 | | 72 ± 7 | 54 ± 12 | 67 ± 3 | 79 ± 7 |
| 30 | | 77 ± 6 | 52 ± 12 | 59 ± 4 | 63 ± 6 |
| 35 | | 82 ± 9 | 52 ± 11 | 60 ± 5 | 61 ± 6 |
| 90 | | 96 ± 8 | 69 ± 9 | 70 ± 7 | 63 ± 11 |
| 180 | | 84 ± 12 | 47 ± 7 | 64 ± 2 | 41 ± 9[a] |
| 360 | | 82 ± 9 | 87 ± 22 | 68 ± 20 | 61 ± 9 |
| 1380 | | 76 ± 5 | 69 ± 12 | 75 ± 8 | 69 ± 13 |

Data are mg/dL. Mean ± SE (n = 8-12 per group in combined sexes, and 4-6 per group in male or female groups).
[a]P < 0.05 difference from 0 mg/kg by ANOVA.
[b]P < 0.01 difference from 0 mg/kg by ANOVA.

Example 2

Change in Plasma Glucose Levels with Glucose Supplement

Figure 4:
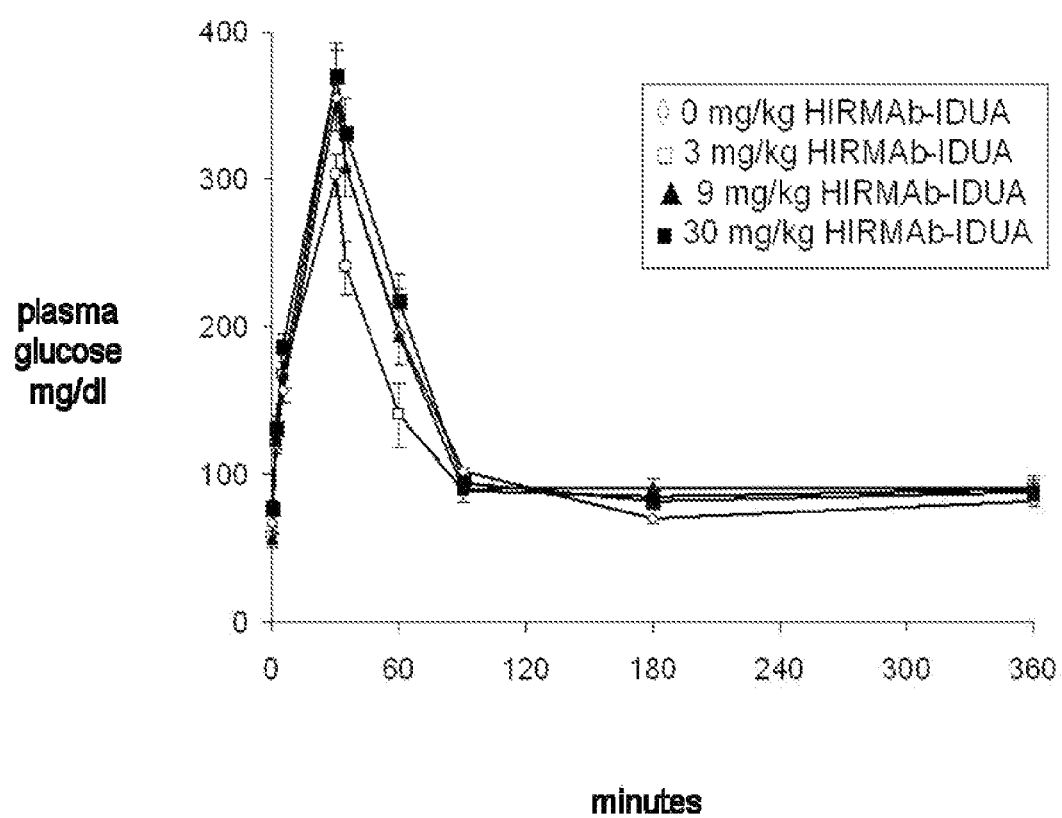
FIG. 4 depicts changes in plasma glucose levels over time with supplemental glucose.

During the last week of the 26-week treatment study, the HIRMAb-IDUA fusion protein was formulated in 50 mL of 10% dextrose/normal saline and infused over 30 minutes in the same group of Rhesus monkeys at doses of 0, 3, 9, and 30 mg/kg. No hypoglycemia was observed in any animal, and the plasma glucose values are shown in FIG. 4. The plasma glucose peaked at the end of the 30 minutes of fusion protein infusion. The rate of decline in the plasma glucose was evaluated by linear regression analysis to produce the half-time ($T_{1/2}$) of glucose clearance from plasma for each of the 4 treatment doses of the HIRMAb-IDUA fusion protein. There were no differences in the $T_{1/2}$ among all treatment groups, and glucose was cleared from plasma with a $T_{1/2}$ of 32-35 minutes (Table 2).

Plasma glucose was measured monthly in all monkeys prior to the IV infusion of the study drug, and the plasma glucose values are shown in Table 3 by sex and for combined groups. There were no sex differences and no upward or downward trend in plasma glucose over the course of 24 weeks.

TABLE 2

Intravenous glucose tolerance test at end of 26-week dosing

| para- | | HIRMAb-IDUA dose (mg/kg) | | | |
|---|---|---|---|---|---|
| meter | units | 0 | 3 | 9 | 30 |
| k | min⁻¹ | 0.020 ± 0.001 | 0.022 ± 0.003 | 0.022 ± 0.002 | 0.021 ± 0.002 |
| T½ | min | 35 ± 2 | 32 ± 4 | 32 ± 3 | 33 2 |

Parameters determined by non-linear regression analysis of the plasma glucose between 30 and 90 minutes after a 30 min infusion of 10% glucose. Data are means±SE for combined sexes. T½=half-time of glucose clearance from blood after termination of the glucose infusion.

TABLE 3

Plasma glucose by week of study

| | | HIRMAb-IDUA injection dose | | | |
|---|---|---|---|---|---|
| weeks | sex | 0 mg/kg | 3 mg/kg | 9 mg/kg | 30 mg/kg |
| 0 | combined | 83 ± 7 | 74 ± 4 | 70 ± 5 | 78 ± 5 |
| 4 | | 77 ± 2 | 77 ± 5 | 79 ± 7 | 72 ± 3 |
| 8 | | 86 ± 4 | 79 ± 4 | 78 ± 7 | 79 ± 3 |
| 13 | | 77 ± 3 | 76 ± 4 | 77 ± 4 | 78 ± 6 |
| 16 | | 76 ± 3 | 70 ± 5 | 70 ± 6 | 79 ± 6 |
| 20 | | 72 ± 5 | 68 ± 5 | 71 ± 5 | 78 ± 5 |
| 24 | | 73 ± 2 | 72 ± 5 | 81 ± 7 | 80 ± 4 |
| 0 | male | 75 ± 7 | 81 ± 6 | 72 ± 6 | 79 ± 7 |
| 4 | | 79 ± 3 | 81 ± 4 | 84 ± 12 | 67 ± 5 |
| 8 | | 88 ± 6 | 81 ± 2 | 79 ± 8 | 83 ± 7 |
| 13 | | 76 ± 2 | 79 ± 3 | 76 ± 6 | 76 ± 6 |
| 16 | | 80 ± 6 | 73 ± 3 | 72 ± 9 | 74 ± 6 |
| 20 | | 77 ± 7 | 65 ± 4 | 71 ± 7 | 75 ± 4 |
| 24 | | 72 ± 1 | 67 ± 4 | 87 ± 15 | 76 ± 4 |
| 0 | female | 90 ± 13 | 68 ± 5 | 69 ± 9 | 77 ± 6 |
| 4 | | 76 ± 2 | 73 ± 10 | 74 ± 7 | 77 ± 5 |
| 8 | | 84 ± 6 | 77 ± 9 | 78 ± 12 | 76 ± 3 |
| 13 | | 78 ± 6 | 73 ± 8 | 77 ± 7 | 81 ± 11 |
| 16 | | 73 ± 2 | 69 ± 9 | 68 ± 8 | 84 ± 10 |
| 20 | | 67 ± 8 | 71 ± 9 | 70 ± 6 | 81 ± 11 |
| 24 | | 74 ± 4 | 76 ± 9 | 76 ± 6 | 84 ± 7 |

Data are mg/dL. Mean ± SE (n = 8-12 per group in combined sexes, and 4-6 per group in male or female groups). Blood was removed for plasma glucose 1 week following the previous dosing of study drug.

Example 3

Figure 5:
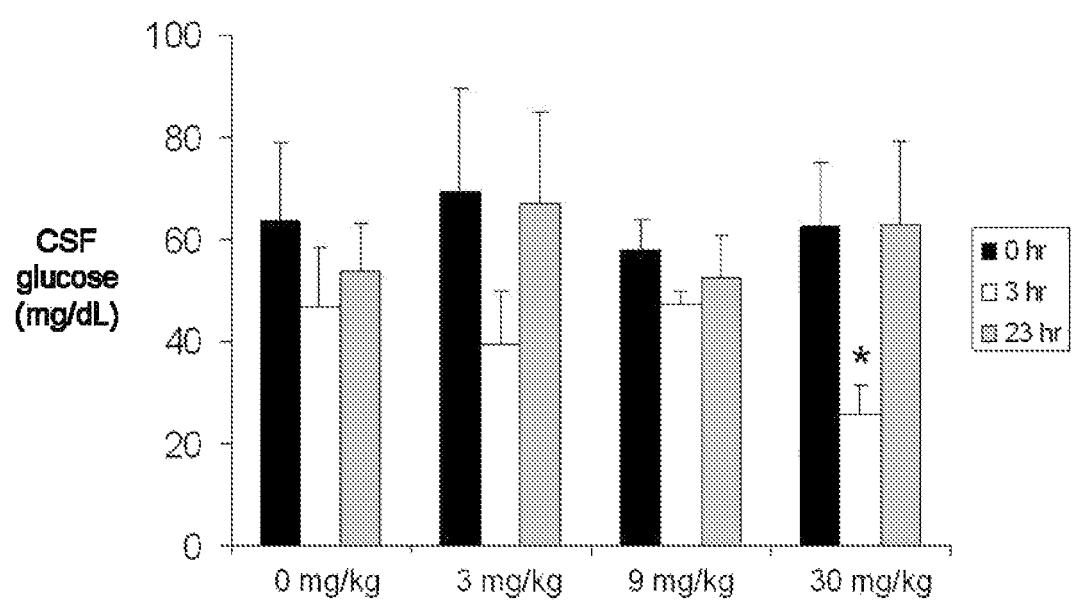
FIG. 5 depicts CSF glucose levels without supplemental glucose.

Monitor Csf Glucose Levels and Comparison of Csf and Plasma Glucose Levels without Glucose Supplement Glucose was measured in CSF at 0, 3, and 23 hours after the 30 min infusion of HIRMAb-IDUA fusion protein at each of the 4 doses (0, 3, 9, and 30 mg/kg) in normal saline (e.g., without glucose supplement). Data are shown in FIG. 5. Data are shown as mean±SE (n=8-12 combined sexes in each group). *P<0.05 difference from control (0 mg/kg) as determined by ANOVA. The only significant difference in CSF glucose was a 48% decrease at 3 hours in the 30 mg/kg treatment group (FIG. 5).

Figure 6:
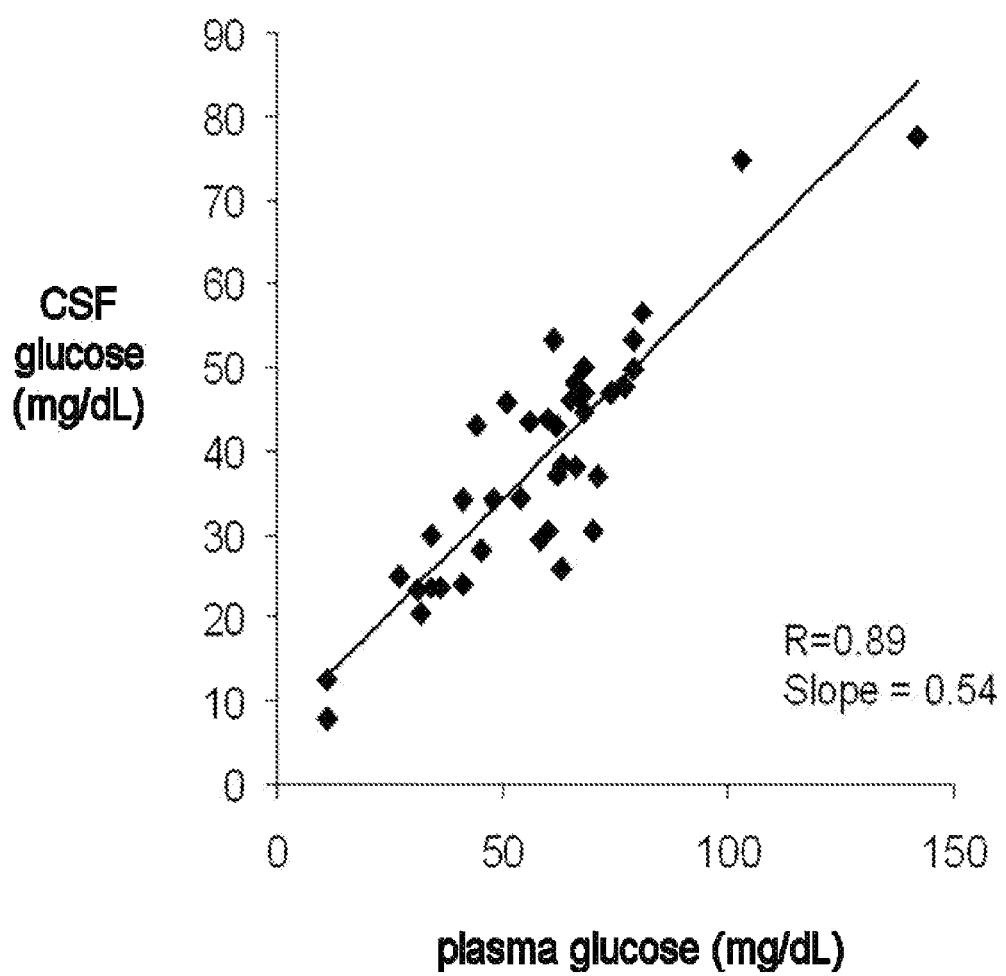
FIG. 6 compares plasma and CSF glucose without supplemental glucose.

The CSF glucose, at 3 hours after drug infusion, in all 40 monkeys in the study correlated with the plasma glucose, at 3 hours after drug infusion, and the average CSF/plasma glucose ratio was 54% for all monkeys (FIG. 6). FIG. 6, shows CSF glucose plotted vs the corresponding plasma glucose at 3 hours after the IV infusion of HIRMAb-IDUA fusion antibody for all 4 treatment groups (0, 3, 9, 30 mg/kg). Data for individual monkeys is shown. The slope was determined by linear regression analysis. CSF and plasma glucose were determined following HIRMAb-IDUA infusion during the first week of the study.

There were no significant differences in the glucose concentration in CSF at 0 and 23 hours in any of the 4 treatment groups. The CSF glucose at 0 hours was 63±16, 69±20, 58±6, and 62±12 mg %, and at 23 hours was 54±9, 67±18, 52±8, and 63±16 mg %, respectively after administration of 0, 3, 9, and 23 mg/kg HIRMAb-IDUA fusion protein (mean±S.D.).

The results of the studies are consistent with the following conclusions. First, high doses, 30 mg/kg, of the HIRMAb-IDUA fusion protein in fasting Rhesus monkeys caused hypoglycemia with a nadir of 39±5 mg % at 180 min after a 30 min infusion of the fusion protein in 50 mL of normal saline (Table 1). Second, the hypoglycemia was severe in some monkeys as the nadir was as low as 11 mg % in 2 monkeys at the 30 mg/kg dose of fusion protein (FIG. 3). Third, the hypoglycemia was eliminated by the inclusion of glucose in the infusion solution (FIG. 4). Fourth, the rate of clearance of glucose from plasma, which is a measure of glucose tolerance, was unchanged in all treatment groups at the end of the 26 weeks of fusion protein dosing (FIG. 4), and the half-time of glucose clearance at all doses in the same, 32-35 minutes (Table 2). Fifth, there was no evidence of impaired glucose tolerance with chronic fusion protein treatment, as the monthly fasting plasma glucose is unchanged in all treatment groups over the course of the 6 months of treatment (Table 3). Sixth, the CSF glucose was decreased at 3 hours after IV infusion of the 30 mg/kg of the HIRMAb-IDUA fusion protein in normal saline, and the CSF glucose parallels the corresponding plasma glucose in each monkey (FIG. 6).

A monoclonal antibody against the alpha-subunit of the human insulin receptor may have either agonist or antagonist properties. Antibodies against the insulin receptor that demonstrate agonist properties cause an increase in glucose uptake by cells, which can be associated with an increase in glucose clearance from plasma. The HIRMAb domain of the HIRMAb-IDUA fusion protein showed agonist properties, albeit only at the highest treatment dose of 30 mg/kg. At this dose, hypoglycemia was induced, which peaked at 3 hours after a 30 min infusion of the HIRMAb-IDUA fusion protein in normal saline (Table 1, FIG. 3). The hypoglycemia was eliminated when glucose was added to the fusion protein infusion solution (FIG. 4). An insulin receptor antibody with antagonist action can cause hyperglycemia and impaired glucose tolerance. The HIRMAb domain of the HIRMAb-IDUA fusion protein exhibited no antagonist properties, as fasting hyperglycemia was not induced (Table 3), and the rate constant of glucose clearance from plasma was unchanged (Table 2) after 6 months of weekly dosing of the fusion protein at doses of 3, 9, or 30 mg/kg. The lack of an effect of chronic treatment with the HIRMAb fusion protein on glycemic control was not due to a change in exposure over the course of 6 months of treatment. A pharmacokinetics analysis showed there was no change in the rate of clearance of the HIRMAb-IDUA fusion protein from blood at the start (week 1) and end (week 25) of the 6 months of treatment. The concentration of glucose in CSF was also reduced at 3 hours after the IV infusion of the HIRMAb-IDUA fusion protein at a dose of 30 mg/kg in normal saline (FIG. 5).

Insulin may not affect glucose uptake by brain, and the CSF glucose was regulated by the plasma glucose concentration. The direct relationship between CSF and plasma glucose was demonstrated (FIG. 6), and the mean CSF/plasma glucose ratio was 0.54 (FIG. 6). This value was in agreement with the CSF/plasma ratio reported in either humans or Rhesus monkeys, which is 0.5-0.6. Therefore, high doses of the HIRMAb-IDUA fusion protein had no direct effect on glucose distribution in CSF, and CSF glucose concentrations paralleled the corresponding concentration of glucose in plasma. Reductions in plasma and CSF glucose were observed at 3 hours after HIRMAb-IDUA infusion only at the high dose of 30 mg/kg. Reductions in glucose in either plasma or CSF were not observed after 3 or 9 mg/kg doses of the fusion protein.

Lower doses of HIRMAb-IDUA fusion protein did not cause hypoglycemia. There were only modest reductions in glucose at 0-5 minutes after termination of the 30 minute infusion, and no significant reductions in plasma glucose at 90-1380 min after the start of the 30 minute IV infusion of 3 or 9 mg/kg doses of the HIRMAb-IDUA fusion protein in normal saline (Table 1). Together, these examples suggest that the HIRMAb domain of the HIRMAb-IDUA fusion protein had weak insulin agonist properties that were observed only at the highest dose of 30 mg/kg. Hypoglycemia was not observed following the administration of doses lower than 30 mg/kg. Any concern about hypoglycemia was mitigated by simply adding dextrose to the saline infusion of drug. The examples show that a 10% dextrose additive was not necessary, as this dose of glucose caused transient hyperglycemia (FIG. 4). A preferred formulation is normal saline with 5% dextrose for routine administration of HIRMAb-derived fusion proteins.

Prophetic Example 5

Administration of Fusion Antibody to Treat a Central Nervous System Disorder

Plasma glucose will be measured monthly in all humans prior to the IV infusion of the fusion antibodies. In some instances, the disclosure provides for methods of administering to a subject a fusion antibody and a monosaccharide. An IDS-fusion antibody will be administered to a subject suffering from CNS disorder such as Hunter's syndrome. A IDUA-fusion antibody will be administered to a subject suffering from a CNS disorder such as Hurler's syndrome. Administration will be performed systemically or peripherally (e.g., intravenous, intra-arterial, subcutaneous, intramuscular, intraperitoneal, transdermal, by inhalation, trans-buccal, intranasal, rectal, oral, parenteral, sublingual, or trans-nasal administration).

The HIRMAb-IDUA or HIRMAb-IDS fusion protein will be infused IV over 30 min in 50 mL normal saline in humans at 1 mg/kg). Plasma and CSF glucose levels will be measured at 0, 2, 5, 30, 35, 90, 180, 360, and 1380 min after the start of the 30 min infusion, and the values will be reported either by sex or combined sexes.

If plasma and CSF glucose levels change significantly to indicate hypoglycemia, the fusion antibody will be administered with a solution of dextrose at least about 5% or 10% dextrose. Plasma and CSF glucose levels will be monitored at numerous time points to assess the impact of dextrose on treating the hypoglycemia. Administration of the fusion antibody either in the presence of normal saline or dextrose will be assessed for a therapeutic effect on the central nervous system disorder of the subject.

In some embodiments, the fusion antibodies will be used as part of a study. In some embodiments, the study will comprise IV infusion of a fusion antibody (e.g., HIRMAb-IDUA, HIRMAb-IDS) over 30 min in 50 mL normal saline in humans at 4 doses (0, 1, 3, 9 mg/kg). Plasma and CSF glucose levels will be measured at 0, 2, 5, 30, 35, 90, 180, 360, and 1380 min after the start of the 30 min infusion, and the values will be reported either by sex or combined sexes. During the last week of a 26-week treatment study, the HIRMAb-IDUA fusion antibody or HIRMAb-IDS fusion antibody will be formulated in 50 mL of either 5% or 10% dextrose/normal saline and infused over 30 minutes in the same group of humans at doses of 0, 1, 3, and 9 mg/kg. Plasma glucose will be measured at 0, 2, 5, 30, 35, 90, 180, 360, and 1380 min after the start of the 30 min infusion, and the values will be reported either by sex or combined sexes. The subjects receiving solutions of normal saline, 5% dextrose, and 10% dextrose will be compared for their effect on glucose levels and induction of transient hypo- or hyperglycemia. The rate of decline in the plasma glucose will be evaluated by linear regression analysis to produce the half-time ($T_{1/2}$) of glucose clearance from plasma for each of the 4 treatment doses of the HIRMAb-IDUA or HIRMAb-IDS fusion antibody.

Glucose can be measured in CSF at 0, 3, and 23 hours after the 30 min infusion of HIRMAb-IDUA or HIRMAb-IDS fusion antibody at each of the 4 doses (0, 1, 3, and 9 mg/kg) in normal saline (e.g., without glucose supplement) and in 5% and 10% dextrose. CSF glucose levels will be compared between the infusions with or normal saline, 5%, and 10% dextrose. Administration of the fusion antibody either in the presence of normal saline or dextrose will be assessed for a therapeutic effect on the central nervous system disorder of the subject.

What is claimed is:

1. A method for treating a subject with a central nervous system (CNS) disorder, wherein the disorder is selected from the group consisting of Hurler's Syndrome, Hunter's Syndrome, Type I mucopolysaccharidosis, Type II mucopolysaccharidosis, and a lysosomal storage disorder, the method comprising administering to the subject:
   a. a structure that binds to a receptor expressed on the blood brain barrier (BBB), wherein the structure comprises HIRMab; and
   b. a glucose monosaccharide;
   wherein the administering treats the subject having the CNS disorder.

2. The method of claim 1, wherein the structure is a fusion antibody.

3. The method of claim 2, wherein the fusion antibody binds to a receptor expressed on the BBB.

4. The method of claim 3, wherein the receptor expressed on the BBB is an insulin receptor.

5. The method of claim 1, wherein the structure is a fusion antibody comprising: an amino acid sequence of a heavy chain immunoglobulin covalently linked to an amino acid sequence of a polypeptide or an amino acid sequence of a light chain immunoglobulin covalently linked to an amino acid sequence of a polypeptide.

6. The method of claim 5, wherein the polypeptide comprises an enzyme.

7. The method of claim 5, wherein the fusion antibody acts as an agonist.

8. The method of claim 1, wherein the glucose monosaccharide is administered to the subject after the structure is administered to the subject.

9. The method of claim 1, wherein the structure causes hypoglycemia.

10. The method of claim 9, wherein the glucose monosaccharide ameliorates the hypoglycemia.

11. A method for treating a subject with a central nervous system (CNS) disorder comprising administering to the subject:
   a. a structure that binds to a receptor expressed on the blood brain barrier (BBB), wherein the structure comprises HIRMab and wherein the structure is a fusion antibody comprising: an amino acid sequence of a heavy chain immunoglobulin covalently linked to an amino acid sequence of a polypeptide which polypeptide comprises a lysosomal enzyme or an amino acid sequence of a light chain immunoglobulin covalently linked to an amino acid sequence of a polypeptide which polypeptide comprises a lysosomal enzyme; and
   b. a glucose monosaccharide;
   wherein the administering treats the subject having the CNS disorder.

12. The method of claim 11, wherein the lysosomal enzyme is selected from the group consisting of: alpha-iduronidase, iduronate-2 sulfatase, and aryl sulfatase.

13. A method for treating a subject with a central nervous system (CNS) disorder comprising administering to the subject:
   a. a structure that binds to a receptor expressed on the blood brain barrier (BBB), wherein the structure comprises HIRMab; and
   b. a glucose monosaccharide;
   wherein the glucose monosaccharide and the structure are present in a same solution and wherein the administering treats the subject having the CNS disorder.

14. The method of claim 13, wherein the solution comprises greater than 5% monosaccharide.

15. A method for treating a subject with a central nervous system (CNS) disorder, wherein the disorder is selected from the group consisting of Hurler's Syndrome, Hunter's Syndrome, Type I mucopolysaccharidosis, Type II mucopolysaccharidosis, and a lysosomal storage disorder, the method comprising administering to the subject:
   a. a structure that binds to a receptor expressed on the blood brain barrier (BBB), wherein the structure comprises HIRMab; wherein the structure is a fusion antibody comprising: an amino acid sequence of a heavy chain immunoglobulin covalently linked to an amino acid sequence of a polypeptide which polypeptide comprises a lysosomal enzyme or an amino acid sequence of a light chain immunoglobulin covalently linked to an amino acid sequence of a polypeptide which polypeptide comprises a lysosomal enzyme; and wherein the lysosomal enzyme is selected from the group consisting of: alpha-iduronidase, iduronate-2 sulfatase, and aryl sulfatase; and
   b. a glucose monosaccharide;
   wherein the glucose monosaccharide and the structure are present in a same solution,
   wherein the solution comprises greater than 5% monosaccharide, and wherein the administering treats the subject having the CNS disorder.

* * * * *

SEQUENCE LISTING

```
<160> NUMBER OF SEQ ID NOS: 8

<210> SEQ ID NO 1
<211> LENGTH: 462
<212> TYPE: PRT
<213> ORGANISM: Homo sapiens

<400> SEQUENCE: 1

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
                20                  25                  30

Pro Gly Ala Leu Val Lys Ile Ser Cys Lys Ala Ser Gly Tyr Thr Phe
            35                  40                  45

Thr Asn Tyr Asp Ile His Trp Val Lys Gln Arg Pro Gly Gln Gly Leu
        50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285
```

```
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
                340                 345                 350
Lys Ala Lys Gly Gln Pro Arg Glu Pro Gln Val Tyr Thr Leu Pro Pro
            355                 360                 365
Ser Arg Asp Glu Leu Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
    450                 455                 460

<210> SEQ ID NO 2
<211> LENGTH: 234
<212> TYPE: PRT
<213> ORGANISM: Homo sapiens

<400> SEQUENCE: 2

Met Glu Thr Pro Ala Gln Leu Leu Phe Leu Leu Leu Leu Trp Leu Pro
1               5                   10                  15
Asp Thr Thr Gly Asp Ile Gln Met Thr Gln Ser Pro Ser Ser Leu Ser
            20                  25                  30
Ala Ser Leu Gly Glu Arg Val Ser Leu Thr Cys Arg Ala Ser Gln Asp
        35                  40                  45
Ile Gly Gly Asn Leu Tyr Trp Leu Gln Gln Gly Pro Asp Gly Thr Ile
    50                  55                  60
Lys Arg Leu Ile Tyr Ala Thr Ser Ser Leu Asp Ser Gly Val Pro Lys
65                  70                  75                  80
Arg Phe Ser Gly Ser Arg Ser Gly Ser Asp Tyr Ser Leu Thr Ile Ser
                85                  90                  95
Ser Leu Glu Ser Glu Asp Phe Val Asp Tyr Tyr Cys Leu Gln Tyr Ser
            100                 105                 110
Ser Ser Pro Trp Thr Phe Gly Gly Gly Thr Lys Met Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
```

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 3
<211> LENGTH: 627
<212> TYPE: PRT
<213> ORGANISM: Homo sapiens

<400> SEQUENCE: 3

Glu Ala Pro His Leu Val Gln Val Asp Ala Arg Ala Leu Trp Pro
1               5                   10                  15

Leu Arg Arg Phe Trp Arg Ser Thr Gly Phe Cys Pro Pro Leu Pro His
            20                  25                  30

Ser Gln Ala Asp Gln Tyr Val Leu Ser Trp Asp Gln Leu Asn Leu
            35                  40                  45

Ala Tyr Val Gly Ala Val Pro His Arg Gly Ile Lys Gln Val Arg Thr
    50                  55                  60

His Trp Leu Leu Glu Leu Val Thr Thr Arg Gly Ser Thr Gly Arg Gly
65                  70                  75                  80

Leu Ser Tyr Asn Phe Thr His Leu Asp Gly Tyr Leu Asp Leu Leu Arg
                85                  90                  95

Glu Asn Gln Leu Leu Pro Gly Phe Glu Leu Met Gly Ser Ala Ser Gly
                100                 105                 110

His Phe Thr Asp Phe Glu Asp Lys Gln Gln Val Phe Glu Trp Lys Asp
            115                 120                 125

Leu Val Ser Ser Leu Ala Arg Arg Tyr Ile Gly Arg Tyr Gly Leu Ala
130                 135                 140

His Val Ser Lys Trp Asn Phe Glu Thr Trp Asn Glu Pro Asp His His
145                 150                 155                 160

Asp Phe Asp Asn Val Ser Met Thr Met Gln Gly Phe Leu Asn Tyr Tyr
                165                 170                 175

Asp Ala Cys Ser Glu Gly Leu Arg Ala Ala Ser Pro Ala Leu Arg Leu
            180                 185                 190

Gly Gly Pro Gly Asp Ser Phe His Thr Pro Pro Arg Ser Pro Leu Ser
        195                 200                 205

Trp Gly Leu Leu Arg His Cys His Asp Gly Thr Asn Phe Phe Thr Gly
210                 215                 220

Glu Ala Gly Val Arg Leu Asp Tyr Ile Ser Leu His Arg Lys Gly Ala
225                 230                 235                 240

Arg Ser Ser Ile Ser Ile Leu Glu Gln Glu Lys Val Val Ala Gln Gln
                245                 250                 255

Ile Arg Gln Leu Phe Pro Lys Phe Ala Asp Thr Pro Ile Tyr Asn Asp
            260                 265                 270

Glu Ala Asp Pro Leu Val Gly Trp Ser Leu Pro Gln Pro Trp Arg Ala
        275                 280                 285

Asp Val Thr Tyr Ala Ala Met Val Val Lys Val Ile Ala Gln His Gln
290                 295                 300

Asn Leu Leu Leu Ala Asn Thr Thr Ser Ala Phe Pro Tyr Ala Leu Leu
305                 310                 315                 320

Ser Asn Asp Asn Ala Phe Leu Ser Tyr His Pro His Pro Phe Ala Gln
                325                 330                 335

Arg Thr Leu Thr Ala Arg Phe Gln Val Asn Asn Thr Arg Pro Pro His
            340                 345                 350

Val Gln Leu Leu Arg Lys Pro Val Leu Thr Ala Met Gly Leu Leu Ala
         355                 360                 365

Leu Leu Asp Glu Glu Gln Leu Trp Ala Glu Val Ser Gln Ala Gly Thr
370                 375                 380

Val Leu Asp Ser Asn His Thr Val Gly Val Leu Ala Ser Ala His Arg
385                 390                 395                 400

Pro Gln Gly Pro Ala Asp Ala Trp Arg Ala Ala Val Leu Ile Tyr Ala
             405                 410                 415

Ser Asp Asp Thr Arg Ala His Pro Asn Arg Ser Val Ala Val Thr Leu
         420                 425                 430

Arg Leu Arg Gly Val Pro Pro Gly Pro Gly Leu Val Tyr Val Thr Arg
         435                 440                 445

Tyr Leu Asp Asn Gly Leu Cys Ser Pro Asp Gly Glu Trp Arg Arg Leu
         450                 455                 460

Gly Arg Pro Val Phe Pro Thr Ala Glu Gln Phe Arg Arg Met Arg Ala
465                 470                 475                 480

Ala Glu Asp Pro Val Ala Ala Pro Arg Pro Leu Pro Ala Gly Gly
             485                 490                 495

Arg Leu Thr Leu Arg Pro Ala Leu Arg Leu Pro Ser Leu Leu Leu Val
         500                 505                 510

His Val Cys Ala Arg Pro Glu Lys Pro Pro Gly Gln Val Thr Arg Leu
         515                 520                 525

Arg Ala Leu Pro Leu Thr Gln Gly Gln Leu Val Leu Val Trp Ser Asp
         530                 535                 540

Glu His Val Gly Ser Lys Cys Leu Trp Thr Tyr Glu Ile Gln Phe Ser
545                 550                 555                 560

Gln Asp Gly Lys Ala Tyr Thr Pro Val Ser Arg Lys Pro Ser Thr Phe
             565                 570                 575

Asn Leu Phe Val Phe Ser Pro Asp Thr Gly Ala Val Ser Gly Ser Tyr
         580                 585                 590

Arg Val Arg Ala Leu Asp Tyr Trp Ala Arg Pro Gly Pro Phe Ser Asp
         595                 600                 605

Pro Val Pro Tyr Leu Glu Val Pro Val Pro Arg Gly Pro Pro Ser Pro
         610                 615                 620

Gly Asn Pro
625

<210> SEQ ID NO 4
<211> LENGTH: 1091
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
             20                  25                  30

Pro Gly Ala Leu Val Lys Ile Ser Cys Lys Ala Ser Gly Tyr Thr Phe
         35                  40                  45

Thr Asn Tyr Asp Ile His Trp Val Lys Gln Arg Pro Gly Gln Gly Leu
     50                  55                  60

Glu Trp Ile Gly Trp Ile Tyr Pro Gly Asp Gly Ser Thr Lys Tyr Asn
65                  70                  75                  80

-continued

```
Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Glu Ala Pro His Leu Val Gln Val Asp Ala Ala Arg Ala Leu Trp Pro
465                 470                 475                 480

Leu Arg Arg Phe Trp Arg Ser Thr Gly Phe Cys Pro Pro Leu Pro His
                485                 490                 495
```

```
Ser Gln Ala Asp Gln Tyr Val Leu Ser Trp Asp Gln Leu Asn Leu
            500                 505                 510

Ala Tyr Val Gly Ala Val Pro His Arg Gly Ile Lys Gln Val Arg Thr
        515                 520                 525

His Trp Leu Leu Glu Leu Val Thr Thr Arg Gly Ser Thr Gly Arg Gly
            530                 535                 540

Leu Ser Tyr Asn Phe Thr His Leu Asp Gly Tyr Leu Asp Leu Leu Arg
545                 550                 555                 560

Glu Asn Gln Leu Leu Pro Gly Phe Glu Leu Met Gly Ser Ala Ser Gly
            565                 570                 575

His Phe Thr Asp Phe Glu Asp Lys Gln Gln Val Phe Glu Trp Lys Asp
            580                 585                 590

Leu Val Ser Ser Leu Ala Arg Arg Tyr Ile Gly Arg Tyr Gly Leu Ala
            595                 600                 605

His Val Ser Lys Trp Asn Phe Glu Thr Trp Asn Glu Pro Asp His His
            610                 615                 620

Asp Phe Asp Asn Val Ser Met Thr Met Gln Gly Phe Leu Asn Tyr Tyr
625                 630                 635                 640

Asp Ala Cys Ser Glu Gly Leu Arg Ala Ala Ser Pro Ala Leu Arg Leu
            645                 650                 655

Gly Gly Pro Gly Asp Ser Phe His Thr Pro Arg Ser Pro Leu Ser
            660                 665                 670

Trp Gly Leu Leu Arg His Cys His Asp Gly Thr Asn Phe Phe Thr Gly
            675                 680                 685

Glu Ala Gly Val Arg Leu Asp Tyr Ile Ser Leu His Arg Lys Gly Ala
            690                 695                 700

Arg Ser Ser Ile Ser Ile Leu Glu Gln Glu Lys Val Val Ala Gln Gln
705                 710                 715                 720

Ile Arg Gln Leu Phe Pro Lys Phe Ala Asp Thr Pro Ile Tyr Asn Asp
            725                 730                 735

Glu Ala Asp Pro Leu Val Gly Trp Ser Leu Pro Gln Pro Trp Arg Ala
            740                 745                 750

Asp Val Thr Tyr Ala Ala Met Val Val Lys Val Ile Ala Gln His Gln
            755                 760                 765

Asn Leu Leu Leu Ala Asn Thr Thr Ser Ala Phe Pro Tyr Ala Leu Leu
            770                 775                 780

Ser Asn Asp Asn Ala Phe Leu Ser Tyr His Pro His Pro Phe Ala Gln
785                 790                 795                 800

Arg Thr Leu Thr Ala Arg Phe Gln Val Asn Asn Thr Arg Pro Pro His
            805                 810                 815

Val Gln Leu Leu Arg Lys Pro Val Leu Thr Ala Met Gly Leu Leu Ala
            820                 825                 830

Leu Leu Asp Glu Glu Gln Leu Trp Ala Glu Val Ser Gln Ala Gly Thr
            835                 840                 845

Val Leu Asp Ser Asn His Thr Val Gly Val Leu Ala Ser Ala His Arg
            850                 855                 860

Pro Gln Gly Pro Ala Asp Ala Trp Arg Ala Ala Val Leu Ile Tyr Ala
865                 870                 875                 880

Ser Asp Asp Thr Arg Ala His Pro Asn Arg Ser Val Ala Val Thr Leu
            885                 890                 895

Arg Leu Arg Gly Val Pro Pro Gly Pro Gly Leu Val Tyr Val Thr Arg
            900                 905                 910
```

Tyr Leu Asp Asn Gly Leu Cys Ser Pro Asp Gly Glu Trp Arg Arg Leu
            915                 920                 925

Gly Arg Pro Val Phe Pro Thr Ala Glu Gln Phe Arg Arg Met Arg Ala
930                 935                 940

Ala Glu Asp Pro Val Ala Ala Pro Arg Pro Leu Pro Ala Gly Gly
945                 950                 955                 960

Arg Leu Thr Leu Arg Pro Ala Leu Arg Leu Pro Ser Leu Leu Val
            965                 970                 975

His Val Cys Ala Arg Pro Glu Lys Pro Pro Gly Gln Val Thr Arg Leu
            980                 985                 990

Arg Ala Leu Pro Leu Thr Gln Gly Gln Leu Val Leu Val Trp Ser Asp
            995                 1000                1005

Glu His Val Gly Ser Lys Cys Leu Trp Thr Tyr Glu Ile Gln Phe
    1010                1015                1020

Ser Gln Asp Gly Lys Ala Tyr Thr Pro Val Ser Arg Lys Pro Ser
    1025                1030                1035

Thr Phe Asn Leu Phe Val Phe Ser Pro Asp Thr Gly Ala Val Ser
    1040                1045                1050

Gly Ser Tyr Arg Val Arg Ala Leu Asp Tyr Trp Ala Arg Pro Gly
    1055                1060                1065

Pro Phe Ser Asp Pro Val Pro Tyr Leu Glu Val Pro Val Pro Arg
    1070                1075                1080

Gly Pro Pro Ser Pro Gly Asn Pro
    1085                1090

<210> SEQ ID NO 5
<211> LENGTH: 525
<212> TYPE: PRT
<213> ORGANISM: Homo sapiens

<400> SEQUENCE: 5

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
                100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
        130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

```
Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
            290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
            370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
            515                 520                 525

<210> SEQ ID NO 6
<211> LENGTH: 989
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30
```

```
Pro Gly Ala Leu Val Lys Ile Ser Cys Lys Ala Ser Gly Tyr Thr Phe
             35                  40                  45
Thr Asn Tyr Asp Ile His Trp Val Lys Gln Arg Pro Gly Gln Gly Leu
 50                  55                  60
Glu Trp Ile Gly Trp Ile Tyr Pro Gly Asp Gly Ser Thr Lys Tyr Asn
65                  70                  75                  80
Glu Lys Phe Lys Gly Lys Ala Thr Leu Thr Ala Asp Lys Ser Ser Ser
                 85                  90                  95
Thr Ala Tyr Met His Leu Ser Ser Leu Thr Ser Glu Lys Ser Ala Val
             100                 105                 110
Tyr Phe Cys Ala Arg Glu Trp Ala Tyr Trp Gly Gln Gly Thr Leu Val
             115                 120                 125
Thr Val Ser Ala Ala Ser Thr Lys Gly Pro Ser Val Phe Pro Leu Ala
130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                 165                 170                 175
Ala Leu Thr Ser Gly Val His Thr Phe Pro Ala Val Leu Gln Ser Ser
             180                 185                 190
Gly Leu Tyr Ser Leu Ser Ser Val Val Thr Val Pro Ser Ser Ser Leu
             195                 200                 205
Gly Thr Gln Thr Tyr Ile Cys Asn Val Asn His Lys Pro Ser Asn Thr
             210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                 245                 250                 255
Leu Phe Pro Pro Lys Pro Lys Asp Thr Leu Met Ile Ser Arg Thr Pro
             260                 265                 270
Glu Val Thr Cys Val Val Val Asp Val Ser His Glu Asp Pro Glu Val
             275                 280                 285
Lys Phe Asn Trp Tyr Val Asp Gly Val Glu Val His Asn Ala Lys Thr
290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                 325                 330                 335
Lys Val Ser Asn Lys Ala Leu Pro Ala Pro Ile Glu Lys Thr Ile Ser
             340                 345                 350
Lys Ala Lys Gly Gln Pro Arg Glu Pro Gln Val Tyr Thr Leu Pro Pro
             355                 360                 365
Ser Arg Asp Glu Leu Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                 405                 410                 415
Gly Ser Phe Phe Leu Tyr Ser Lys Leu Thr Val Asp Lys Ser Arg Trp
             420                 425                 430
Gln Gln Gly Asn Val Phe Ser Cys Ser Val Met His Glu Ala Leu His
             435                 440                 445
```

```
Asn His Tyr Thr Gln Lys Ser Leu Ser Leu Ser Pro Gly Ser Ser Ser
    450                 455                 460

Ser Glu Thr Gln Ala Asn Ser Thr Thr Asp Ala Leu Asn Val Leu Leu
465                 470                 475                 480

Ile Ile Val Asp Asp Leu Arg Pro Ser Leu Gly Cys Tyr Gly Asp Lys
                485                 490                 495

Leu Val Arg Ser Pro Asn Ile Asp Gln Leu Ala Ser His Ser Leu Leu
            500                 505                 510

Phe Gln Asn Ala Phe Ala Gln Ala Val Cys Ala Pro Ser Arg Val
        515                 520                 525

Ser Phe Leu Thr Gly Arg Arg Pro Asp Thr Thr Arg Leu Tyr Asp Phe
530                 535                 540

Asn Ser Tyr Trp Arg Val His Ala Gly Asn Phe Ser Thr Ile Pro Gln
545                 550                 555                 560

Tyr Phe Lys Glu Asn Gly Tyr Val Thr Met Ser Val Gly Lys Val Phe
                565                 570                 575

His Pro Gly Ile Ser Ser Asn His Thr Asp Asp Ser Pro Tyr Ser Trp
            580                 585                 590

Ser Phe Pro Tyr His Pro Ser Ser Glu Lys Tyr Glu Asn Thr Lys
        595                 600                 605

Thr Cys Arg Gly Pro Asp Gly Glu Leu His Ala Asn Leu Leu Cys Pro
610                 615                 620

Val Asp Val Leu Asp Val Pro Glu Gly Thr Leu Pro Asp Lys Gln Ser
625                 630                 635                 640

Thr Glu Gln Ala Ile Gln Leu Leu Glu Lys Met Lys Thr Ser Ala Ser
                645                 650                 655

Pro Phe Phe Leu Ala Val Gly Tyr His Lys Pro His Ile Pro Phe Arg
            660                 665                 670

Tyr Pro Lys Glu Phe Gln Lys Leu Tyr Pro Leu Glu Asn Ile Thr Leu
        675                 680                 685

Ala Pro Asp Pro Glu Val Pro Asp Gly Leu Pro Pro Val Ala Tyr Asn
690                 695                 700

Pro Trp Met Asp Ile Arg Gln Arg Glu Asp Val Gln Ala Leu Asn Ile
705                 710                 715                 720

Ser Val Pro Tyr Gly Pro Ile Pro Val Asp Phe Gln Arg Lys Ile Arg
                725                 730                 735

Gln Ser Tyr Phe Ala Ser Val Ser Tyr Leu Asp Thr Gln Val Gly Arg
            740                 745                 750

Leu Leu Ser Ala Leu Asp Asp Leu Gln Leu Ala Asn Ser Thr Ile Ile
        755                 760                 765

Ala Phe Thr Ser Asp His Gly Trp Ala Leu Gly Glu His Gly Glu Trp
770                 775                 780

Ala Lys Tyr Ser Asn Phe Asp Val Ala Thr His Val Pro Leu Ile Phe
785                 790                 795                 800

Tyr Val Pro Gly Arg Thr Ala Ser Leu Pro Glu Ala Gly Glu Lys Leu
                805                 810                 815

Phe Pro Tyr Leu Asp Pro Phe Asp Ser Ala Ser Gln Leu Met Glu Pro
            820                 825                 830

Gly Arg Gln Ser Met Asp Leu Val Glu Leu Val Ser Leu Phe Pro Thr
        835                 840                 845

Leu Ala Gly Leu Ala Gly Leu Gln Val Pro Pro Arg Cys Pro Val Pro
850                 855                 860
```

Ser Phe His Val Glu Leu Cys Arg Glu Gly Lys Asn Leu Leu Lys His
865                 870                 875                 880

Phe Arg Phe Arg Asp Leu Glu Glu Asp Pro Tyr Leu Pro Gly Asn Pro
            885                 890                 895

Arg Glu Leu Ile Ala Tyr Ser Gln Tyr Pro Arg Pro Ser Asp Ile Pro
            900                 905                 910

Gln Trp Asn Ser Asp Lys Pro Ser Leu Lys Asp Ile Lys Ile Met Gly
            915                 920                 925

Tyr Ser Ile Arg Thr Ile Asp Tyr Arg Tyr Thr Val Trp Val Gly Phe
    930                 935                 940

Asn Pro Asp Glu Phe Leu Ala Asn Phe Ser Asp Ile His Ala Gly Glu
945                 950                 955                 960

Leu Tyr Phe Val Asp Ser Asp Pro Leu Gln Asp His Asn Met Tyr Asn
                965                 970                 975

Asp Ser Gln Gly Gly Asp Leu Phe Gln Leu Leu Met Pro
            980                 985

<210> SEQ ID NO 7
<211> LENGTH: 2979
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gccgccacca tggactggac ctggagggtg ttctgcctgc ttgcagtggc ccccggagcc      60
cacagccagg ttcagctgca gcagtctgga cctgagctgt gaagcctggg gctttagtg     120 aagatatcct gcaaggcttc tggttacacc ttcacaaact acgatataca ctgggtgaag     180
cagaggcctg gacagggact tgagtggatt ggatggattt atcctggaga tggtagtact     240
aagtacaatg agaaattcaa gggcaaggcc acactgactg cagacaaatc ctccagcaca     300
gcctacatgc acctcagcag cctgacttct gagaaatctg cagtctattt ctgtgcaaga     360
gagtgggctt actggggcca agggactctg gtcactgtct ctgcagctag caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcaccc agacctacat ctgcaacgtg     660
aatcacaagc ccagcaacac caaggtggac aagaaagttg agcccaaatc ttgtgacaaa     720
actcacacat gcccaccgtg cccagcacct gaactcctgg ggggaccgtc agtcttcctc     780
ttccccccaa aacccaagga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca aagccctccc agcccccatc gagaaaacca tctccaaagc caagggcag    1080 ccccgagaac cacaggtgta caccctgccc ccatcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320

-continued

| | |
|---|---|
| ttctcatgct ccgtgatgca tgaggctctg cacaaccact acacgcagaa gagcctctcc | 1380 |
| ctgtctcctg gtagtagttc ctccgaaacg caggccaact cgaccacaga tgctctgaac | 1440 |
| gttcttctca tcatcgtgga tgacctgcgc ccctccctgg gctgttatgg ggataagctg | 1500 |
| gtgaggtccc caaatattga ccaactggca tcccacagcc tcctcttcca gaatgccttt | 1560 |
| gcgcagcaag cagtgtgcgc cccgagccgc gtttctttcc tcactggcag gagacctgac | 1620 |
| accacccgcc tgtacgactt caactcctac tggagggtgc acgctggaaa cttctccacc | 1680 |
| atcccccagt acttcaagga gaatggctat gtgaccatgt cggtgggaaa agtctttcac | 1740 |
| cctgggatat cttctaacca tactgatgat ctccgtgtata gctggtcttt tccaccttat | 1800 |
| catccttcct ctgagaagta tgaaaacact aagacatgtc gagggccaga tggagaactc | 1860 |
| catgccaacc tgcttttgccc tgtggatgtg ctggatgttc ccgagggcac cttgcctgac | 1920 |
| aaacagagca ctgagcaagc catacagttg ttggaaaaga tgaaaacgtc agccagtcct | 1980 |
| ttcttcctgg ccgttgggta tcataagcca cacatcccct tcagataccc caaggaattt | 2040 |
| cagaagttgt atcccttgga gaacatcacc ctggccccccg atcccgaggt ccctgatggc | 2100 |
| ctaccccctg tggcctacaa cccctggatg gacatcaggc aacgggaaga cgtccaagcc | 2160 |
| ttaaacatca gtgtgccgta tggtccaatt cctgtggact tcagcggaaa atccgccag | 2220 |
| agctactttg cctctgtgtc atatttggat acacaggtcg ccgcctctt gagtgctttg | 2280 |
| gacgatcttc agctggccaa cagcaccatc attgcattta cctcggatca tgggtgggct | 2340 |
| ctaggtgaac atggagaatg ggccaaatac agcaattttg atgttgctac ccatgttccc | 2400 |
| ctgatattct atgttcctgg aaggacggct tcacttccgg aggcaggcga aagcttttc | 2460 |
| ccttacctcg acccttttga ttccgcctca cagttgatgg agccaggcag gcaatccatg | 2520 |
| gaccttgtgg aacttgtgtc tcttttttccc acgctggctg gacttgcagg actgcaggtt | 2580 |
| ccacctcgct gccccgttcc ttcatttcac gttgagctgt gcagagaagg caagaaccttt | 2640 |
| ctgaagcatt ttcgattccg tgacttggaa gaggatccgg acctccctgg taatcccgt | 2700 |
| gaactgattg cctatagcca gtatccccgg ccttcagaca tccctcagtg gaattctgac | 2760 |
| aagccgagtt taaagatat aaagatcatg ggctattcca tacgcaccat agactatagg | 2820 |
| tatactgtgt gggttggctt caatcctgat gaatttctag ctaacttttc tgacatccat | 2880 |
| gcagggggaac tgtattttgt ggattctgac ccattgcagg atcacaatat gtataatgat | 2940 |
| tcccaaggtg gagatctttt ccagttgttg atgccttga | 2979 |

<210> SEQ ID NO 8
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| | |
|---|---|
| gccgccacca tggagacccc cgcccagctg ctgttcctgt tgctgctttg gcttccagat | 60 |
| actaccggcg acatccagat gacccagtct ccatcctcct tatctgcctc tctgggagaa | 120 |
| agagtcagtc tcacttgtcg ggcaagtcag gacattggtg gtaacttata ctggcttcag | 180 |
| cagggaccag atggaactat taaacgcctg atctacgcca catccagttt agattctggt | 240 |
| gtccccaaaa ggttcagtgg cagtaggtct gggtcagatt attctctcac catcagcagc | 300 |
| cttgagtctg aagattttgt agactattac tgtctacagt attctagttc tccgtggacg | 360 |

-continued

| | | | | | |
|---|---|---|---|---|---|
| ttcggtggag | gcacaaagct | ggaaataaaa | cgaactgtgg | ctgcaccatc | tgtcttcatc | 420
| ttcccgccat | ctgatgagca | gttgaaatct | ggaactgcct | ctgttgtgtg | cctgctgaat | 480
| aacttctatc | ccagagaggc | caaagtacag | tggaaggtgg | ataacgccct | ccaatcgggt | 540
| aactcccagg | agagtgtcac | agagcaggac | agcaaggaca | gcacctacag | cctcagcagc | 600
| accctgacgc | tgagcaaagc | agactacgag | aaacacaaag | tctacgcctg | cgaagtcacc | 660
| catcagggcc | tgagctcgcc | cgtcacaaag | agcttcaaca | ggggagagtg | ttag | 714